US012616500B2

(12) United States Patent
Flake et al.

(10) Patent No.: US 12,616,500 B2
(45) Date of Patent: May 5, 2026

(54) CANNULA INSERTION SYSTEM AND METHODS OF USING THE SAME

(71) Applicant: The Children's Hospital of Philadelphia, Philadelphia, PA (US)

(72) Inventors: Alan W. Flake, Philadelphia, PA (US); Marcus Graeme Davey, Ardmore, PA (US); Joseph W. Jackson, Wilmington, DE (US); Dylan J. Paproski, Littleton, CO (US); Ryan Christopher Meers, West Chester, PA (US); Joseph Gordon, Mansfield, MA (US); Dustin Gaidos, Milton, MA (US); Spencer Brown, Cranston, RI (US); Philip Bussone, Jr., Ipswich, MA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 548 days.

(21) Appl. No.: 17/921,523

(22) PCT Filed: Apr. 28, 2021

(86) PCT No.: PCT/US2021/029548
§ 371 (c)(1),
(2) Date: Oct. 26, 2022

(87) PCT Pub. No.: WO2021/222349
PCT Pub. Date: Nov. 4, 2021

(65) Prior Publication Data
US 2023/0125035 A1      Apr. 20, 2023

Related U.S. Application Data

(60) Provisional application No. 63/017,204, filed on Apr. 29, 2020.

(51) Int. Cl.
A61B 17/34      (2006.01)
A61M 1/36      (2006.01)
A61M 29/00      (2006.01)

(52) U.S. Cl.
CPC ...... *A61B 17/3421* (2013.01); *A61B 17/3403* (2013.01); *A61M 1/3659* (2014.02);
(Continued)

(58) Field of Classification Search
CPC ............ A61B 17/3421; A61B 17/3403; A61B 2017/3466; A61B 17/3417;
(Continued)

(56) References Cited

U.S. PATENT DOCUMENTS 2,600,240 A      6/1952 Grieb
2,723,660 A      11/1955 Greenberg
(Continued)

FOREIGN PATENT DOCUMENTS

CN      203663028 U      6/2014
CN      103381094 B      1/2015
(Continued)

OTHER PUBLICATIONS

Arens et al., "NeonatOxiA Pumpless Extracorporeal Lung Support for Premature Neonates", Artificial Organs, 2011, vol. 35, No. 11, 997-1001.
(Continued)

*Primary Examiner* — Leslie R Deak
*Assistant Examiner* — Eric Rassavong
(74) *Attorney, Agent, or Firm* — BakerHostetler

(57) ABSTRACT

A cannula insertion system for cannulating a blood vessel includes a cannula system having a cannula that defines a cannula lumen and has a distal and proximal end. The system includes a cannula insertion device for coupling with the system that includes a dilator having a dilator body and
(Continued)

a dilator lumen; a needle having a needle body and a needle lumen, the needle being translatable within the dilator lumen along a first direction; a movable dilator actuator configured to cause the dilator to move along the first direction; a movable needle actuator configured to cause movement of the needle along the first direction; and a housing defining housing recess. The housing recess is configured to receive the cannula system, the dilator, and the needle. The needle and the dilator are configured to be moved within the cannula lumen along the first direction.

25 Claims, 32 Drawing Sheets

(52) U.S. Cl.
CPC ..... *A61M 29/00* (2013.01); *A61B 2017/3466* (2013.01); *A61M 2240/00* (2013.01)

(58) Field of Classification Search
CPC .... A61B 2017/3409; A61B 2017/3488; A61B 17/3423; A61B 2017/3405–3413; A61B 2017/3425; A61B 2017/3454; A61M 1/3659; A61M 29/00; A61M 2240/00; A61M 25/0606; A61M 1/3661

See application file for complete search history.

(56) References Cited

U.S. PATENT DOCUMENTS

| | | | |
|---|---|---|---|
| 4,048,684 A | 9/1977 | Korner et al. | |
| 4,509,505 A | 4/1985 | Mercey et al. | |
| 4,617,912 A | 10/1986 | Beer et al. | |
| 4,796,605 A | 1/1989 | Sasaki et al. | |
| 5,063,924 A | 11/1991 | Galvan et al. | |
| 5,207,639 A | 5/1993 | Cooper | |
| 5,218,958 A | 6/1993 | Cooper | |
| 5,308,310 A | 5/1994 | Roff et al. | |
| 5,494,032 A | 2/1996 | Robinson et al. | |
| 5,676,681 A | 10/1997 | Yoon | |
| 5,685,856 A | 11/1997 | Lehrer | |
| 5,695,479 A | 12/1997 | Jagpal | |
| 6,120,494 A | 9/2000 | Jonkman | |
| 6,436,119 B1 | 8/2002 | Erb et al. | |
| 6,611,978 B1 | 9/2003 | Schmidt et al. | |
| 6,638,247 B1 | 10/2003 | Selmon et al. | |
| 8,333,686 B2 | 12/2012 | Marseille et al. | |
| 8,715,294 B2 | 5/2014 | Ortiz et al. | |
| 10,058,343 B2 * | 8/2018 | Malkowski | A61B 17/29 |
| 10,085,907 B2 | 10/2018 | Flake et al. | |
| 10,682,125 B2 | 6/2020 | Snow | |
| 2001/0033813 A1 | 10/2001 | Filho et al. | |
| 2002/0069877 A1 | 6/2002 | Villareal et al. | |
| 2004/0133064 A1 | 7/2004 | Castillon et al. | |
| 2004/0193096 A1 | 9/2004 | Cooper | |
| 2005/0056787 A1 | 3/2005 | Cong et al. | |
| 2005/0124850 A1 | 6/2005 | Mackin | |
| 2006/0247678 A1 | 11/2006 | Weisenburgh et al. | |
| 2007/0010005 A1 | 1/2007 | Sitzmann | |
| 2007/0043380 A1 | 2/2007 | Ortiz et al. | |
| 2007/0162071 A1 * | 7/2007 | Burkett | A61F 2/01 606/200 |
| 2008/0014622 A1 | 1/2008 | Federspiel et al. | |
| 2008/0274546 A1 | 11/2008 | Kabayama et al. | |
| 2009/0149776 A1 | 6/2009 | Adams | |
| 2010/0028979 A1 | 2/2010 | Faulkner et al. | |
| 2010/0101657 A1 | 4/2010 | Morley et al. | |
| 2010/0168502 A1 | 7/2010 | Delaporte et al. | |
| 2010/0204652 A1 * | 8/2010 | Morrissey | A61M 5/158 604/164.08 |
| 2011/0125010 A1 | 5/2011 | Vaquero et al. | |
| 2012/0226258 A1 | 9/2012 | Otto et al. | |
| 2013/0274543 A1 | 10/2013 | Matsubara et al. | |
| 2014/0025036 A1 | 1/2014 | Bierman et al. | |
| 2015/0094751 A1 | 4/2015 | Chen et al. | |
| 2016/0022524 A1 | 1/2016 | Flake et al. | |
| 2016/0038045 A1 | 2/2016 | Shapiro | |
| 2016/0270993 A1 | 9/2016 | Wilden et al. | |
| 2017/0128322 A1 | 5/2017 | Fassihi et al. | |
| 2018/0256088 A1 | 9/2018 | Ray | |
| 2019/0060616 A1 | 2/2019 | Solomon | |
| 2019/0380900 A1 | 12/2019 | Flake et al. | |
| 2020/0094025 A1 | 3/2020 | Wisman | |
| 2020/0107823 A1 | 4/2020 | Hundertmark et al. | |
| 2020/0337722 A1 * | 10/2020 | Charles | A61F 9/0008 |
| 2021/0161744 A1 | 6/2021 | Flake et al. | |
| 2021/0204820 A1 | 7/2021 | Zhang et al. | |

FOREIGN PATENT DOCUMENTS

| | | | |
|---|---|---|---|
| EP | 0447256 A2 | 9/1991 | |
| EP | 1049510 B1 | 10/2003 | |
| GB | 1082381 A | 9/1967 | |
| JP | 08-294519 A | 11/1996 | |
| JP | 2010-518907 A | 6/2010 | |
| JP | 2013-066756 A | 4/2013 | |
| JP | 2013-233194 A | 11/2013 | |
| JP | 2016-064032 A | 4/2016 | |
| JP | 2016-513571 A | 5/2016 | |
| JP | 2016-537096 A | 12/2016 | |
| JP | 2020-501679 A | 1/2020 | |
| RU | 2376969 C1 | 12/2009 | |
| WO | 98/39039 A1 | 9/1998 | |
| WO | WO-9937354 A1 * | 7/1999 | A61B 17/3417 |
| WO | 2006/125955 A1 | 11/2006 | |
| WO | 2013/026148 A1 | 2/2013 | |
| WO | 2013/029044 A1 | 2/2013 | |
| WO | 2014/145494 | 9/2014 | |
| WO | 2016/052517 A1 | 4/2016 | |
| WO | WO-2016153357 A2 * | 9/2016 | A61B 17/122 |
| WO | 2016/205622 A1 | 12/2016 | |
| WO | 2018/171905 A1 | 9/2018 | |
| WO | WO-2018169503 A1 * | 9/2018 | A61B 17/00234 |
| WO | 2019/046456 A1 | 3/2019 | |

OTHER PUBLICATIONS

Awad et al., Pumpless Respiratory Assistance Using a Membrane Oxygenator as an Artificial Placenta: A Preliminary Study in Newborn and Preterm Lambs, 1995, J. Invest. Surg., 8:21-30.

Behrman et al., "Preterm Birth: Causes, Consequences, and Prevention", Institute of Medicine (US), National Academies Press, 2007, 791 pages.

Boston et al., Paracorporeal lung assist device: An innovative surgical strategy for bridging to lung transplant in an infant with severe pulmonary hypertension caused by alveolar capillary dysplasia, Oct. 2013, J. Thorac. Cardiovasc. Surg., 146:e42-e43.

Callaghan et al., Studies in the Development of an Artificial Placenta, 1963, Circulation 27:686-690.

Creasy et al., Determination of Fetal, Placental and Neonatal Blood Volumes in the Sheep, Oct. 1970, Circulation Research, Res., 27:487-494.

Crossley et al., "Suppression of Arousal by Progesterone in Fetal Sheep", Reproduction, fertility and development, 1997, vol. 9, No. 8, 767-774.

European Application 14763073, Supplementary European Search Report dated Jan. 4, 2017, 7 pages.

Faber et al., Foetal Placental Blood Flow in the Lamb, 1972, J. Pysiol., 223:375-393.

Hanif et al., "Variables that affect the middle cerebral artery peak systolic velocity in fetuses with anemia and intrauterine growth restriction", Am. J. Perinatal., Sep. 2007, 24, 501-505.

Huddleston et al., Lung Transplantation in Children, 2002, Ann Surg., 236:270-276.

Ijsselstein et al., "Long-Term Outcome of Children Treated with Neonatal Extracorporeal Membrane Oxygenation: Increasing Problems with Increasing Age", Semin. Perinatal., Mar. 2014, vol. 38, 114-121.

(56) References Cited

OTHER PUBLICATIONS

International Patent Application No. PCT/US2017/065950, Int'l Preliminary Report on Patentability, dated Jun. 27, 2019, 7 pages.
International Search Report and Written Opinion issued in International Application No. PCT/US14/30277 on Aug. 11, 2014.
Kumar et al., Post extracorporeal membrane oxygenation single photon emission computed tomography (SPECT) as a predictor of neurodevelopmental outcome, Jun. 1994, Pediatrics 93:951-955.
Kuwabara et al., Artificial Placenta: Long-Term Extrauterine Incubation of Isolated Goat Fetuses, Dec. 1989, Artificial Organs 13:527-531.
Kuwabara et al., Development of Extrauterine Fetal Incubation System Using Extracorporeal Membrane Oxygenator, 1987, Artificial Organs 11:224-227.
Martin et al., Preterm Births—United States, 2006 and 2010, MMWR Surveill. Summ., 62 (Suppl 3): 136-138, Nov. 2013.
Mirua et al., "Novel modification of an artificial placenta: pumpless arteriovenous extracorporeal life support in a premature lamb model", Pediatr. Res., 2012, 72:490-494.
Miura et al., Novel modification of an artificial placenta: pumpless arteriovenous extracorporeal life support in a premature lamb model, Pediaric Research, Nov. 19, 2012, [Retrieved on Jul. 21, 2014], Retrieved from the internet: <http://www.nature.com/pr/journal/v72/n5/full/pr2012108a/html>.
Papademetriou et al., Wavelet Cross-Correlation to Investigate Regional Variations in Cerebral Oxygenation in Infants Supported on Extracorporeal Membrane Oxygenation, 2013, Adv. Exp. Med. Biol., 765:203-209.
Reoma et al., "Development of an Artificial Placenta I: Pumpless Arterio-Venous Extracorporeal Life Support in a Neonatal Sheep Model", Journal of Pediatric Surgery, 2009, vol. 44, 53-59.
Rochow et al., "Integrated Microfluidic Oxygenator Bundles For Blood Gas Exchange in Premature Infants", MEMS 2012, Paris, France, Jan. 2012, 957-960.

Rochow et al., "Artificial Placenta—Lung Assist Devices for Term and Pre-term Newborns With Respiratory Failure", Int. J. Artif. Organs, 2013, 36(6) pp. 377-391.
Schoberer et al., "Miniaturization: the clue to clinical application of the artificial placenta", Artificial Organs, Mar. 2014, 38, 208-214.
Short et al., Impairment of Cerebral Autoregulation during Extracorporeal Membrane Oxygenation in Newborn Lambs, 1993, Pediatr. Res., 33:289-294.
Stolar et al., Extracorporeal membrane oxygenation causes significant changes in intracranial pressure and carotid artery blood flow in newborn lambs, Dec. 1988, J. Pediatr. Surg., 23:1163-1168.
Unno et al., An Evaluation of the System to Control Blood flow in Maintaining Goat Fetuses on Arterio-Venous Extracorporeal membrane Oxygenation: A Novel Approach to the Development of an Artificial Placenta, Dec. 1997, Artificial Organs 21:1239-1246.
Unno et al., Development of an Artificial Placenta: Survival of Isolated Goat Fetuses for Three Weeks with Umbilical Arteriovenous Extracroporeal Membrane Oxygenation, Dec. 1993, Artificial Organs 17:996-1003.
Vutskits, "Cerebral blood flow in the neonate", Pediatr. Anesth., 2014, 24, 22-29.
Walker et al., Impairment of cerebral autoregulation during venovenous extracorporeal membrane oxygenation in the newborn lamb, Dec. 1996, Crit. Care Med., 24:2001-2006.
Yasufuku et al., Arterio-venous extracorporeal membrane oxygenation of fetal goat incubated in artificial amniotic fluid (Artificial placenta): Influence on lung growth and maturation, Mar. 1998, J. Pediatr. Surg., 33:442-448.
Zapol et al., Artificial Placenta: Two Days of Total Extrauterine Support of the Isolated Premature Lamb Fetus, Oct. 1969, Science 166:617-618.
Muller et al., "Pharmacokinetics of Penicillin G in Infants with a Gestational Age of Less than 32 Weeks," Antimicrob. Agents Chemotherap., Oct. 2007, 51(10): 3720-3725.

* cited by examiner

CANNULA INSERTION SYSTEM AND METHODS OF USING THE SAME

CROSS REFERENCE TO RELATED APPLICATIONS

This application is a National Phase entry of International Application No. PCT/US2021/029548, filed Apr. 28, 2021, which claims priority to and the benefit of U.S. Provisional Application No. 63/017,204, filed Apr. 29, 2020, the entirety entireties of which is are incorporated herein for any and all purposes.

TECHNICAL FIELD

The present disclosure is related to embodiments of a cannula insertion system, including a cannula system and a cannula insertion device.

BACKGROUND

Extreme prematurity is the leading cause of infant morbidity and mortality in the United States, with over one third of all infant deaths and one-half of cerebral palsy diagnoses attributed to prematurity. Respiratory failure represents the most common and challenging problem associated with extreme prematurity, as gas exchange in critically preterm neonates is impaired by structural and functional immaturity of the lungs. Advances in neonatal intensive care have achieved improved survival and pushed the limits of viability of preterm neonates to 22 to 24 weeks gestation, which marks the transition from the canalicular to the saccular phase of lung development. Although survival has become possible, there is still a high rate of chronic lung disease and other complications of organ immaturity, particularly in neonates born prior to 28 weeks gestation. The development of a system that could support normal neonatal growth and organ maturation for even a few weeks could significantly reduce the morbidity and mortality of extreme prematurity, and improve quality of life in survivors.

SUMMARY

The above deficiencies are addressed by cannula insertion systems and methods of using them described throughout this specification. According to an aspect of this disclosure, a cannula insertion system for cannulating a blood vessel of a tissue includes a cannula system having a cannula that defines a cannula lumen therethrough. The cannula has a distal end and a proximal end opposite the distal end. The cannula insertion system further includes a cannula insertion device configured to couple with the cannula system. The coupling between the cannula insertion device and the cannula system may be releasable. The cannula insertion device includes a dilator having a dilator body that defines a dilator lumen therethrough; a needle having a needle body that defines a needle lumen therethrough, the needle being translatable within the dilator lumen along a first direction; a dilator actuator configured to be moved such that movement of the dilator actuator causes movement of the dilator along the first direction; a needle actuator configured to be moved such that movement of the needle actuator causes movement of the needle along the first direction; and a housing defining a housing recess therein. The housing recess is configured to receive the cannula system, the dilator, and the needle. The needle and the dilator of the cannula insertion device are configured to be moved within the cannula lumen along the first direction.

The actuator may be configured to translate the needle from a first position, in which a distal end of the needle is positioned distally of a distal end of the dilator, to a second position, in which the distal end of the needle is positioned proximally of the distal end of the dilator.

The cannula system may include a Y-connector adjacent to the proximal end of the cannula, the Y-connector having a first proximal portion, which defines a first proximal channel, and a second proximal portion, which defines a second proximal channel. The first and second proximal channels may be configured to be in fluid communication with the cannula lumen. In some aspects, the first proximal portion may define a slit seal that separates the first proximal channel from the second proximal channel. The slit seal has an open configuration, in which the dilator and the needle are inserted therethrough, and a closed configuration, in which the needle and the dilator are not extending therethrough. When the slit seal is in the closed configuration, liquid from the cannula lumen is precluded from moving into the first proximal channel. In some aspects, the cannula insertion system may include a plug configured to be removably inserted into the first proximal channel.

The cannula system may include a locking element thereon, and the housing may include a locking element thereon as well. The locking element of the cannula system can be configured to releasably engage with the locking element of the housing such that the cannula system is affixed to the housing.

The system may further include a collet jaw configured to releasably secure the cannula to the blood vessel. The collet jaw may be affixed to the cannula system. The collet jaw may have a base, a deformable arm, and a head. When the collet jaw is in an open position, the head is spaced away from the blood vessel and the cannula, and when the collet jaw is in a closed position, the head is in contact with the tissue such that the blood vessel is held in place between the collet jaw and the cannula.

The tissue may be physiological tissue, such as an organ. In some aspects, the tissue may include an umbilical cord of a neonate. The head of the collet jaw may contact an umbilical sheath of the umbilical cord, Wharton's jelly of the umbilical cord, or the blood vessel itself. In some aspects, the collet jaw may include a tine on the head that extends towards the blood vessel. The tine may be configured to dig into the tissue (e.g., the umbilical cord) when the collet jaw is in the second position.

In some aspects, the housing of the system may include a translucent portion configured to allow visibility through the housing into the housing recess.

The cannula system may be configured to be operatively connected to an extracorporeal membrane oxygenation (ECMO) system.

In some aspects, the cannula insertion system may be used outside of the cardiovascular system, for example, in the urinary system, in the digestive system, in the lymphatic system, or in another portion of the body. In some aspects, the cannula insertion system may be used with a ureter. In other aspects, the cannula insertion system may be used with a bile duct.

According to another aspect of the disclosure, a method of cannulating a blood vessel in a tissue includes the steps of: creating an opening in a wall of the blood vessel by piercing the wall with a distal end of a needle by moving the needle towards the vessel and through the wall of the vessel; inserting a dilator into the opening and expanding the opening; retracting the needle such that the needle is moved out of the blood vessel; retracting the dilator such that the dilator is moved out of the blood vessel; inserting a cannula into the opening in the wall of the blood vessel; and securing the cannula in the blood vessel. The cannula defines a cannula lumen therethrough extending between a distal end and a proximal end. The dilator and the needle are movable within the cannula lumen. The steps described herein need not be performed in the listed order.

In some aspects of the method, the needle may define a distal end and a proximal end opposite the distal end and the dilator may define a dilator lumen extending through the dilator between a distal end and a proximal end. The step of retracting the needle may include moving the needle in the dilator lumen from a first position, in which the distal end of the needle is outside of the dilator lumen and is distal to the distal end of the dilator, to a second position, in which the distal end of the needle is in the dilator lumen and is proximal to the distal end of the dilator.

The step of securing the cannula to the blood vessel may include moving a collet jaw from an unlocked position, in which the collet jaw does not contact the tissue, to a locked position, in which the collet jaw forcefully clamps the tissue such that the blood vessel is held between the collet jaw and the cannula such that at least a portion of the blood vessel is precluded from translating relative to the cannula. In some aspects, the method may further include the step of digging into the tissue with a tine disposed on the collet jaw.

The tissue may be physiological tissue, such as an organ. In some aspects, the tissue may include an umbilical cord of a neonate.

The method may include the step of connecting the cannula to an extracorporeal membrane oxygenation (ECMO) system.

In some aspects, the cannula may be connected to a Y-connector that splits into a first proximal portion and a second proximal portion separate from the first proximal portion. The step of connecting the cannula to the ECMO system may include connecting the second proximal portion of the Y-connector to the ECMO system.

The method may further include the step of moving the dilator and the needle out of the cannula lumen after the step of securing the blood vessel to the cannula. In some aspects, the cannula may be connected to a Y-connector that splits into a first proximal portion and a second proximal portion separate from the first proximal portion, and the step of moving the dilator and the needle out of the cannula lumen may include moving the dilator and the needle through the first proximal portion. In some aspects, the method may further include moving the needle and the dilator through a slit seal defined in the first proximal portion of the Y-connector.

In some aspects, the method may further include the step of inserting a plug into a first proximal channel of the Y-connector to prevent blood flow out of the first proximal portion.

According to another aspect of the disclosure, a cannula system includes a cannula having a distal end and a proximal end opposite the distal end; a cannula lumen extending through the cannula between the distal end and the proximal end; and a slit seal disposed on the cannula, the slit seal being configured to receive a cannula insertion device. The cannula system is configured to be in fluid communication with a blood vessel and with an oxygenator. The blood vessel may be in a tissue. The tissue may be physiological tissue, such as an organ. In some aspects, the tissue may include an umbilical cord of a neonate, and the cannula system may be configured to be in fluid communication with a blood vessel of the umbilical cord and with the oxygenator.

In some aspects, the cannula of the cannula system may further include a Y-shaped connector having a first proximal portion and a second proximal portion; and a slit seal disposed on the cannula. The slit seal may be configured to receive a cannula insertion device therethrough. The cannula lumen may extend through the second proximal portion of the Y-shaped connector. The slit seal may be configured to allow fluid communication between the first proximal portion and the cannula lumen. The cannula system may optionally include one or more features of cannula systems described throughout this application.

According to another aspect of the disclosure, a cannula for fluidly communicating with a vessel of a tissue includes a distal end; a proximal end opposite the distal end; a cannula lumen extending through the cannula between the distal end and the proximal end; a Y-shaped connector having a first proximal portion and a second proximal portion; and a slit seal disposed on the cannula, the slit seal being configured to receive a cannula insertion device therethrough. The cannula lumen extends through the second proximal portion of the Y-shaped connector. The slit seal is configured to allow fluid communication between the first proximal portion and the cannula lumen. The tissue may be physiological tissue, such as an organ. In some aspects, the tissue may include an umbilical cord of a neonate. The cannula may optionally include one or more features of cannulas described throughout this application.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, the drawings depict illustrative embodiments. It should be understood, however, that the application is not limited to the specific embodiments and methods disclosed, and reference is made to the claims for that purpose. In the drawings:

Figures 18A, 18B, 18C, 18D, 18E, 18F:
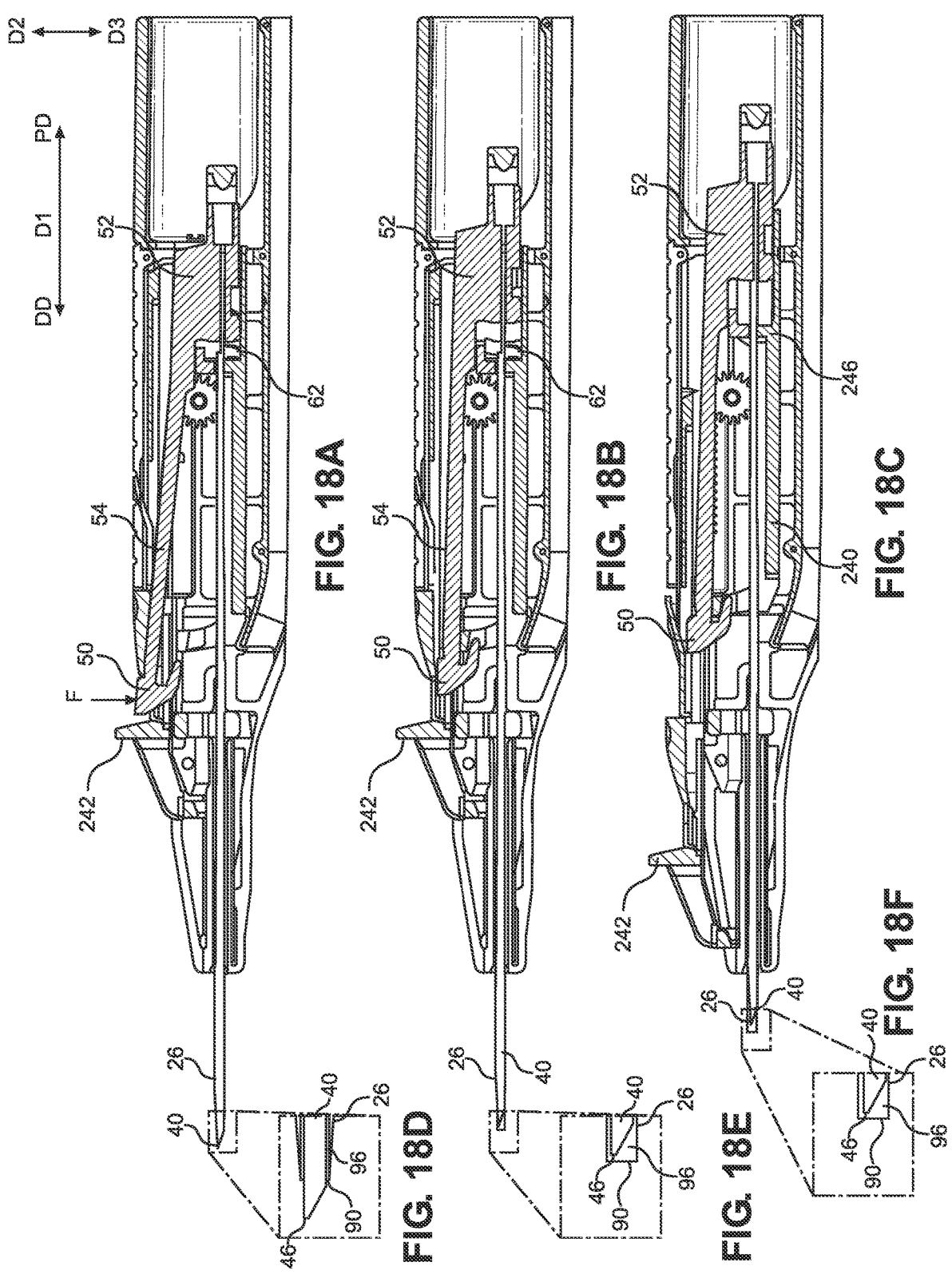
FIG. 18A is a side cross-sectional view of a cannula insertion device with the needle and the dilator in the extended positions according to an aspect of this disclosure.
FIG. 18B is a side cross-sectional view of a cannula insertion device with the needle in the retracted position and the dilator in the extended position according to an aspect of the disclosure.
FIG. 18C is a side cross-sectional view of a cannula insertion device with the needle and the dilator in the retracted positions according to an aspect of the disclosure.
FIG. 18D is a close-up cross-sectional view of a portion of the cannula insertion device shown in FIG. 18A.
FIG. 18E is a close-up cross-sectional view of a portion of the cannula insertion device shown in FIG. 18B.
Figure 19:
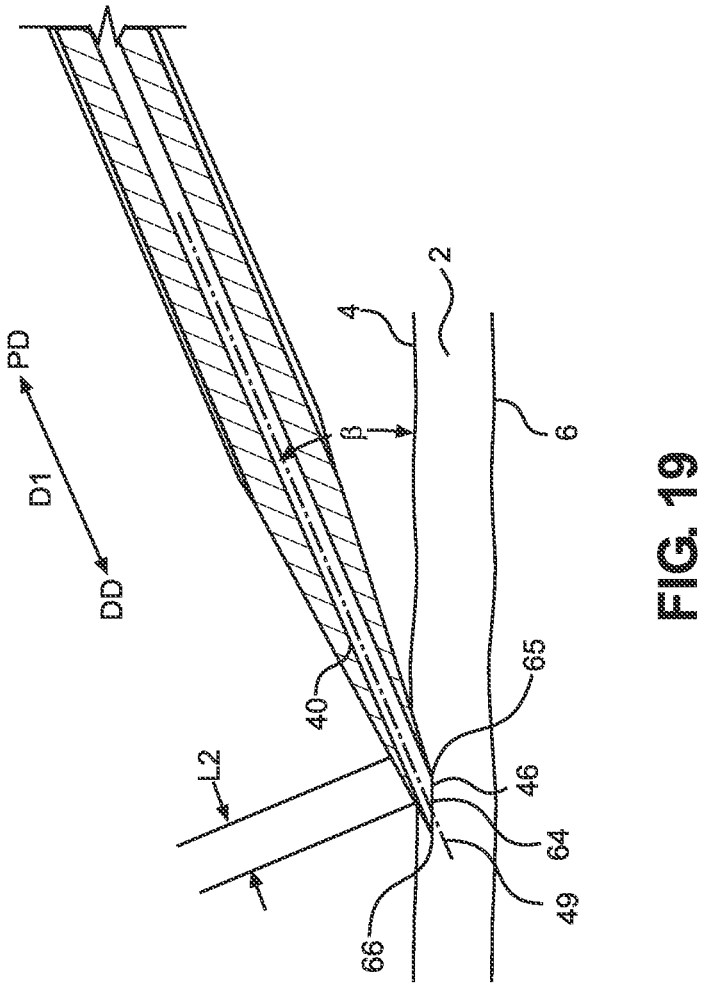
Figure 20:
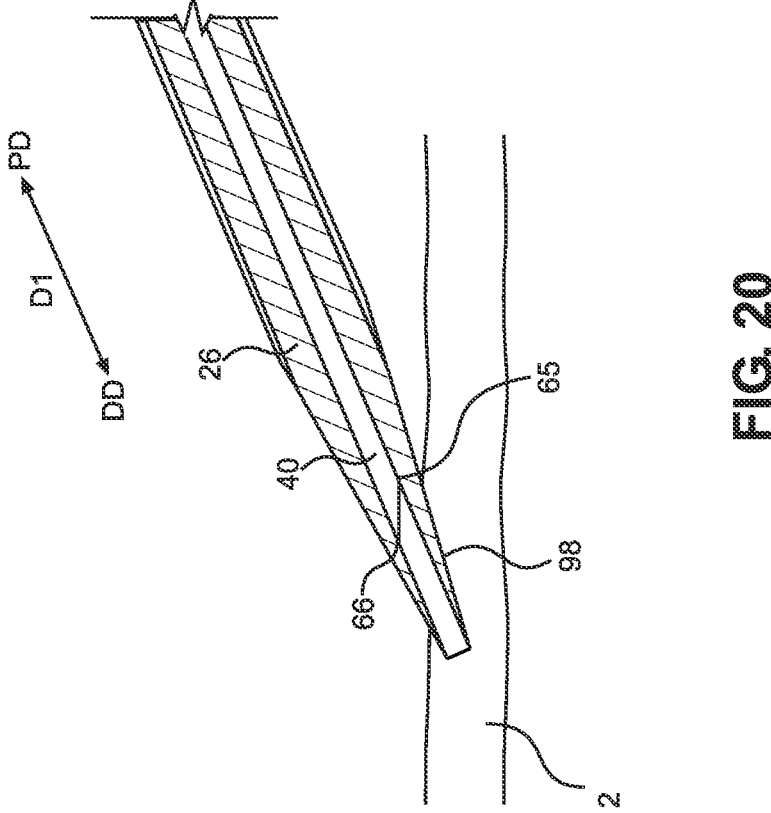
Figure 21:
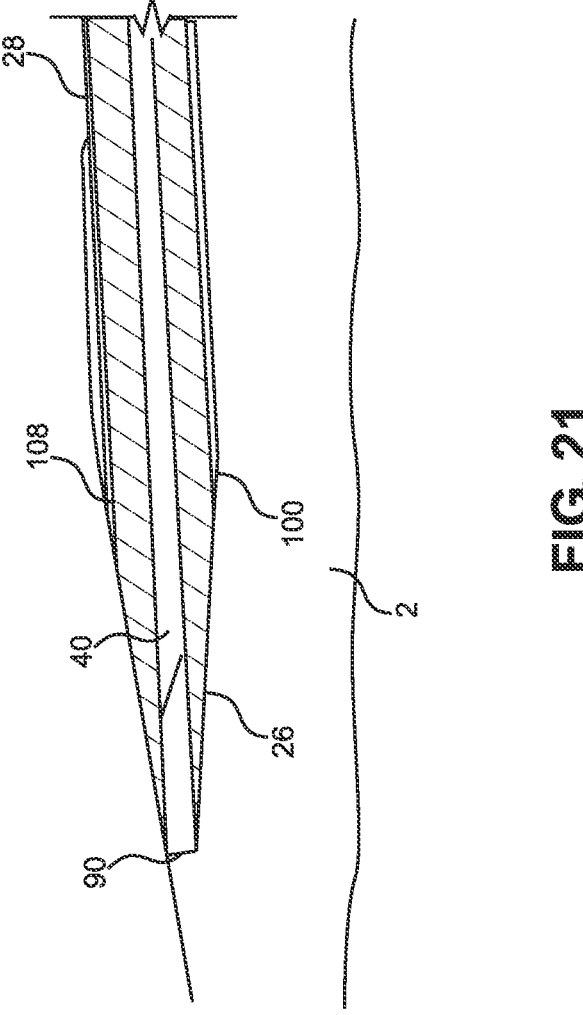
Figure 22:
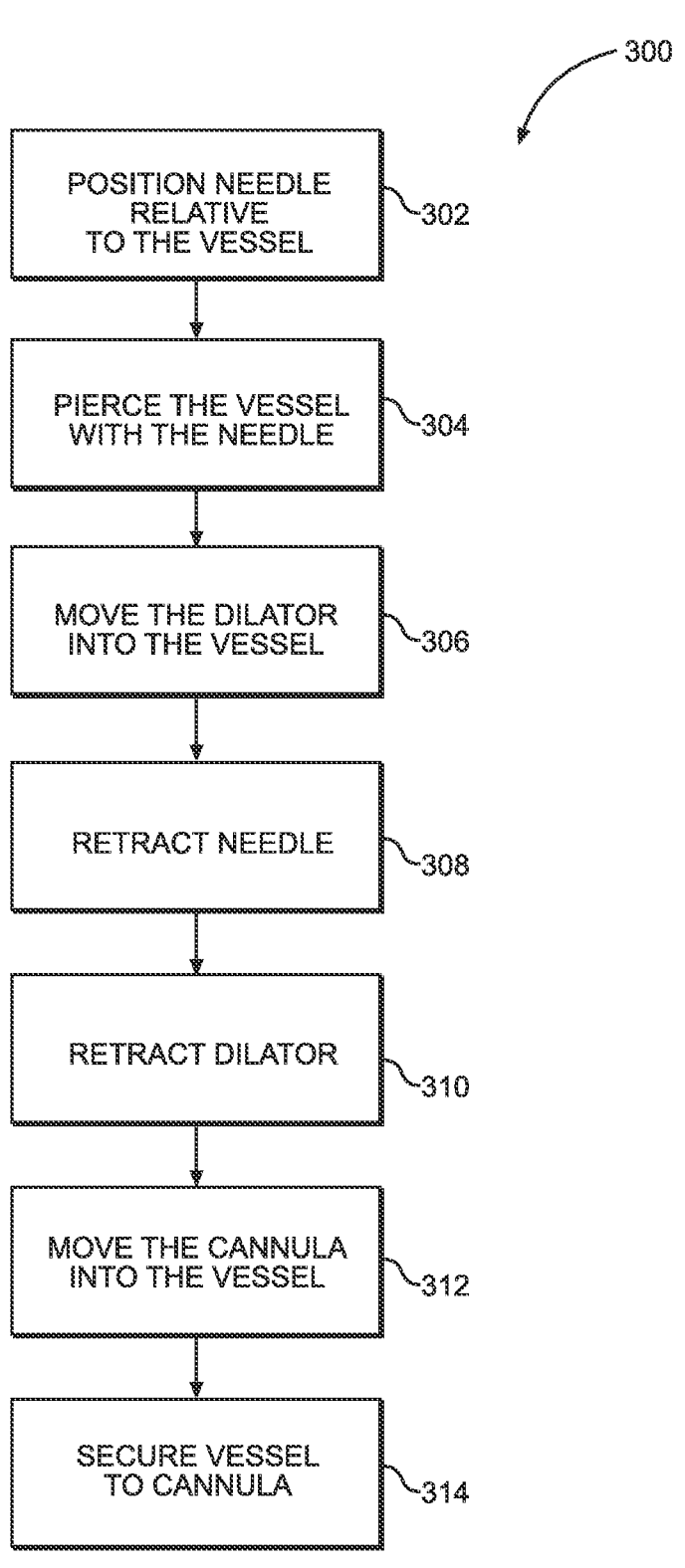
Figure 23:
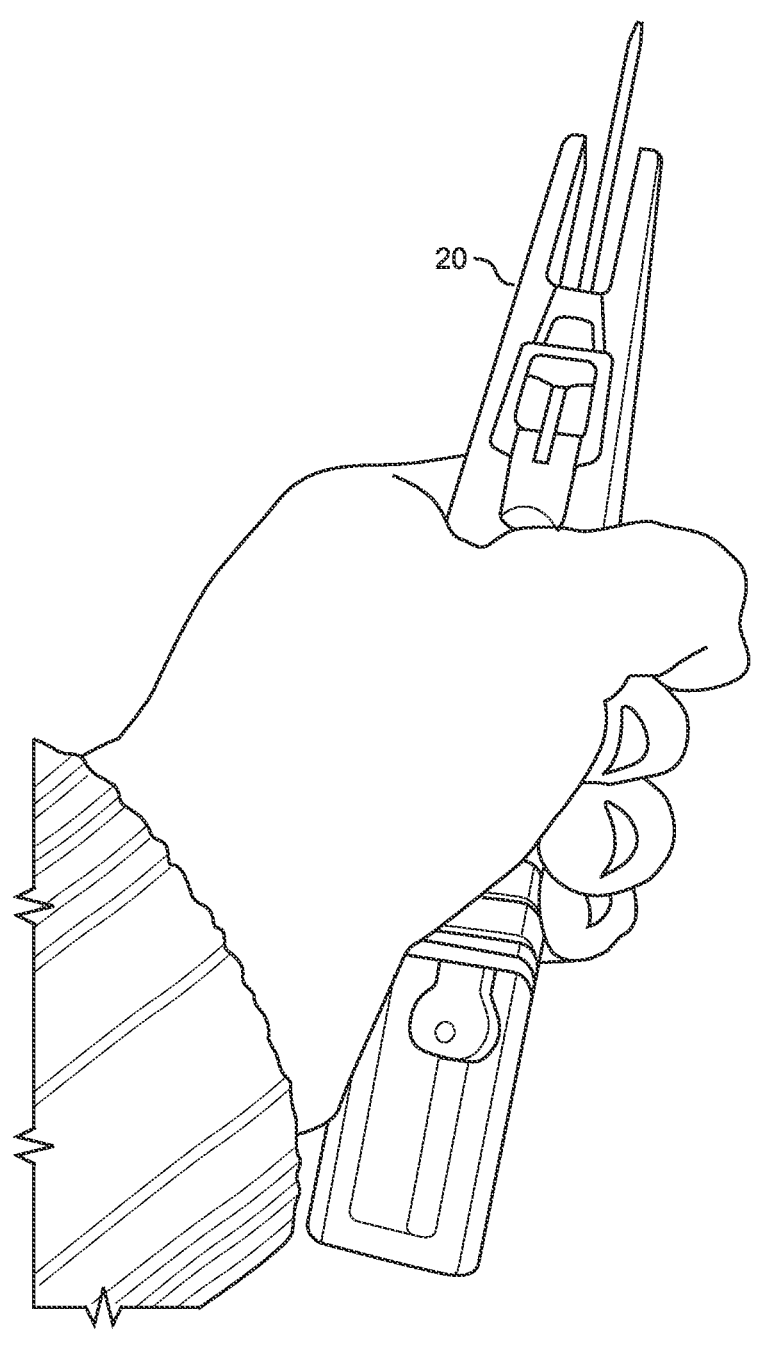
Figure 24A:
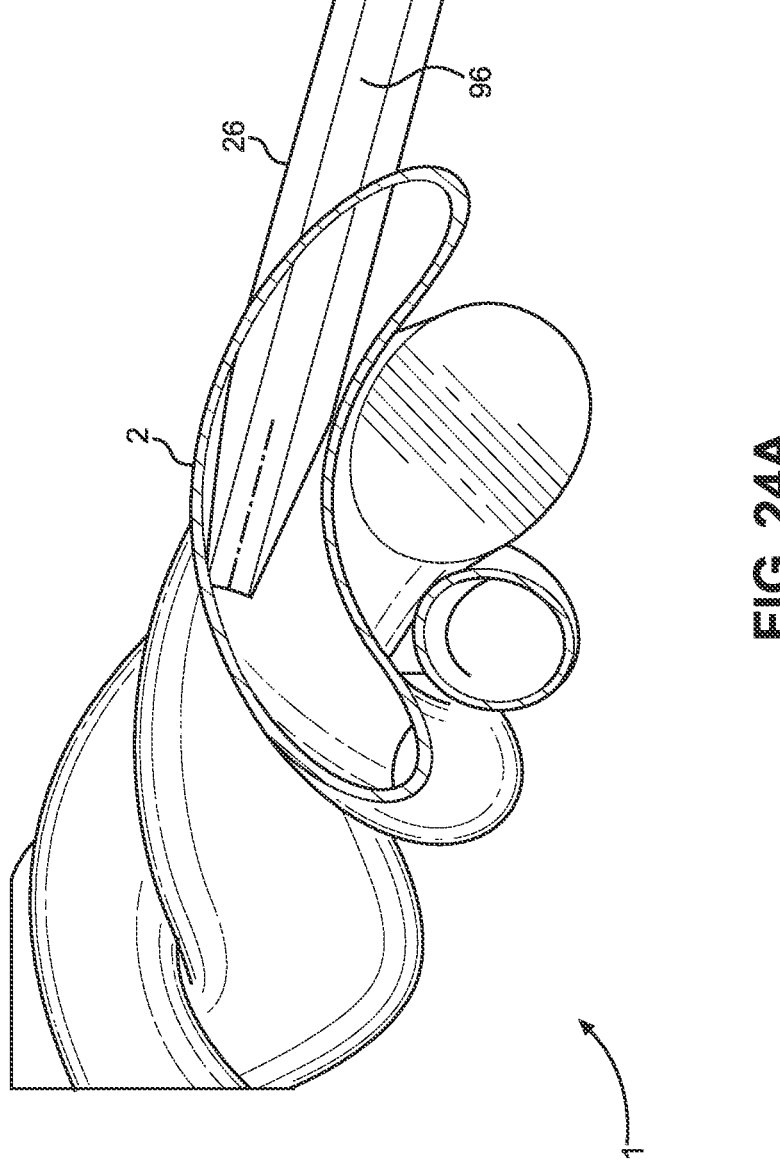
Figure 24B:
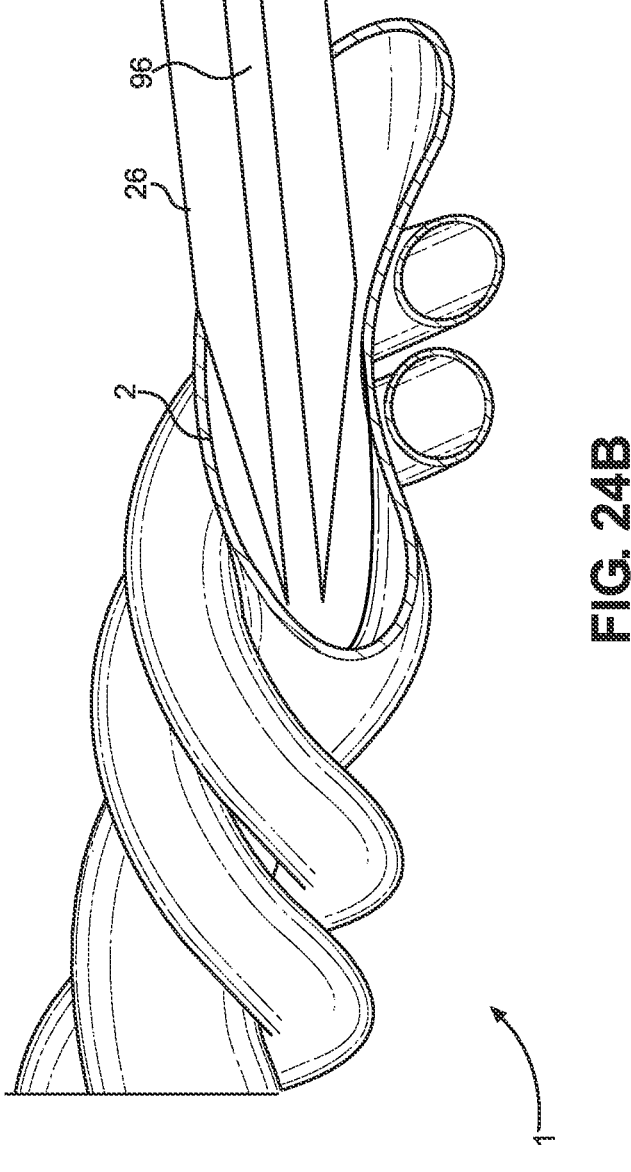
Figure 25:
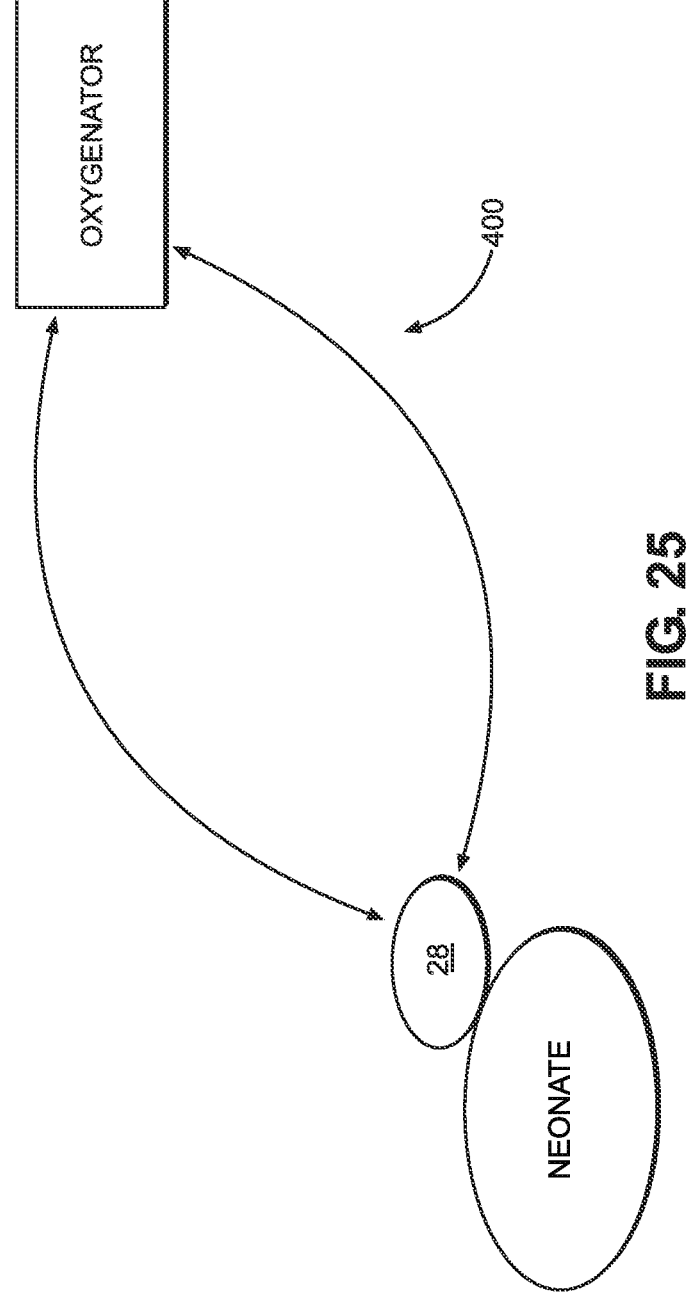

18F is a close-up cross-sectional view of a portion of the cannula insertion device shown in FIG. 18C;

FIG. 19 is a side cross-sectional view depicting the step of piercing a vessel with a needle according to an aspect of the disclosure;

FIG. 20 is a side cross-sectional view depicting the step of inserting the dilator into the vessel of FIG. 19 according to an aspect of the disclosure;

FIG. 21 is a side cross-sectional view depicting the step of inserting the cannula into the vessel of FIGS. 19 and 20 according to an aspect of the disclosure;

FIG. 22 depicts a process of cannulating a vessel with a cannula insertion system according to an aspect of the disclosure;

FIG. 23 depicts an exemplary view of a user holding the cannula insertion device in a hand;

FIG. 24A depicts a step of cannulating an arterial vessel according to an aspect of the disclosure;

FIG. 24B depicts a step of cannulating a venous vessel according to an aspect of the disclosure; and FIG. 25 depicts a schematic showing an external circulation circuit connected to the cannula system.

DETAILED DESCRIPTION OF ILLUSTRATIVE EMBODIMENTS

Certain terminology is used in the following description for convenience only and is not limiting. The term "aligned" as used herein in reference to two elements along a direction means a straight line that passes through one of the elements and that is parallel to the direction will also pass through the other of the two elements.

Aspects of the disclosure will now be described in detail with reference to the drawings, wherein like reference numbers refer to like elements throughout, unless specified otherwise. Certain terminology is used in the following description for convenience only and is not limiting. The term "plurality," as used herein, means more than one. The terms "a portion" and "at least a portion" of a structure include the entirety of the structure. Certain features of the disclosure that are described herein in the context of separate embodiments may also be provided in combination in a single embodiment. Conversely, various features of the disclosure that are described in the context of a single embodiment may also be provided separately or in any subcombination. The terms "proximal" and "distal" can refer to the position of a portion of a device relative to the remainder of the device or the opposing end as it appears in the drawing. The proximal end can be used to refer to the end manipulated by the user. The distal end can be used to refer to the end of the device that is inserted and advanced and is furthest away from the user. As will be appreciated by those skilled in the art, the use of proximal and distal could change in another context, e.g., the anatomical context in which proximal and distal use the patient as reference, or where the entry point is distal from the user.

One of the challenges associated with existing systems that could support normal neonatal growth and organ maturation is connection of the neonate's circulatory system to an oxygenator configured to oxygenate the neonate's blood supply once the neonate is removed from the womb. Cannulation of small vessels, such as the arteries and vein in an umbilical cord, requires precise manipulation of the device being used in the cannulation procedure. In addition, the blood supply within the neonate is small, so cannulation of the vessels within an umbilical cord must be done quickly and with as little neonatal blood loss as possible to maximize the chance of a successful outcome. Further, lowering the time required to cannulate an umbilical cord and reducing the amount of stimuli applied to the umbilical cord can reduce or prevent the umbilical cord from spasming, as well as decrease the time the neonate is not receiving oxygen, thus lowering the chance of adverse effects due to hypoxia.

Accordingly, a cannula insertion system configured to quickly, efficiently, and safely create an opening into a vessel, such as a vein or artery within an umbilical cord, attach a cannula to the vessel to provide a passageway into and out of the vessel, and establish a blood flow between the neonate and an oxygenator may result in an increase in successful outcomes of cannulation procedures.

Generally, a cannula insertion system can include a cannula insertion device configured to open a passageway into a vessel and insert a cannula into the vessel, such that blood can move from the vessel into the cannula, or vice versa. The cannula insertion system may also include a needle assembly, a dilator assembly, and a cannula. The vessel can be inside a body, such as a human body. According to one aspect of the disclosure, the vessel can form a portion of an external blood circuit outside of a body, such as an umbilical cord of a full-term or premature neonate.

The disclosed aspects can be utilized with various humans or animals. Specifically, these embodiments can be used to cannulate a blood vessel in the umbilical cord of a child, such as a premature neonate. When the vessel is cannulated, blood can flow from the umbilical cord through the cannula and to a desired destination, such as an external blood circulation circuit. Some of the disclosed allow for the cannulation process to be performed single-handedly and without additional tools or assistance, thus improving simplicity and reducing the need for extra components or people in the cannulation space. This lowers the risk of using an incorrect medical tool or improperly combining various tools in an attempt to achieve cannulation. By allowing the user to operate the cannula insertion system with one hand, the user's other hand is free to perform other tasks.

In some aspects, the systems disclosed throughout this application may be used outside of the cardiovascular system. In some aspects, the systems may be used for cannulating a lumen or vessel in the urinary system, in the digestive system, in the lymphatic system, or in another portion of the body. For example, in some aspects, the systems and methods described herein may be used with a ureter or with a bile duct.

In one preferred embodiment, a cannula insertion system includes a cannula insertion device and a cannula system. The cannula system can be used to transport blood from a neonate between one or more external medical devices. The cannula system can be removably connected to the umbilical cord of the neonate. For example, the cannula insertion system can have a plurality of cannula systems that are each connected to a separate blood vessel in the umbilical cord. In the preferred embodiment, two cannula systems may be connected to separate arteries, and one cannula system can be connected to a vein in the umbilical cord, thus forming a circulation loop, where blood leaves the neonate, moves into the cannula system, moves into a connected circulation circuit, and then returns to the neonate. In some aspects, if the cannulation process should be repeated, the cannula system is disengaged from the vessel and surrounding tissue and the cannula insertion system is reset (as explained in detail later). The cannula system can then be introduced to a different portion of the umbilical cord, and the initially used portion of the umbilical cord may be severed.

Continuing with the preferred embodiment, the cannula system may releasably engage with a cannula insertion device, which facilitates connecting and securing the cannula system to each respective blood vessel. The cannula insertion system may be handheld and designed to be operated by the user with the same hand that is holding it. Such one-handed operation allows the user the ability to use the second hand for other tasks. In general, in the preferred embodiment, the cannula insertion system can be configured to penetrate a targeted blood vessel, expand the opening in the vessel wall, connect the cannula system to the vessel (e.g., by inserting a portion of the cannula system into the blood vessel through the created opening), and securing the cannula system to the vessel. Once the necessary steps have been performed and the cannula system is secured to the vessel, the cannula insertion device may be disconnected from the cannula system.

Referring to FIGS. 1-7A, a cannula insertion system 10 includes a cannula insertion device 20. The cannula insertion device 20 has a housing 220 that defines a housing recess 222 therein (see FIGS. 7 and 7A). The recess 222 may receive a cannula system 28 therein. In some aspects, the housing 220 may define a transparent or translucent portion 230, through which the user may observe the movement of components and flow of blood through the cannula system 28. The transparent or translucent portion 230 includes a transparent or translucent portion to permit a user to view at least a portion of the housing recess 222.

A flashback chamber 231 (see FIG. 2) can be disposed in the recess 222 and visible through the transparent or translucent portion 230 and can be configured to provide information to a user of the cannula insertion device 20. For example, the cannula insertion device 20 can be configured to indicate successful entry of a needle into a blood vessel. Upon connection of the cannula insertion system with the vessel to be cannulated, liquid from the vessel (for example blood) can travel through the cannula insertion device 20 and into the flashback chamber 231. The flashback chamber 231 defines an opening 232, through which the blood may drip into the portion of the recess 222 that is visible through the transparent or translucent portion 230, thus indicating that the vessel has been successfully cannulated. In some aspects, before cannulating the vessel, the user may place a predetermined amount of liquid (e.g., saline) into the flashback chamber 231 through the opening 232 (e.g., by injecting the liquid). The cannula system may be primed with a suitable material before use (e.g., blood, saline, or known composition, such as PlasmaLyte). The blood moving through the flashback chamber 231 upon successful insertion of the needle can then expedite time for flashback with the liquid in the flashback chamber 231, and a droplet of the mixture can drip out of the opening 232. Visualization of the flashback serves as an indication the needle puncturing the vessel wall and entering the blood vessel. If blood does not drip from the flashback chamber 231, this may be an indication that, for example, the needle did not properly enter the vessel, the needle inadvertently punctured an opposing vessel wall and exited the vessel, and/or there is a mechanical blockage in the cannula insertion device 20. An elastomeric plug 233 may be removably positioned in the opening 232. The plug 233 may be moved away from the opening 232 when the cannula system is primed. After the needle has been retracted, the plug 233 is disposed in the opening 232 and prevents the fluid from exiting the needle lumen, thus decreasing blood loss. The plug may further serve as a physical barrier to prevent debris from entering the flashback chamber 231 through the opening 232.

The housing 220 can be sized such that the cannula insertion device 20 can be held in one hand by the user. It will be appreciated that the housing 220 need not fit entirely into the palm of the user's hand and can extend out of the hand in one or more directions (see, e.g., FIG. 23). The housing 220 extends between a distal end 221 and a proximal end 223 opposite the distal end 221. The housing 220 has a maximum length L extending along an axis parallel to D1 from the distal end 221 to the proximal end 223, a maximum width W extending along an axis perpendicular to the length L, and a maximum height H extending along an axis perpendicular to both the length L and the width W (see FIG. 3). In some aspects, the housing 220 may have a length L up to about 300 mm, up to about 250 mm, up to about 235 mm, up to about 200 mm, or up to another suitable length. In some aspects, the housing 220 may have a width W up to about 50 mm, up to about 40 mm, up to about 30 mm, or up to another suitable width. In some aspects, the housing 220 may have a height H up to about 50 mm, up to about 40 mm, up to about 30 mm, or up to another suitable height. In some specific embodiments, the housing 220 may have a length L of between about 150 mm to about 300 mm, preferably between about 175 mm to about 275 mm, and more preferably between about 175 mm to about 250 mm, a width W between about 20 mm to about 40 mm, preferably between about 25 mm to about 35 mm, and a height H between about 25 mm to about 35 mm, and in one embodiment a length L of about 200 mm, a width W of about 28 mm, and a height H of about 31 mm. It will be further appreciated that the housing 220 may have different or additional dimensions, and that the specific sizes and shapes thereof would depend on the intended use. The precise dimensions of the housing 220, as well as of the cannula insertion device 20 or the cannula insertion system 10 as a whole, can be selected to allow for single-handed use by the user. For example, the housing 220 can be sized in such a way that an average user can perform the anticipated discrete functions of the cannula insertion system (e.g., retracting the needle, retracting the dilator, and disengaging the cannula from the cannula insertion device) without substantially relocating the housing 220 in the hand between functions and, in some preferred embodiments, being able to perform all functions with the same digit (e.g., with the thumb of the hand holding the housing).

Figure 8:
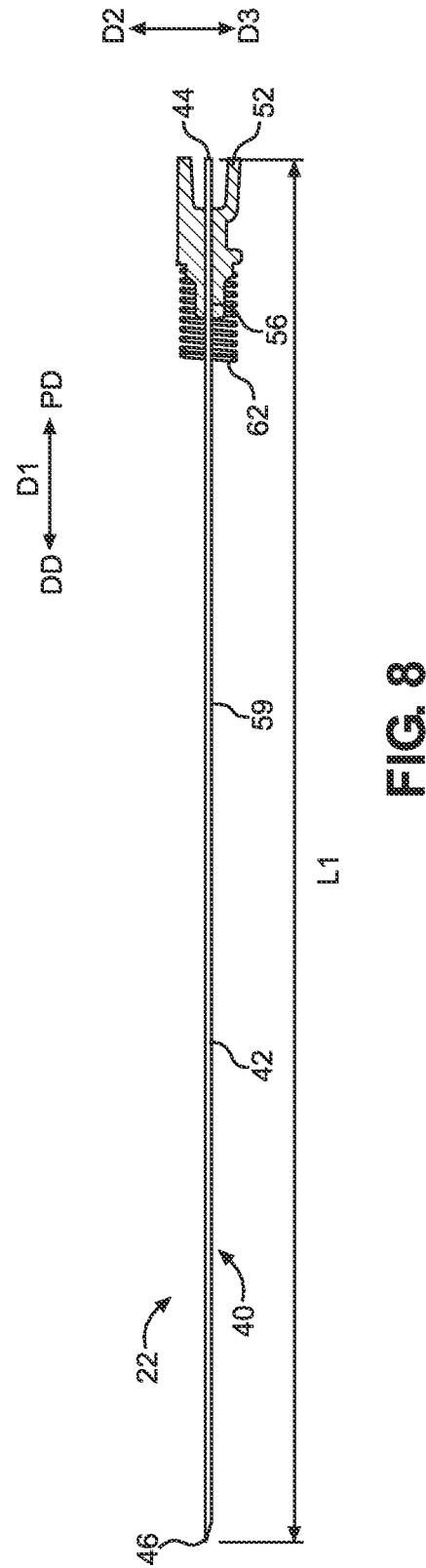
FIG. 8 is a side perspective view of a needle assembly according to an aspect of this disclosure.
Figure 9:
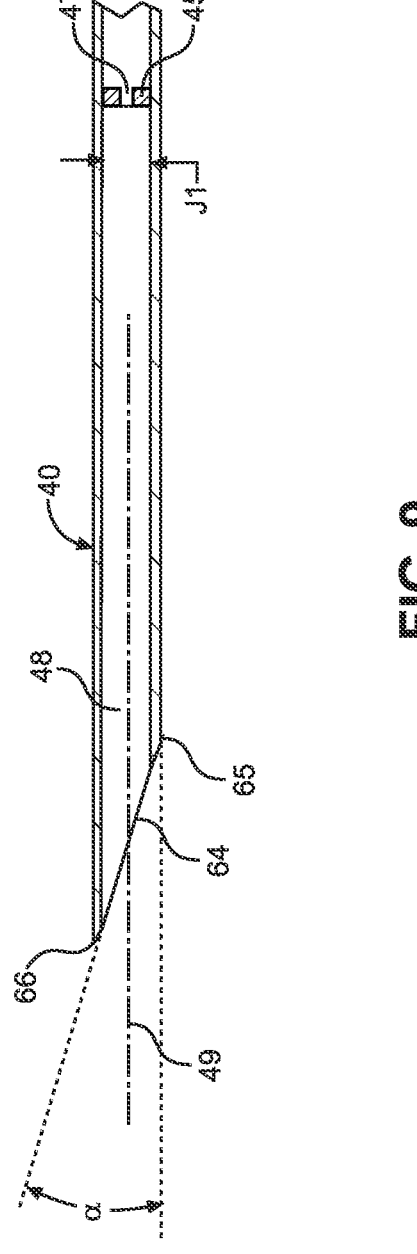
FIG. 9 is a side cross-sectional view of a portion of the needle assembly of FIG. 8.

Referring to FIGS. 8 and 9, the cannula insertion system 10 can include a needle assembly 22. The housing recess 222 can be configured to receive the needle assembly 22. The needle assembly 22 can include a needle 40, which is configured to pierce a vessel thereby creating a passage into the vessel. According to one aspect of the disclosure, the needle 40 can be configured to pierce and open a passage into a blood vessel, for example a blood vessel located in an umbilical cord of a neonate. The needle 40 can include a needle body 42 that extends from a proximal end 44 of the needle 40 to a distal end 46 of the needle 40. The proximal end 44 of the needle 40 can be spaced from the distal end 46 of the needle 40 in a proximal direction PD, and the distal end 46 can be spaced from the proximal end 44 of the needle 40 in a distal direction DD. As shown in the illustrated embodiment, the needle body 42 can be elongate along a first direction D1 extending from the proximal end 44 to the distal end 46 or vice versa. The first direction D1 is bidirectional, and can include both the proximal direction PD and the distal direction DD. The first direction D1 can be used for reference with other components of the cannula insertion system described throughout this specification.

The needle 40 defines a length L1 measured between the proximal end 44 and the distal end 46 of the needle 40. According to one embodiment, the length L1 can be between about 25 mm and about 305 mm. According to one embodiment, the length L1 can be between about 150 mm and about 180 mm, and preferably between about 100 mm and about 200 mm.

As shown in FIG. 9, the needle 40 can further include a needle lumen 48 defined by the needle body 42 and extending along the entirety of the length L1 between the proximal end 44 and the distal end 46. The needle lumen 48 may have a circular cross-section. The needle 40 can define a central axis 49, along which the needle lumen 48 extends. The central axis 49 can be parallel to the first direction D1. The needle 40 defines a gauge determined by a size of the needle lumen 48, specifically by a cross-sectional area J1 that is perpendicular to the first direction D1. The lumen 48 of the needle 40 can define a cross-sectional area between about 0.05 mm² and about 0.8 mm², or between about 0.2 mm² and about 0.45 mm². The needle 40 can be between a 20 gauge needle and a 25 gauge needle. According to another aspect, the needle 40 can be larger than a 20 gauge needle, for example, if the needle 40 is configured for use in vessels larger than vessels typically found in an umbilical cord. In some aspects, the needle 40 can be solid such that the needle 40 is devoid of a needle lumen 48. In some exemplary embodiments, the needle 40 may be a 20 gauge needle having an outer diameter of about 0.603 mm.

Referring still to FIG. 9, the needle 40 can include a bleedback reduction mechanism 45, configured to provide restriction to blood flow through the needle lumen 48, while still allowing some amount of blood flow, which can be used to identify when the needle 40 has entered a vessel. According to one embodiment, the needle 40 can include a micro hole 47, which is smaller than the needle lumen 48. The bleedback reduction mechanism 45 can be positioned in the needle lumen 48, for example in or near the distal end 46, in or near the proximal end 44, or between the distal end 46 and the proximal end 44. A portion of the bleedback reduction mechanism 45 can be positioned outside the needle lumen 48, for example around an exterior portion of the proximal end 44. In some exemplary embodiments, the bleedback reduction mechanism 45 may be in liquid communication with the flashback chamber 231, such that blood is configured to move through the needle 40, and specifically through the bleedback reduction mechanism 45, and into the flashback chamber 231. Liquid may pass through the micro hole 47 and into the flashback chamber 231 as described above. In one embodiment, the bleedback reduction mechanism 45 effectively reduces the inner diameter of the needle lumen 48. In some aspects, the bleedback reduction mechanism 45 can include a feature on the needle 40 configured to reduce the inside diameter of the needle lumen 48 locally to define the micro hole 47.

As shown in FIG. 9, the tip of needle 40 can include a bevel 64 having a base end 65 and a tip end 66. As the bevel 64 extends from the base end 65 to the tip end 66, the cross-sectional area J1 decreases. The needle 40 can define a bevel angle α measured from the central axis 49 to the bevel 64. According to one embodiment, the bevel angle α may be between about 1 degree and about 60 degrees. According to another embodiment, the bevel angle α may be between about 5 degrees and about 45 degrees. According to yet another embodiment, the bevel angle α can be between about 10 degrees and about 25 degrees. According to yet another embodiment, the bevel angle a can be between about 12 degrees and about 22 degrees. A smaller bevel angle α can result in easier piercing of a vessel and insertion of the needle 40, however decreasing the bevel angle α increases a length of the bevel 64 measured from the base end 65 to the tip end 66. According to one aspect of the disclosure, the needle 40 can include a plurality of bevels such that the bevel 64 is one of the plurality of bevels. The needle may be manufactured from a medical grade material, such as surgical stainless steel, for example SAE 316, 420, or 440 stainless steel.

According to one embodiment, a successful insertion of the needle 40 is achieved when both the tip end 66 and the base end 65 are positioned within the vessel. An increase in the length of the bevel 64 can result in a greater insertion depth of the needle 40 needed to achieve a successful insertion, which may result in a higher likelihood of "backwalling" or piercing the far side of the vessel. Thus, according to one embodiment, the needle 40 is configured to balance ease of insertion into an umbilical cord, while maintaining an insertion depth that minimizes the chance of backwalling the umbilical cord.

Referring again to FIGS. 1-7A, as shown in one aspect, the cannula insertion device 20 includes a mechanism to translate the needle 40 relative to the housing 220. A needle actuator 50 is connected to or disposed on the housing 220 (see, specifically, FIGS. 6-7). In some aspects, the needle actuator 50 is movable within the recess 222. The needle actuator 50 is operably coupled to the needle assembly 22 (see FIG. 8) such that actuation of the needle actuator 50 transitions the needle 40 from a first position to a second position. Referring to FIGS. 4-7, the needle actuator 50 is affixed to a hub 52 and a boom arm 54 disposed between the needle actuator 50 and the hub 52. The hub 52 can include a recess 56 configured to receive the needle 40. The recess 56 defines a shape that corresponds to an outer surface 59 of the needle body 42. The needle assembly 22 can be configured such that the needle 40 is permanently or temporarily secured to the hub 52. For example, the needle 40 and the hub 52 can be secured with adhesive, overmolding, welding, corresponding threads, etc.

According to one embodiment, the needle 40 and the needle actuator 50 are configured to be secured such that movement, including translation, rotation, or both, of the needle 40 relative to the hub 52 is prevented without plastic deformation of the needle assembly 22.

Figures 6, 6A:
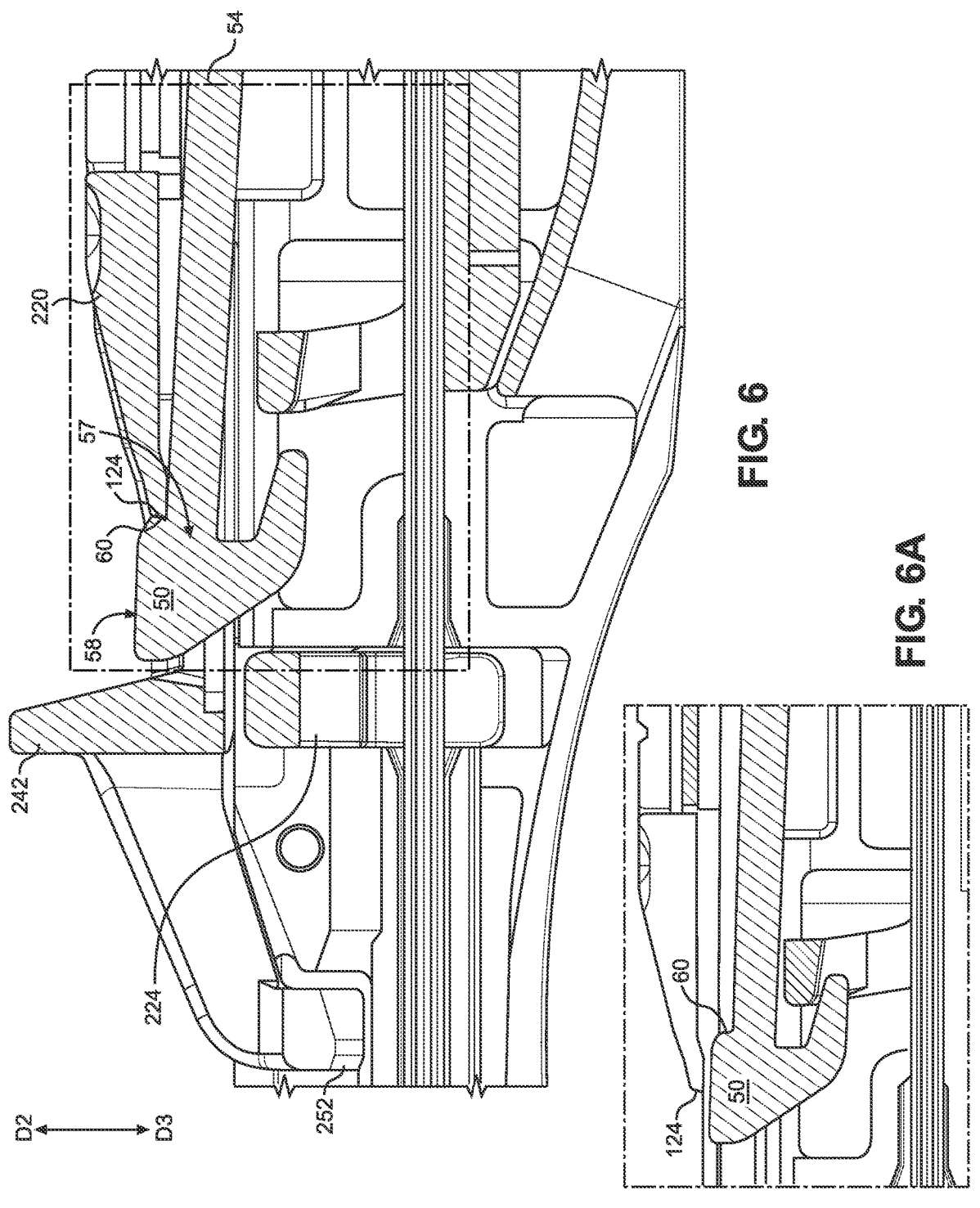
FIG. 6 is a close-up cross-sectional view of portion B of the cannula insertion device of FIGS. 3-5.
FIG. 6A is a close-up cross-sectional view of the portion of FIG. 6 but depicting the actuator spaced apart from the blocking surface.
Figure 7:
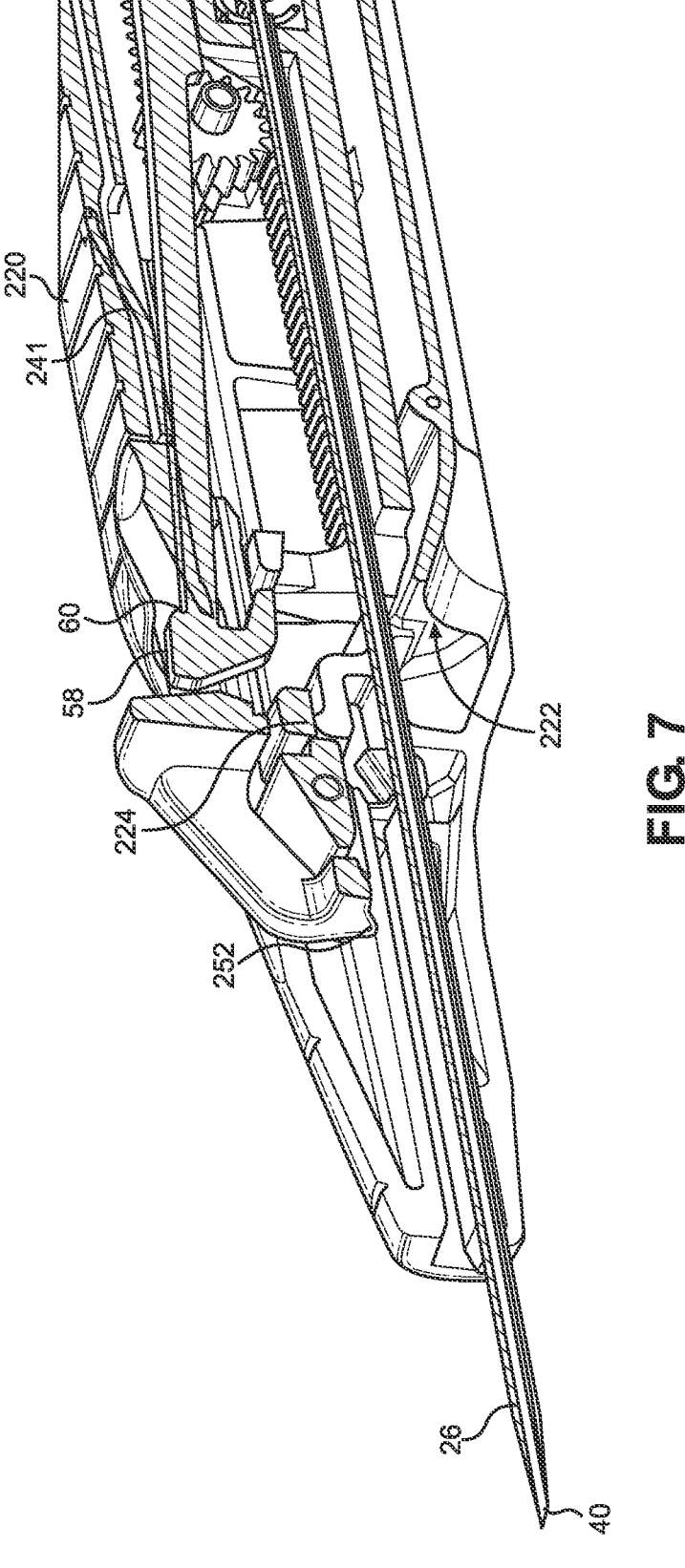
FIG. 7 is an isometric cross-sectional view of another portion of the cannula insertion device of FIGS. 3-6A.
Figure 7A:
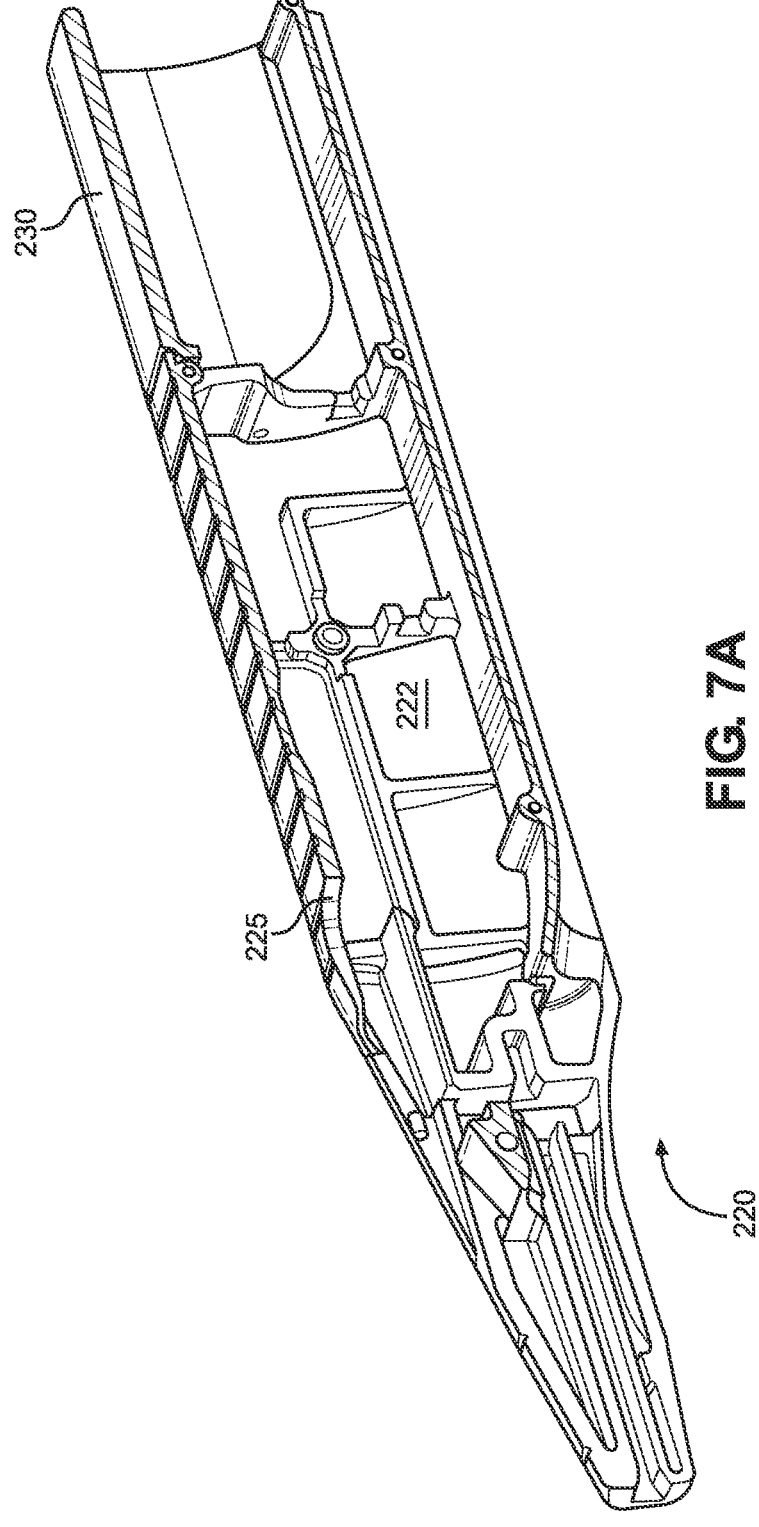
FIG. 7A is a cross-sectional view of the housing of the cannula insertion device of FIGS. 3-7.

The boom arm 54 extends from the hub 52 to the needle actuator 50, for example at least partially in the distal direction DD, as shown in the illustrated embodiment. The boom arm 54 can include a proximal end 55 adjacent to the hub 52 and a distal end 57 opposite the proximal end 55 and positioned such that the boom arm 54 terminates at the distal end 57 at the needle actuator 50. The needle actuator 50 can include an actuation surface 58 configured to be contacted by the user. As shown in FIG. 6, the actuation surface 58 can face in the second direction D2. In other aspects, the actuation surface 58 can be oblique or normal to the second direction D2. The user can push on the actuation surface 58, for example with a finger or a thumb, to cause the needle actuator 50 to move the needle 40.

As seen in FIGS. 6 and 6A, the needle actuator 50 can include a stop surface 60, for example positioned adjacent the distal end 57. According to one embodiment, the stop surface 60 faces in the proximal direction PD. The stop surface 60 is configured to selectively abut another surface of the cannula insertion device 20, for example, a blocking surface 124 defined by the housing 220. FIG. 6 shows the stop surface 60 abutting the blocking surface 124, while FIG. 6A shows the stop surface 60 spaced away from the blocking surface 124.

Figures 5, 5A:
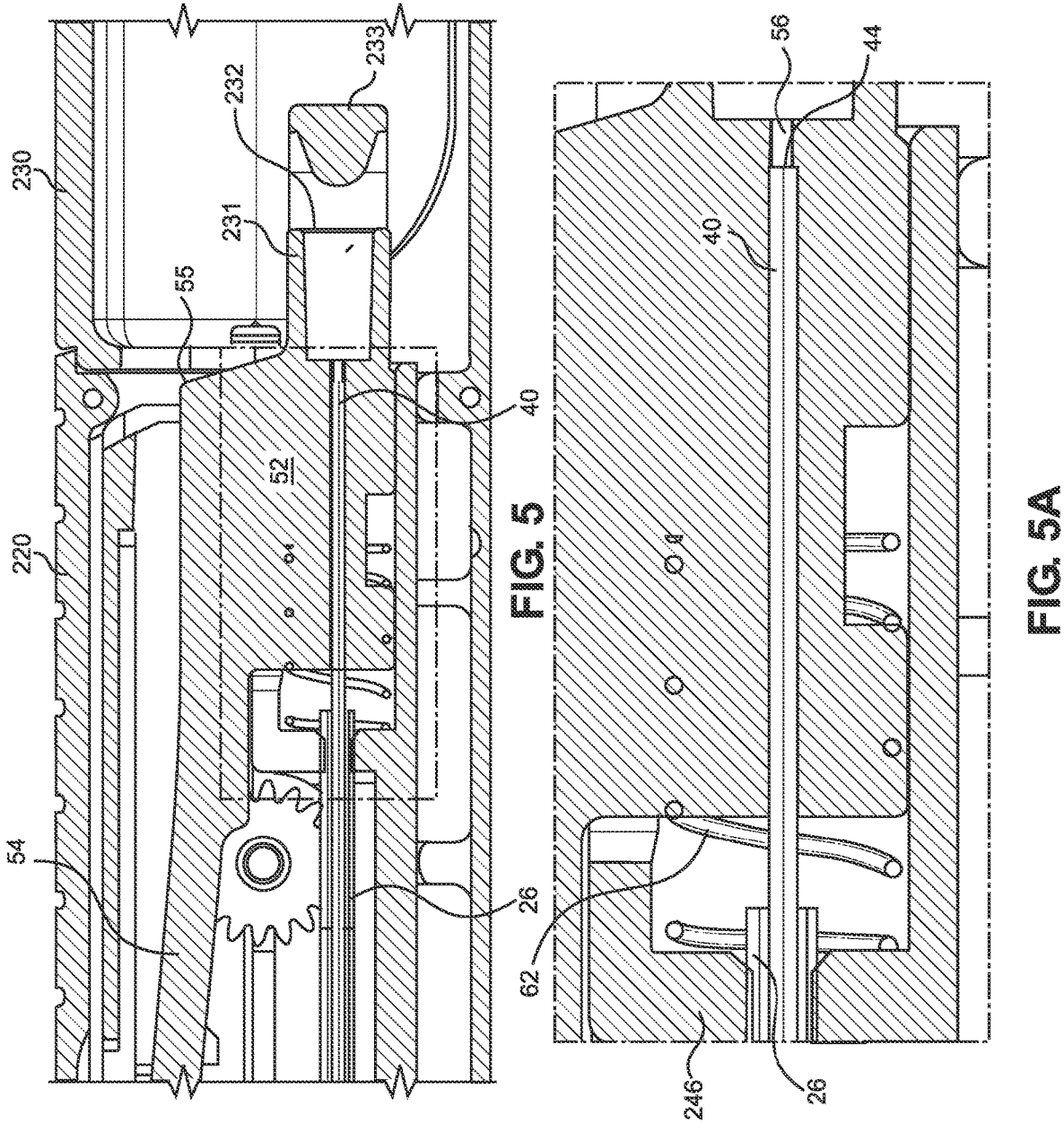
FIG. 5 is close-up cross-sectional view of portion A of the cannula insertion device of FIGS. 3 and 4.
FIG. 5A is a close-up cross-sectional view of a portion of the cannula insertion device depicted in FIG. 5.

The needle assembly 22 can further include a biasing member 62, for example a spring or a resilient elastic (see FIGS. 5 and 5A). The biasing member 62 is configured to apply a biasing force on the needle assembly 22. According to one embodiment, the biasing member 62 is configured to apply a force on the hub 52 in the proximal direction PD.

The needle assembly 22 may have a loaded and an unloaded configuration. In the loaded configuration, the needle 40 is in a first position, and the biasing member 62 is exerting a biasing force on the hub 52 in the proximal direction PD. The boom arm 54 may be held in place against the biasing force by the contact between the stop surface 60 and the blocking surface 124, which serves as a physical stop to prevent the needle assembly 22 from being moved by the biasing member 62 (see FIGS. 6 and 6A). It will be appreciated that the force exerted by the biasing member 62 is sufficient to move the needle assembly 22 when there is no resistance to this movement, but insufficient to cause deformation or damage to either the boom arm 54, the hub 52, the needle 40, or the housing 220 when the biasing force is kept static due to the engagement of the stop surface 60 and the blocking surface 124.

In the unloaded configuration, the stop surface 60 is not in contact with the blocking surface 124, and the needle assembly 22 is positioned more proximally than when it is in the loaded configuration. To transition the needle assembly 22 from the unloaded configuration to the loaded configuration, the needle assembly 22 is moved in the distal direction DD against the biasing force exerted by the biasing member 62 onto the needle assembly 22 as explained below. The transition may be actuated manually by the user. The user may apply a force onto the needle assembly 22 (for example, at the flashback chamber 231) and push the needle assembly 22 in the distal direction DD. In some aspects, the housing 220 may be open at the proximal end 221, such that a user can insert a finger or thumb into the housing 220 to contact the flashback chamber 231. It will be appreciated that the force applied by the user should be greater than the biasing force exerted by the biasing member 62. In some aspects, the user can apply the loading force by pressing on the flashback chamber 231 in the distal direction DD. When the needle assembly 22 is in the loaded configuration, the user may hear an audible click that indicates successful transition of the needle assembly 22 from the unloaded configuration to the loaded configuration.

In the loaded configuration, the needle assembly 22 is configured such that as the user contacts (e.g., pushes on) the actuation surface 58, the distal end 57 of the needle actuator 50 moves relative to the hub 52. This movement may cause the boom arm 54 to elastically deform. As shown, for example, in FIGS. 18A and 18B, the user input can include an activation force F applied to the actuation surface 58 in a third direction D3. The third direction D3 can be opposite the second direction D2, normal to the actuation surface 58, both, or neither. The boom arm 54 may be moved by applying a force to the actuation surface 58, for example in the third direction D3, such that the stop surface 60 disengages from the blocking surface 124. Without this engagement, the biasing force causes needle assembly 22 to move in the proximal direction PD. The needle 40 is at a first position within the cannula insertion device 20 when the stop surface 60 and the blocking surface 124 are engaged (FIGS. 18A and 18D) and in a second position when the stop surface 60 and the blocking surface 124 are not engaged and the biasing force exerted by the biasing member 62 on the hub 52 has caused the needle assembly 22 to move in the proximal direction PD such that the stop surface 60 is located proximally to the blocking surface 124 (FIGS. 18B and 18E).

Figure 10:
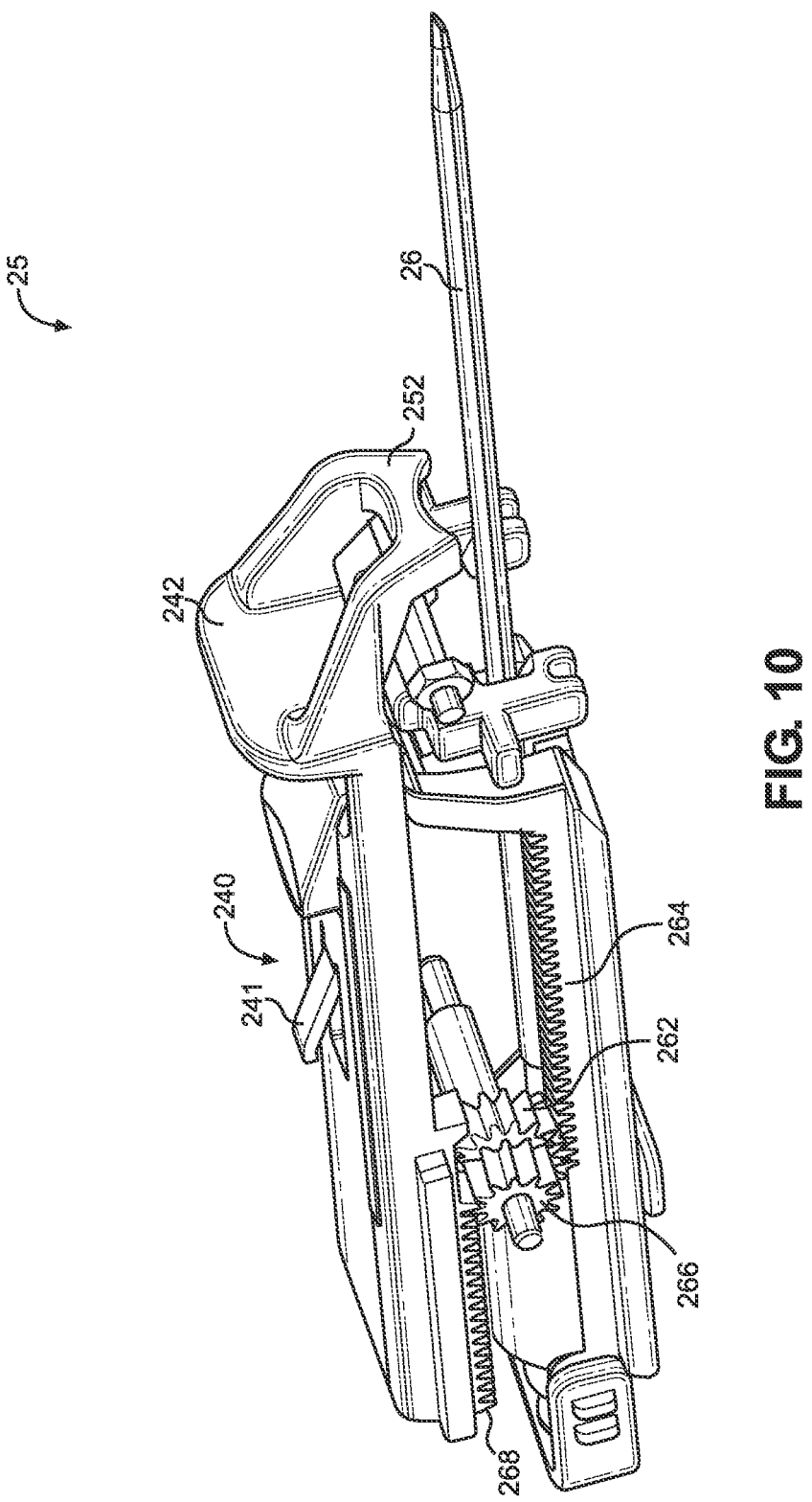
FIG. 10 is an isometric view of a dilator assembly according to an aspect of this disclosure.
Figure 11:
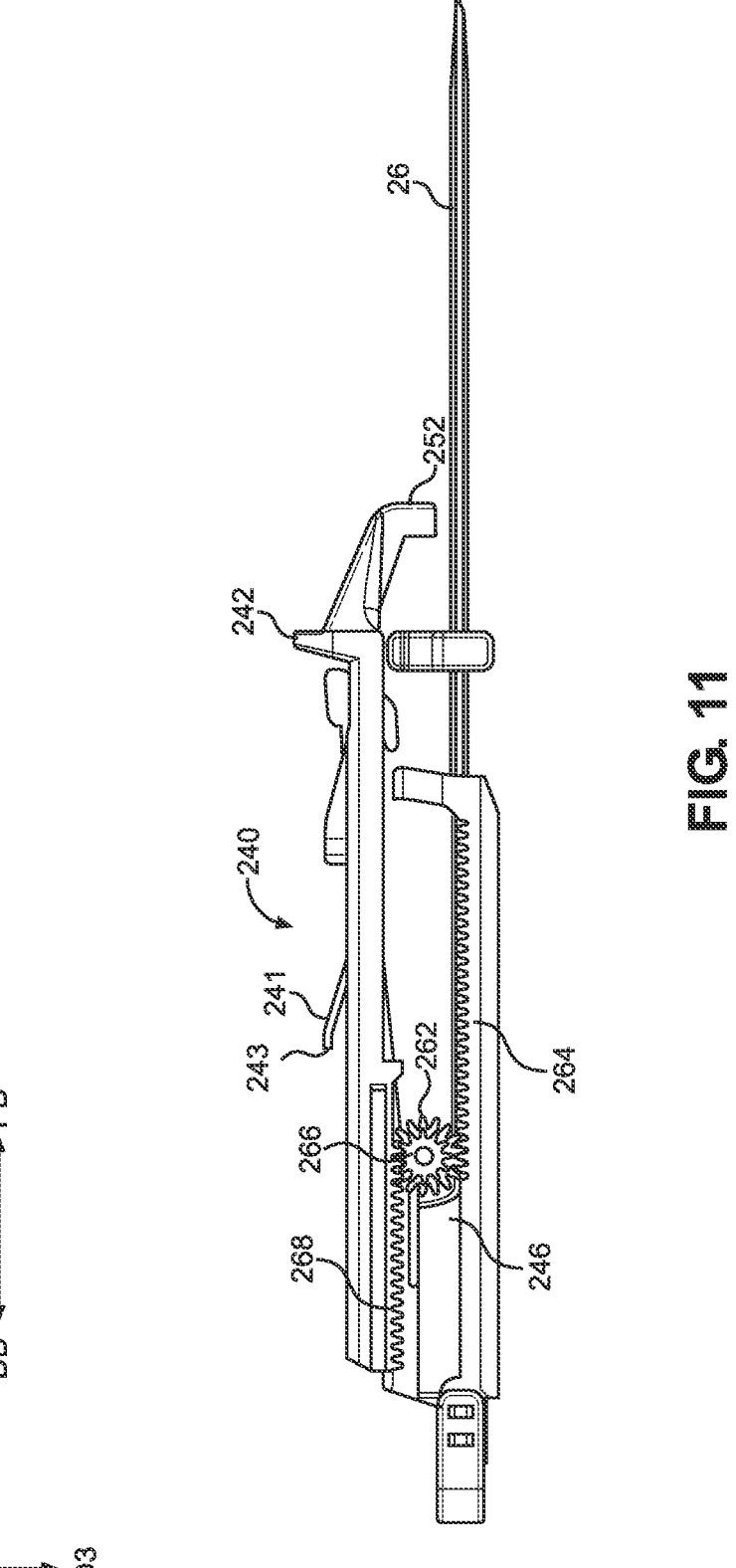
FIG. 11 is a side perspective view of the dilator assembly of FIG. 10.
Figure 12:
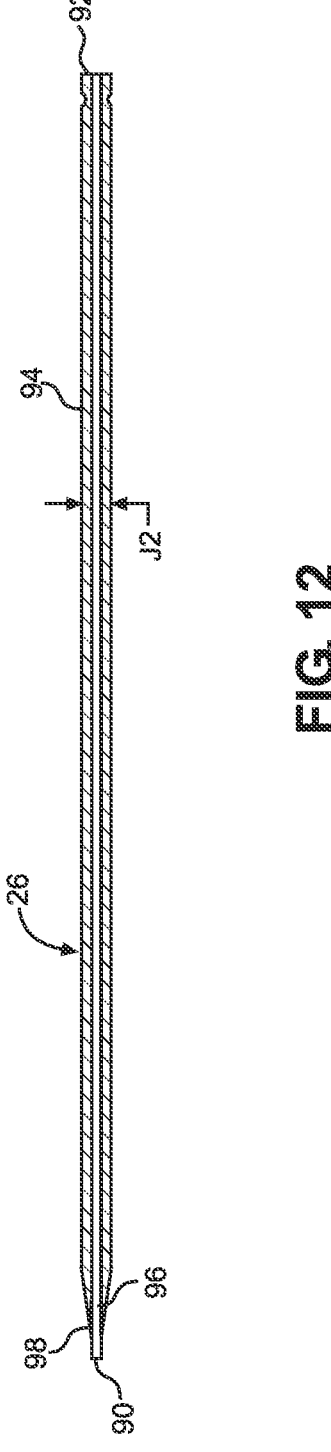
FIG. 12 is a side cross-sectional view of a dilator according to an aspect of this disclosure.

Referring to FIGS. 10-12, the cannula insertion system can further include a dilator assembly 25. In one embodiment, the dilator assembly 25 functions to house the needle 40 and create a larger opening in the blood vessel after the end of the needle pierces the wall of the blood vessel. Expanding the opening in the blood vessel can help insert a cannula into the vessel, as explained further below. The dilator assembly 25 includes a dilator 26, a dilator hub 246 configured to fixedly retain the dilator 26 therein, and a dilator movement mechanism 240. Referring specifically to FIG. 12, the dilator 26 may include a distal end 90, a proximal end 92, and a dilator body 94 that extends from the proximal end 92 to the distal end 90. The dilator 26 further includes a dilator lumen 96 defined by the dilator body 94. As shown in the illustrated embodiment, the dilator lumen 96 can extend through the entirety of the dilator body 94 between the proximal end 92 and the distal end 90. The dilator lumen 96 has a slightly larger cross-sectional area than the outer surface area of the needle 40 and is configured to receive the needle 40 therein. The needle 40 is slidably movable within the dilator lumen 96 and can extend, at least in part, out of the dilator lumen 96 at the distal end 90, out of the dilator lumen 96 at the proximal end 92, or out of both ends of the dilator lumen 96. In some aspects, the needle 40 may be longer than the dilator 26.

Figure 12A:
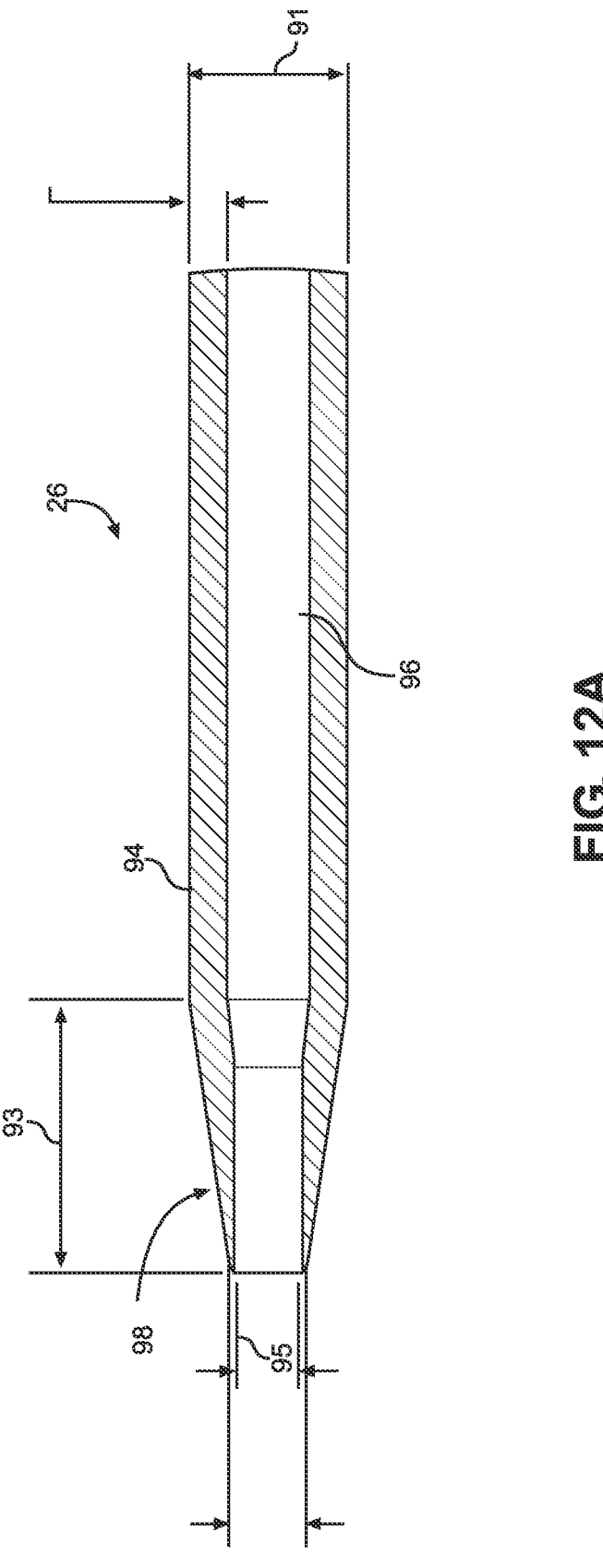
FIG. 12A is a side cross-sectional view of a dilator according to an aspect of this disclosure.

The dilator body 94 can define a tapered portion 98 adjacent the distal end 90. The dilator 26 can define an outer cross-sectional area J2, which decreases as the tapered portion 98 extends in the distal direction DD. As shown in the illustrated embodiment, the minimum cross-sectional area J2 of the tapered portion 98 can be located at the distal end 90 of the dilator 26. In some aspects, the dilator 26 may have an outer diameter 91 of between about 2 mm and about 6 mm. In some exemplary aspects (see FIG. 12B), the dilator 26 may have an outer diameter 91 of between about 4 mm and about 5 mm. In other exemplary aspects (see FIG. 12A), the dilator 26 may have an outer diameter 91 of between about 2 mm and about 3 mm. It will be appreciated that the specific sizes of the dilator 26 will depend on the intended use with the cannula insertion system 10. In some aspects, the specific dilator 26 that will be used will depend on the vasculature of the umbilical cord.

The tapered portion 98 may have a specific length 93 measured from the distal end 90 to the beginning of the taper located at the position on the dilator body 94 where the outer cross-sectional area J2 begins to decrease relative to outer cross-sectional area J2 of the rest of the dilator body 94. In some aspects, the length 93 of the tapered portion 98 may be between about 1 mm and about 12 mm, between about 2 mm and about 11 mm, between about 3 mm and about 10 mm, between about 4 mm and about 9 mm, or another suitable length. In some exemplary aspects (see FIG. 12A), the length 93 of the tapered portion 98 may be about 4 mm. In other exemplary aspects (see FIG. 12B), the length 93 of the tapered portion 98 may be about 9 mm.

The tapered portion 98 may have an inner diameter 95 that is different from the inner diameter of the rest of the dilator body 94 not at the tapered portion 98 or, alternatively, the inner diameter 95 may be the same throughout the entire dilator body 94, including the tapered portion 98. In some exemplary aspects, the inner diameter 95 of the tapered portion 98 may be between about 0.5 mm and about 2 mm. In some specific exemplary embodiments, the inner diameter 95 of the tapered portion 98 may be about 0.96 mm.

The dilator 26 may be sized and shaped according to a particular aspect described above based on its intended application in the cannula insertion system 10. Since the cannula insertion system 10 can be utilized to cannulate an arterial vessel or a venous vessel, different parameters of the dilator 26 may be preferable. For example, in aspects where the cannula insertion system 10 will be used to cannulate an arterial vessel, it may be preferable to utilize a smaller dilator than the dilator used for cannulating a venous vessel. In some aspects, when the cannula insertion system 10 is intended to cannulate an arterial vessel, the dilator 26 may have a tapered portion 98 having a length 93 of about 4 mm (see, e.g., FIG. 12A). The dilator 26 may be between about 3 Fr and about 17 Fr, between about 5 Fr and about 15 Fr, or in another suitable size range. The dilator size may be determined relative to the size of the cannula 104. In some aspects, the dilator can be 3, 4, 5, . . . , 17 Fr or another suitable size. In some exemplary aspects, where the cannula insertion system 10 is intended to cannulate an arterial vessel, the dilator 26 may be between about 4 Fr and about 11 Fr. In other aspects, where the cannula insertion system

Figure 12B:
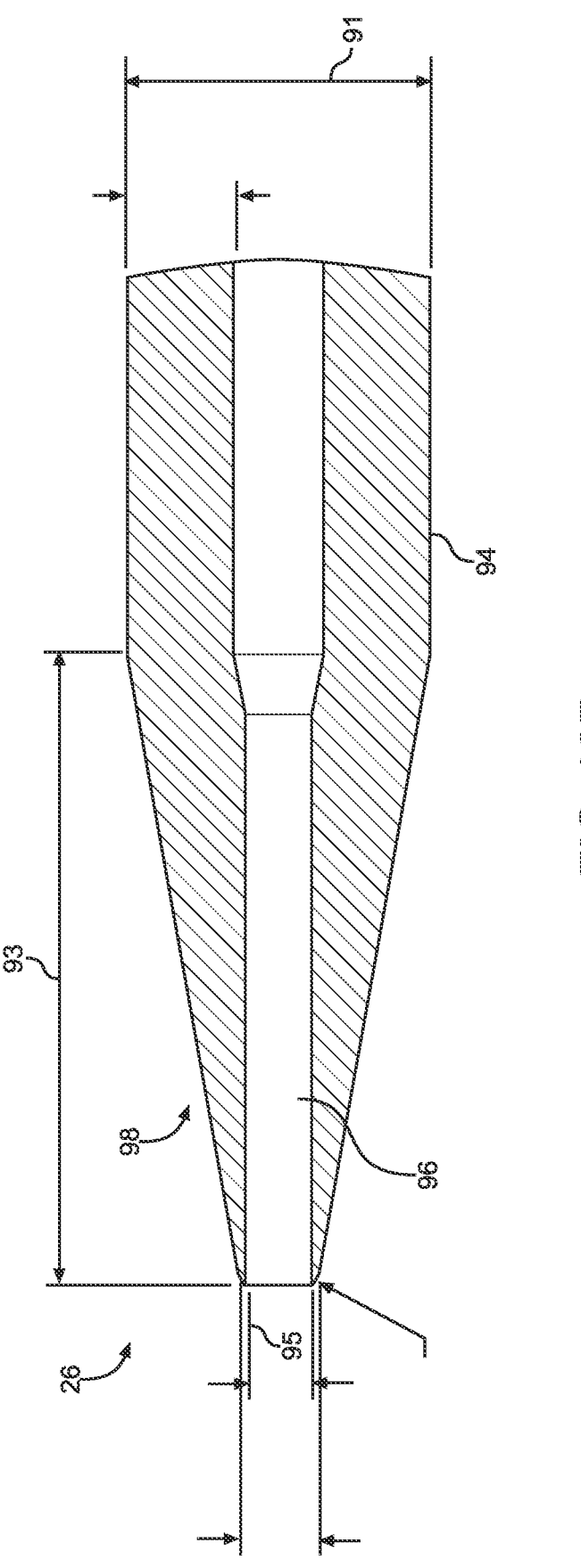
FIG. 12B is a side cross-sectional view of a dilator according to another aspect of the disclosure.

10 is intended to cannulate a venous vessel, the dilator 26 may have a tapered portion 98 having a length 93 of about 9 mm (see, e.g., FIG. 12B). The dilator 26 in these examples can be between about 9 Fr and about 17 Fr. The difference in dilator tip sizes and geometry allows for the desired ease of entry of the dilator into the vessel and for reduced risk of unintended piercing of the opposing vessel wall.

Referring to FIGS. 10 and 11, the dilator 26 may be translated by the dilator movement mechanism 240, which includes a dilator actuator 242 disposed on or within the housing 220. When the dilator actuator 242 is moved in a first direction, the dilator hub 246 and the dilator 26 therein are moved towards the vessel that is to be cannulated, for example in the distal direction DD. When the dilator actuator 242 is moved in a second, opposite direction, the dilator hub 246 and the dilator 26 therein are moved away from the vessel, for example in the proximal direction PD. In some aspects, movement of the dilator actuator 242 results in movement of the dilator hub 246 and the dilator 26 in the opposite direction, for example, where moving the dilator actuator 242 in the distal direction DD causes the dilator 26 to move in the proximal direction PD, and moving the dilator actuator 242 in the proximal direction PD causes the dilator 26 to move in the distal direction DD.

In some aspects, the dilator movement mechanism 240 further includes a rack and pinion gear system 260 that is disposed in the housing 220 and is configured to engage and operate with the dilator hub 246. A first pinion 262 is disposed on the housing 220 and is rotatable along its axis. The first pinion 262 engages with a first rack 264 and is configured to cause the first rack 264 to move along the first direction D1. A second pinion 266 is disposed on the housing 220 and is rotatable along its axis. The second pinion 266 is engaged with a second rack 268 and is configured to cause the second rack 268 to move along the first direction D1. In some aspects, the first pinion 262 may be affixed to the second pinion 266, such that when the when one of the pinions rotate, the other pinion also rotates. It will be appreciated that the rack and pinion gear system 260 may include a single pinion that engages with both racks, or, alternatively, may include more than two pinions and more than two racks.

Referring to FIGS. 18A-18F, the position of the dilator 26 along the first direction D1 may be controlled by movement of the dilator actuator 242, for example also along the first direction D1. When the dilator actuator 242 is in a first position, for example its most proximal position, the dilator 26 is in its extended configuration, for example, its most distal position (FIGS. 18A and 18B). As the dilator actuator 242 is moved in the distal direction DD, the rack and pinion gear system 260 in the dilator movement mechanism 240 described above may cause the dilator 26 to move in the proximal direction PD (FIGS. 18C and 18F). Movement of the dilator hub 246 and the dilator 26 may also cause movement of the needle assembly 22 (with the needle) in the proximal direction PD (FIGS. 18C and 18F). As best seen in FIGS. 5 and 5A, the needle hub 52 may contact the dilator hub 246 in such a way that when the dilator hub 246 moves in the distal direction DD or in the proximal direction PD, the needle hub 52 also moves in the same respective direction. As shown in FIG. 18C, for example, both the dilator hub 246 and the needle hub 52 are more proximal to their respective positions in FIG. 18B.

Figure 11A:
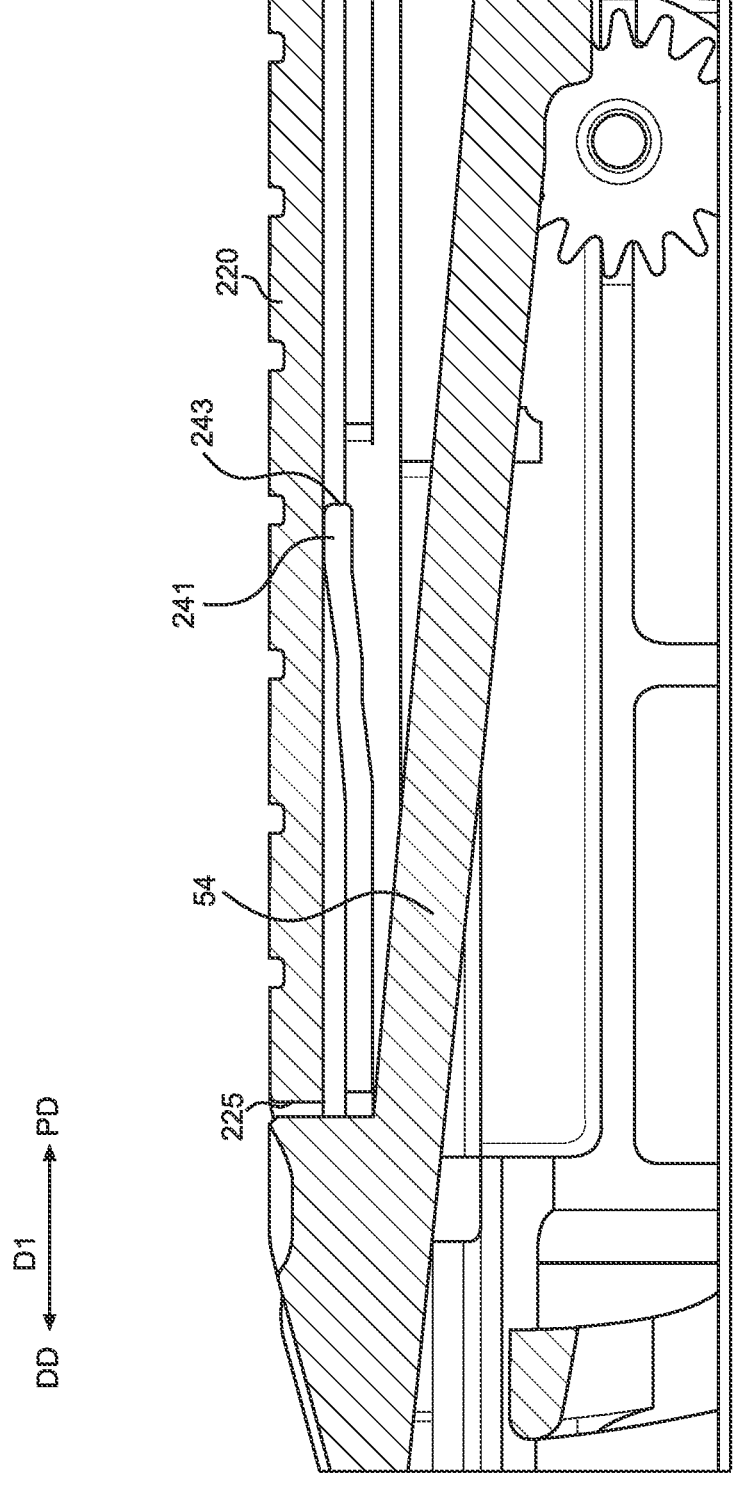
FIG. 11A is a side cross-sectional view of a portion of the cannula insertion device showing a retention member inside the housing.
Figure 11B:
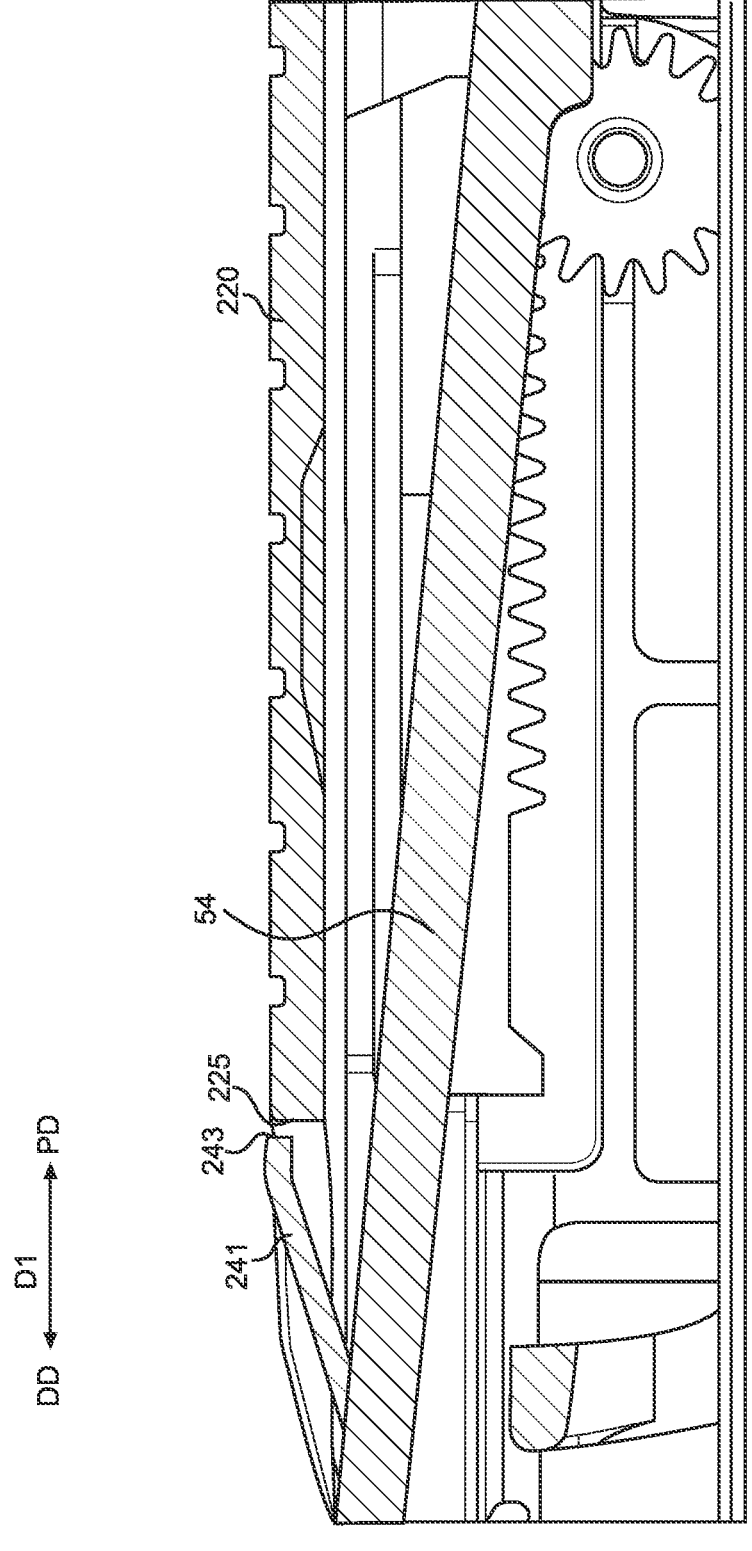
FIG. 11B is a side cross-sectional view of the portion of FIG. 11A showing the retention member in line with a dilator assembly blocking surface on the housing.

As shown in FIGS. 10-11B, the dilator assembly 25 may include a retention member 241 disposed thereon, for example on the dilator movement mechanism 240. The retention member 241 is elastically deformable, for example in the second or third directions D2, D3. Referring to FIGS. 11A and 11B, the retention member 241 is configured to releasably engage with a corresponding dilator assembly blocking surface 225 defined on the housing 220 to prevent inadvertent movement of the dilator assembly 25. The retention member 241 defines a retention surface 243 that is configured to contact the dilator assembly blocking surface 225. For example, when the dilator assembly 25 is disposed such that the dilator 26 is in its extended configuration (such as FIGS. 18A and 18B), the retention member 241 is inside the housing 220, for example in the recess 222, such that the retention surface 243 is not in contact with the housing 220 (see FIG. 11A). When the dilator assembly 25 is moved such that the dilator 26 is in its retracted configuration (such as in FIG. 18C), the retention member 241 is moved outside of the recess 220 such that the retention surface 243 is positioned in line with the dilator assembly blocking surface 225 along the first direction D1 (see FIG. 11B). If the user attempts to move the dilator actuator 242 backwards in the opposite direction after the dilator 26 has been retracted, the retention surface 243 contacts the dilator assembly blocking surface 225 and precludes such movement. This prevents inadvertent extension of the dilator 26 after the dilator 26 has already been retracted. If such movement is still desired, or if the cannulation process is complete, the dilator assembly 25 may be moved back to its original position where the dilator 26 is extended by simultaneously moving the dilator actuator 242 in the proximal direction PD and applying a force on the retention member 241 in the third direction D3 (e.g., pressing down) such that the retention surface 243 is no longer in line with the dilator assembly blocking surface 225 along the first direction D1.

The cannula insertion system 10 can further include a cannula system 28 that is configured to fluidly connect to the vessel to be cannulated at one end and to a circulation system at another end. Referring to FIGS. 13-17A, the cannula system 28 can include a cannula 104 that has a distal end 100 a proximal end 102 opposite the distal end 100. The cannula 104 includes a cannula lumen 106 defined by the cannula 104. As shown in the illustrated embodiment, the cannula lumen 106 can enter the cannula 104 at one of the proximal end 102 and the distal end 100, extend through an entirety of the cannula 104, and exit the cannula 104 at the other of the proximal end 102 and the distal end 100.

The cannula 104 can define a tapered portion 108 adjacent the distal end 100. The cannula system 28 can define a cross-sectional area J3 (see FIG. 17), which decreases as the tapered portion 108 extends in the distal direction DD. The minimum cross-sectional area J3 of the tapered portion 108 can be located at the distal end 100 of the cannula system 28.

The cannula 104 can define a reinforced portion 110 that is configured to be resistant to deformation. The reinforced portion 110 may be adjacent to the distal end 100. The reinforced portion 110 may include a component that is configured to resist stretching, for example a polyethylene wire or thread or a stainless steel wire. This prevents the reinforced portion 110 from stretching when the cannula 104 is being inserted into the vessel and the clamping mechanism is activated to secure the vessel to the cannula system 28. The reinforced portion 110 may be a portion of the cannula 104 or may comprise the entirety of the cannula 104 between the distal end 100 and the proximal end 102. The reinforced portion 110 may include one or more materials that resist stretching, such as nitinol, stainless steel, polyaramid synthetic mesh, such as KEVLAR® (available from E.I. Du Pont de Nemours and Company of Wilmington, Delaware), high-modulus polyethylene (e.g., DYNEEMA®), or other suitable materials. In this way, the cannula 104 may be less flexible nearer its distal end 100 to provide increased rigidity near the vessel, and thus, in one embodiment, the distal 25%, more preferably 50% of the cannula 104, is less flexible than the remaining proximal portion of the cannula 104.

In some embodiments, the dilator 26 and the cannula 104 may be a single component having a tapered distal end. The inside diameter of the tapered distal end may be approximately the same as, or nominally greater than, the outside diameter of needle body 42, such that the needle body 42 can be disposed therein. The tapered distal end of the combined dilator and cannula component in such embodiments may be configured to be deformable such that the tapered end can be expanded to produce a near-constant inside diameter bore along its length when the combined dilator and canula component is placed within the vessel. It will be appreciated that the combined component may provide comparable functionality to the functionality of separate dilators 26 and cannulas 104 as described throughout this application.

Figure 14:
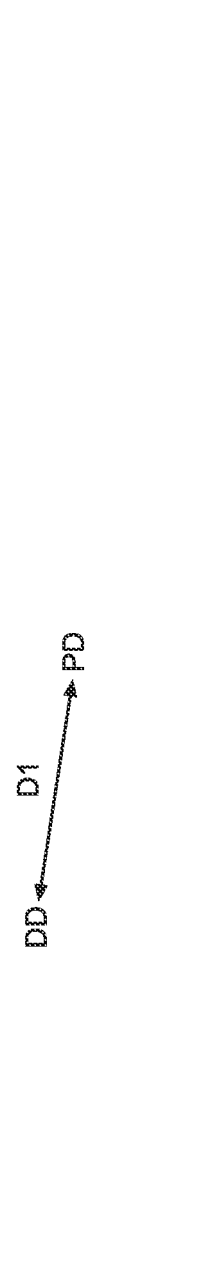
FIG. 14 is a side cross-sectional view of the cannula system of FIG. 13.
Figure 14:
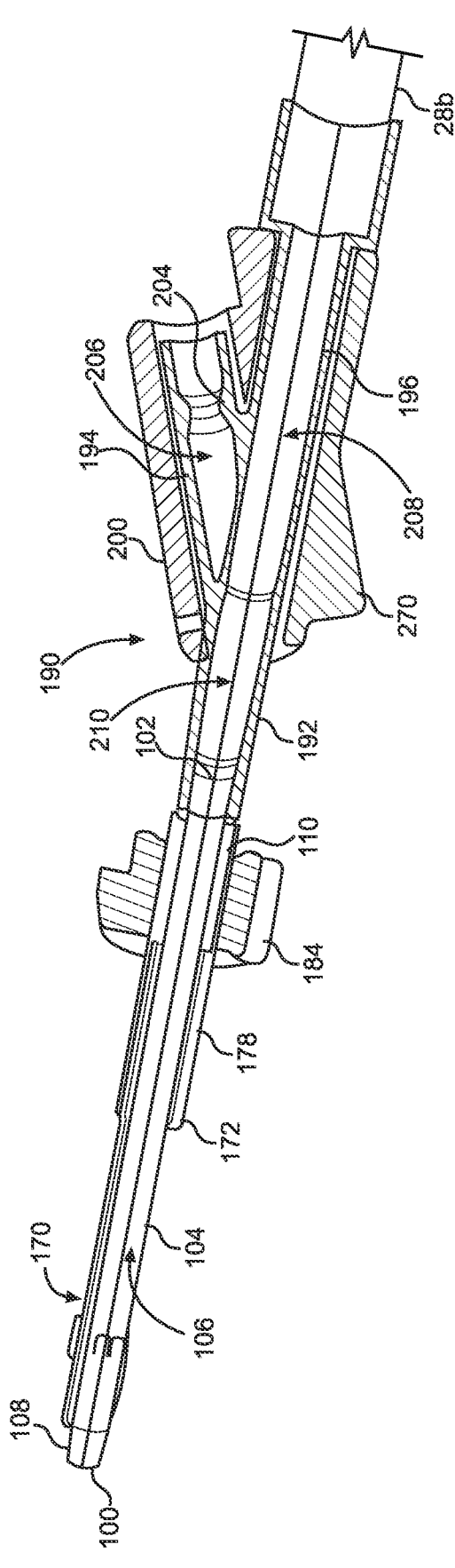

The cannula system 28 may include a Y-connector 190 configured to connect to the cannula 104. The Y-connector divides the cannula system 28 into two proximal portions. A first proximal portion 194 defines a first proximal channel 206 extending therethrough and is configured to interface and connect with the cannula insertion device 20. A second proximal portion 196 defines a second proximal channel 208 extending therethrough and is configured to connect to one or more components of an external circulation circuit 400 (see FIG. 25), for example an extracorporeal membrane oxygenation (ECMO) system. The second proximal portion 196 may connect to a tube 28b, which can then connect to the external circulation circuit 400. A distal portion 192 of the Y-connector 190 defines a distal channel 210 and is disposed opposite the first and second proximal portions 194, 196 and communicates with the cannula 104, for example at the proximal end 102. The distal channel 210 is in fluid communication with the cannula lumen 106 and with the second proximal channel 208. Fluid communication between the distal channel 210 and the first proximal channel 206 is reversible and may be opened or closed during using. Although FIG. 14 depicts an embodiment in which the second proximal channel 208 is coaxial with the cannula lumen 106, other embodiments can place the first proximal channel 206 to coaxial with the cannula lumen 106. Also, the needle 40 and dilator 26 can be sufficiently flexible (e.g., resiliently flexible) to bend to follow an insertion path from first proximal channel 206 to cannula lumen 106.

The Y-connector 190 may be a separate component from the cannula 104 or, in some aspects, the Y-connector 190 and the cannula 104 may be formed as a monolithic unitary piece. Utilizing a Y-shaped connector allows for the needle 40 and the dilator 26 to be introduced through a first channel, while the liquid (e.g., blood) from the cannulated vessel is moved through a different channel. This prevents blood loss, leaks, infections, or damage to the cannula system 28 or any connected tubing. It also creates an easier transition between the cannulation process and having the blood flow through the cannula and allows for at least a portion of the assembly to be connected to an external flow circuit during the cannulation process. In some aspects, at least a part of the Y-connector 190 may include the reinforced portion 110.

In some aspects, the entire cannula 104, the Y-connector 190, and the tube 28b may all be a single unitary piece that has been molded (e.g., dip molded) as one component. Such unitary construction could be beneficial to blood health by removing transitions along the blood flow path, thus decreasing instances of clot formation, leakage, or bacterial growth sites. The Y-connector 190 can include one or more materials that resist stretching, such as nitinol, stainless steel, poly-aramid synthetic mesh, such as KEVLAR® (available from E.I. Du Pont de Nemours and Company of Wilmington, Delaware), high-modulus polyethylene (e.g., DYNEEMA®), or other suitable materials. Specifically, in some aspects, the distal portion 192 may include the stretch-resistant materials listed above, while the first and second proximal portions 194, 196 may be devoid of the stretch-resistant materials.

The first proximal portion 194 defines a seal 198 (see FIG. 15) through which the needle 40 and/or the dilator 26 may removably pass when the cannula insertion device 20 is engaged with the cannula system 28. It will be appreciated that the seal 198 is configured to be reversibly opened to allow the needle 40 and the dilator 26 to pass through while also being configured to be closed when the needle 40 and dilator 26 are removed from the cannula system 28. The seal 198 may include a resilient or elastic material that is configured to deform in response to the forces of the needle 40 or dilator 26 and to return to its undeformed state when the needle 40 or dilator 26 are removed. The seal 198 should be manufactured such that liquid in the cannula is precluded from passing therethrough when the seal 198 is closed. When the seal 198 is open, the distal channel 210 may fluidly communicate with both, the first proximal channel 206 and the second proximal channel 208. When the seal 198 is closed, the distal channel 210 may only communicate with the second proximal channel 208. In some embodiments the seal 198 may be a slit seal 198 in the wall of the Y-connector 190 within the first proximal portion 194. In some embodiments, the seal 198 may be a septum seal in the wall of the Y-connector 190 within the first proximal portion 194 that is configured to be pierced by the needle 40 and the dilator 26.

A rigid casing 200 may be disposed on the Y-connector 190 to provide structure to the Y-connector 190. The casing 200 may be any suitable shape, for example a Y-shape that complements the shape of the Y-connector 190. The casing 200 may be a unitary piece or, in some aspects, it may include separate components, for example a first casing component disposed on the first proximal portion 194 and a second casing component disposed on the second proximal portion 196. The rigid casing 200 may be formed of a plastic, such as polycarbonate.

Figure 13:
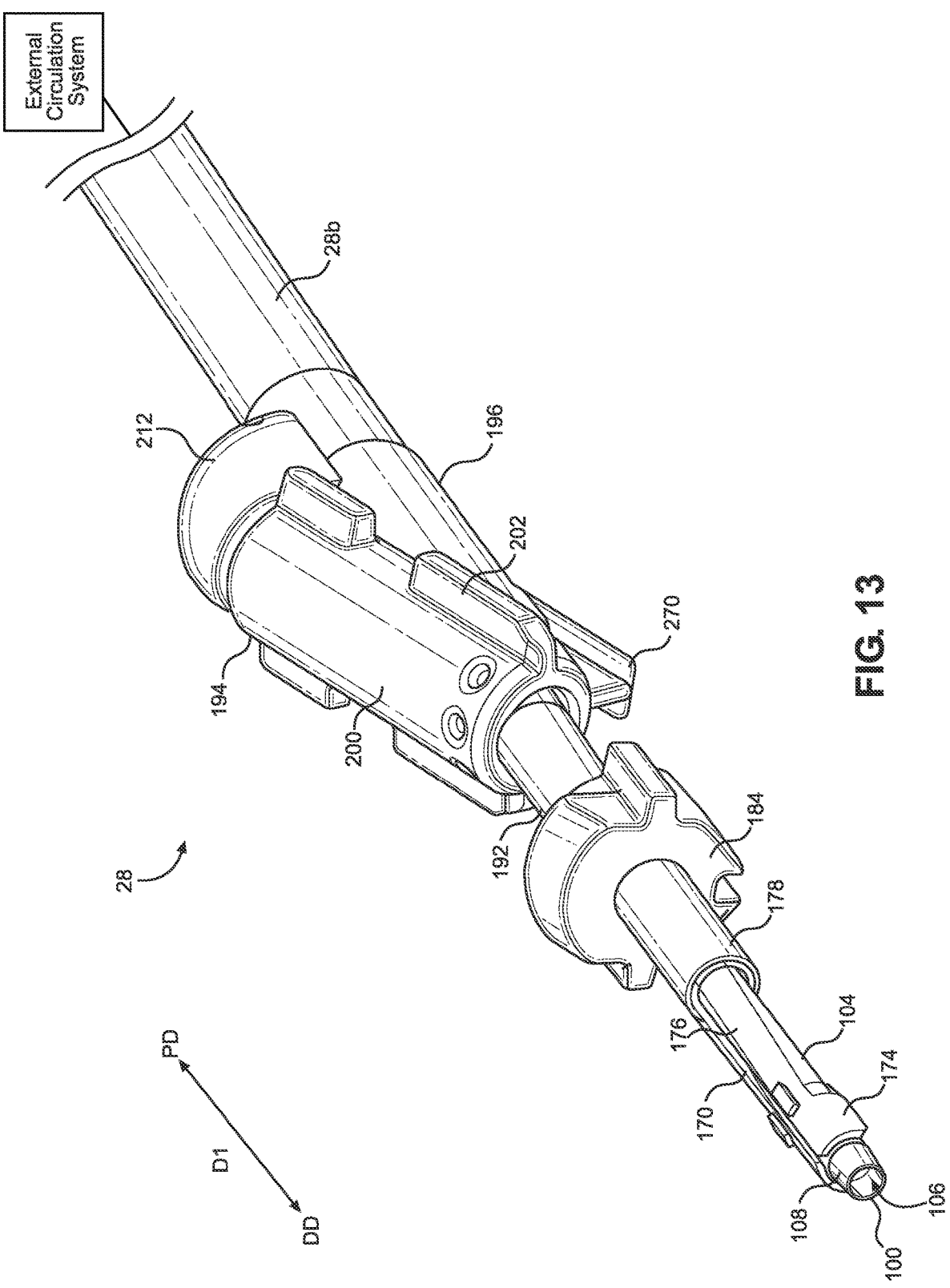
FIG. 13 is an isometric view of a cannula system according to another aspect of this disclosure.

As shown, for example, in FIG. 13, the rigid casing 200 may include a locking component 202 disposed thereon for releasably engaging the cannula system 28 with the cannula insertion device 20. The cannula insertion device 20 includes a complementary locking component 224 (see FIGS. 6 and 7) that is configured to interact with the locking component 202 to releasably lock the cannula system 28 to the housing 220 of the cannula insertion device 20 to prevent inadvertent dislodging, disconnecting, relative translation, or relative rotation. The locking components 202, 224 may be any suitable locking mechanism, such as a protrusion, a rail, a hook, a latch, or another mechanism. The locking engagement may be reversed to de-couple the cannula system 28 from the cannula insertion device 20.

Referring back to FIGS. 1-7A showing the cannula insertion device 20, a release mechanism 226 may be disposed on the housing 220 of the cannula insertion device 20 and be configured to actuate movement of the locking component 224 on the housing 220. When the locking component 224 on the housing 220 is moved, it disengages from the locking component 202 on the casing 200, thus allowing the cannula system 28 to be removed from the cannula insertion device 20. The release mechanism 226 may be a button, a switch, a latch, or another suitable mechanism. In some aspects, a second release mechanism 226b may be disposed on the housing. The second release mechanism 226b may be used in case the primary release mechanism 226 does not sufficiently de-couple the components or in case of another emergency.

Figure 15:
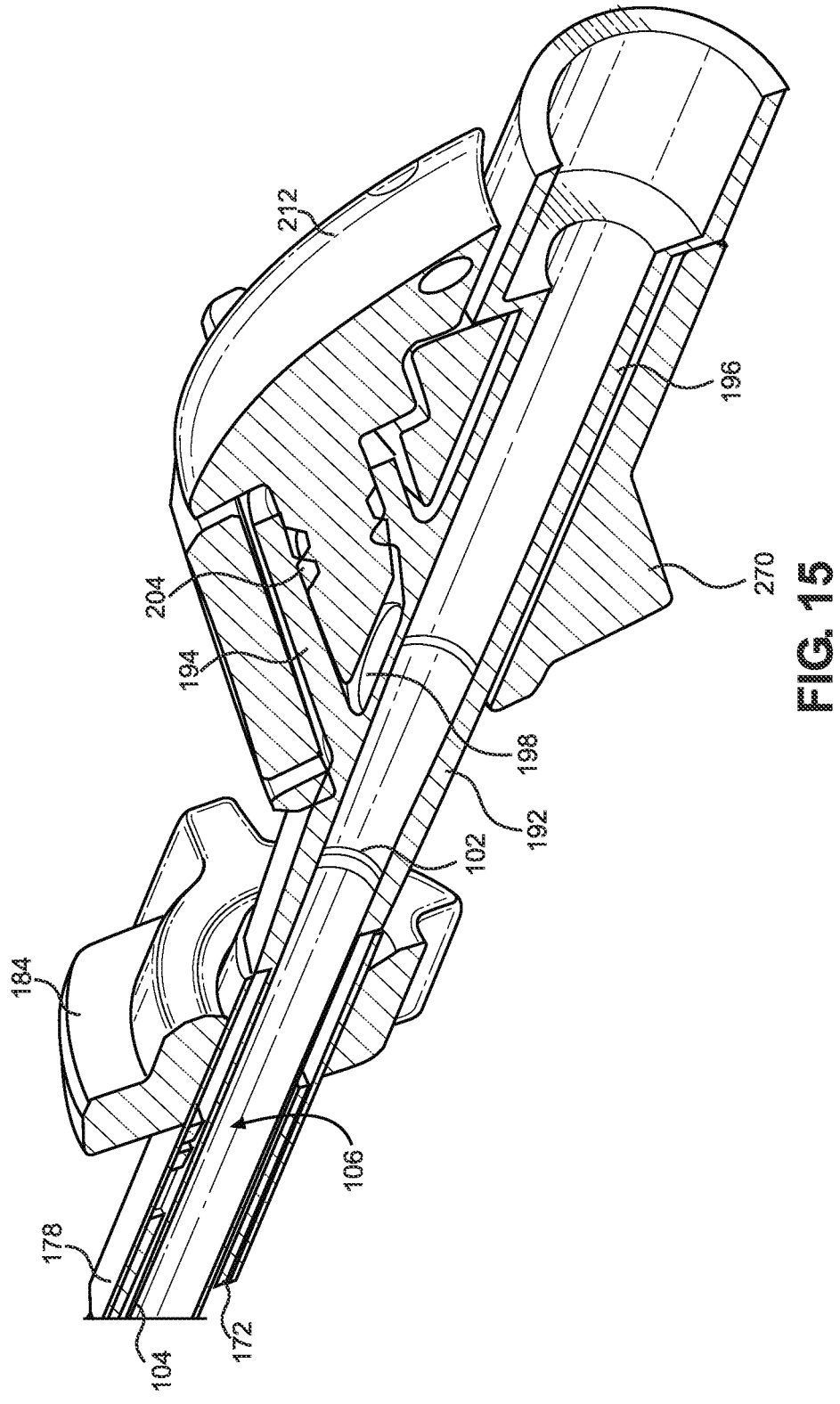
FIG. 15 is an isometric cross-sectional view of a portion of the cannula system of FIGS. 13 and 14.

In some aspects, the casing 200 may further include a guide 270 on one of the first proximal portion 194, the second proximal portion 196, or both proximal portions (see, for example FIGS. 13-15). The guide 270 corresponds to the shape of the recess 222 such that the cannula system 28 is insertable therein only in the desired orientation. For example, the guide 270 may be disposed on the second proximal portion 196, such that the second proximal portion 196 cannot be inadvertently inserted into the recess 222 and engaged with the needle assembly 22 or the dilator 26. This prevents user error and decreases the chances of damaging the cannula system 28 or the cannula insertion device 20, and prevents incorrect connections, which can lead to improper blood circulation, blood loss, intrusion of air bubbles, or leakage.

In some aspects, it is advantageous to secure the cannulated vessel to the cannula 104 once the cannula 104 has been inserted into the vessel. A clamping mechanism may be used to releasably secure the cannula 104 to the vessel. It will be appreciated that the cannula 104 may be secured to the vessel indirectly, for example by contacting a portion of the umbilical cord. In some aspects, the clamping mechanism may contact the umbilical sheath, the Wharton's jelly within the umbilical cord, or the vessel itself. In some aspects, the clamping mechanism is affixed to the cannula system 28 or, specifically, to the cannula 104. Referring again to FIGS. 13-17A, one or more collet jaws 170 may be disposed on or adjacent to the cannula 104. The collet jaws 170 may include a base 172 (seen in FIG. 14), at which the collet jaws 170 are affixed to the cannula 104, a head 174 opposite the base 172, and a deformable arm 176 extending between the base 172 and the head 174. The deformable arms 176 may be curved, such that when the base 172 is attached to and contacts the cannula 104, the head 174 is spaced away from the cannula 104. In this arrangement, the collet jaws 170 are biased open. In some aspects, the collet jaws 170 may be formed from titanium. In other aspects, the collet jaws 170 may be formed from a stainless steel, such as 306 stainless steel or 316 stainless steel.

Figure 17:
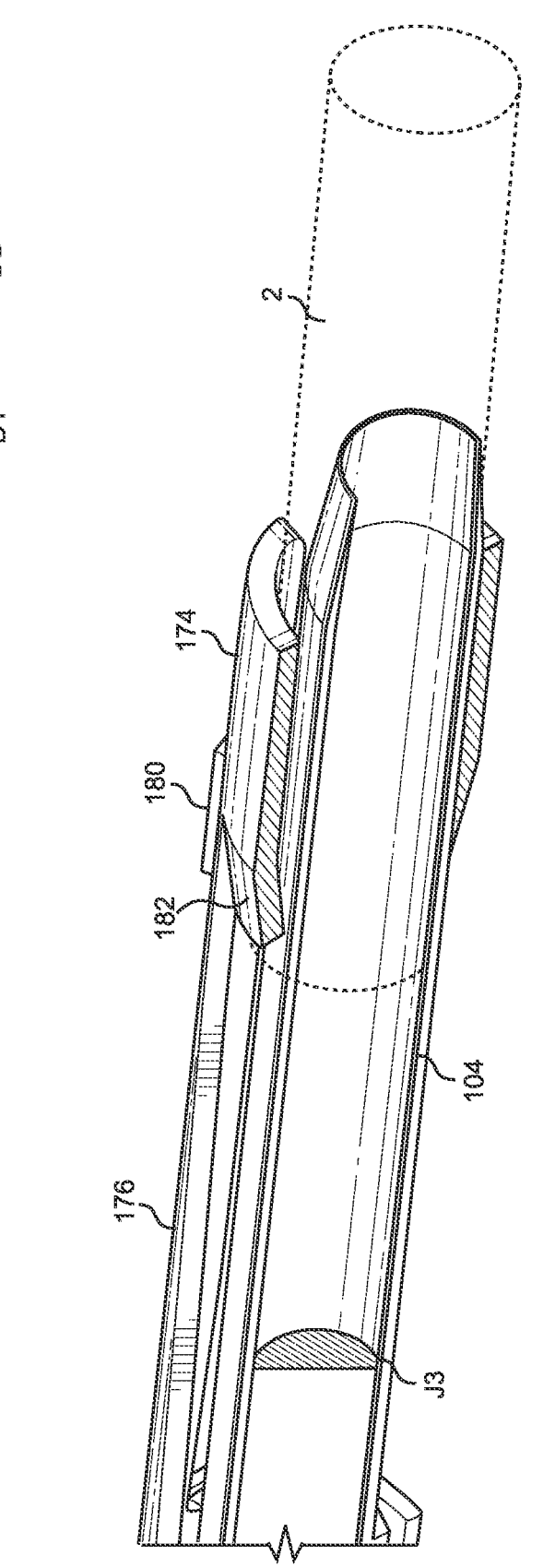
FIG. 17 is a cross-sectional view of a portion of the cannula system of FIGS. 13-16, depicting collet jaws in a closed configuration securing a vessel (shown in phantom)

As depicted in the exemplary aspect of FIG. 17, during engagement, the deformable arm 176 may be flexed and straightened along its length, such that the head 174 is moved towards the cannula 104. A portion of the cannulated vessel 2 (shown in phantom) may be disposed between the cannula 104 and the head 174, and when the deformable arm 176 is flexed toward the cannula 104, the inner wall of the vessel 2 is pressed against the outer surface of the cannula 104 by the inner surface of the head 174. This secures the vessel 2 in place relative to the cannula 104. As noted above, it will be understood that the head 174 may press the vessel 2 against the cannula 104 by pressing on another portion of the umbilical cord 1, for example the umbilical sheath, rather than contacting the vessel 2 directly.

Referring still to FIGS. 13-17A, in some aspects, the flexing of the deformable arm 176 may be actuated by a collet sleeve 178 that is configured to slidably move along the cannula 104. The deformable arm 176 may be disposed between the cannula 104 and the collet sleeve 178. As the collet sleeve 178 is moved towards the distal end 100, it slides over the deformable arm 176 and applies a force thereon, causing the deformable arm 176 to deform and straighten. The forced applied by the collet sleeve 178 should be greater than the inherent resistance to bending in the deformable arms 176. When the collet sleeve 178 is moved away from the distal end 100, the force on the deformable arm 176 is removed, and it returns to its undeformed configuration. In some aspects, a physical stop 180 may extend from a portion of the collet jaw 170 to preclude the collet sleeve 178 from moving past it. In some aspects, a stop 180 may be disposed on the head 174, on the deformable arm 176, on the base 172, or on the cannula 104.

The collet jaws 170 include features to facilitate retention of the cannulated vessel. In some aspects, one or more tines 182 (see FIGS. 16 and 17) may be disposed on the head 174, such that when the collet sleeve 178 deforms the deformable arms 176 and contacts the head 174 with the vessel, the tines 182 dig into, pierce, or bite the umbilical cord 1. The tines 182 may dig into the umbilical sheath of the umbilical cord, the blood vessel itself, or another connecting tissue present in the umbilical cord. It will be appreciated that the tines 182 need not dig into or bite entirely through the umbilical cord. Such biting or digging into further secures the vessel and prevents the vessel from translating or rotating relative to the collet jaws 170 or the cannula 104, for example, if the cannula 104 is pulled in the proximal direction PD after it has been inserted into the vessel and secured to the tissue. In some aspects, the tines 182 may be substantially orthogonal to the head 174 or, instead, may be disposed at an angle relative to the head 174, for example, such that the tines 182 extend from the head 174 away from the distal end 100 of the cannula 104. The tines 182 may dig into the tissue surrounding the vessel 2 (e.g., the umbilical sheath) or into the vessel 2 itself and prevent the vessel 2 from dislodging or pulling away from the cannula system 28 during the cannulation process or subsequent use. It will be understood that although exemplary aspects herein are directed to blood vessels in an umbilical cord, the disclosed systems may be utilized in other parts of a human or other animal body. It will be further appreciated that "tissue" may refer to umbilical tissue or other physiological tissue, including an organ.

Figure 16:
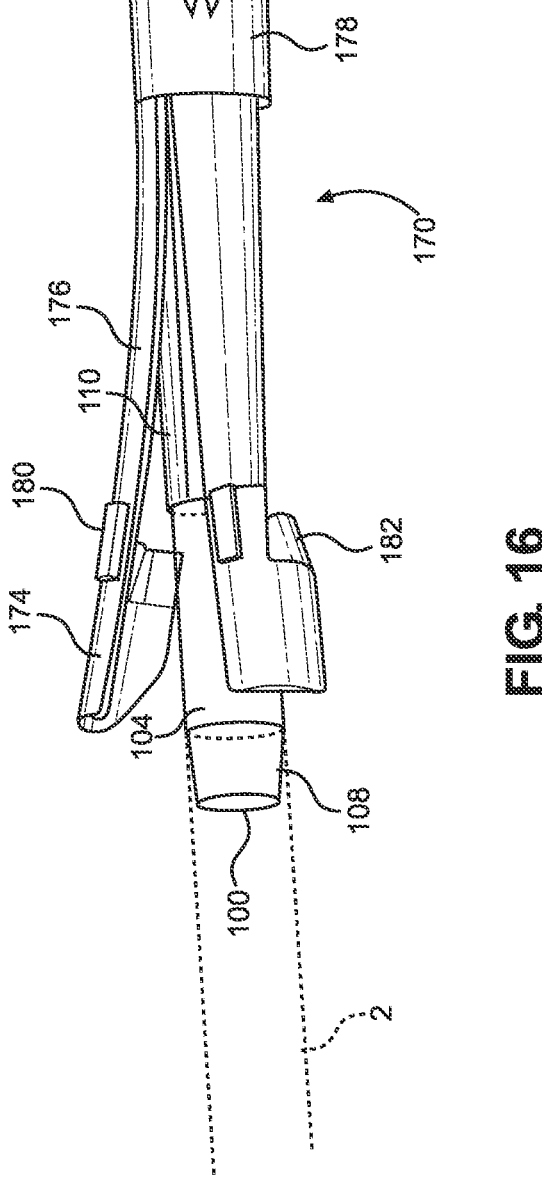
FIG. 16 is a side perspective view of a portion of the cannula system of FIGS. 13-15, depicting collet jaws in an open position and a vessel (shown in phantom)

In some aspects, it may be preferable to secure the vessel 2 as close to the distal end 100 of the cannula 104 as possible to decrease the space between the distal end 100 and the portion of the vessel 2 that is secured to the cannula system 28. This would decrease collection of blood in that space and would reduce ballooning of the vessel 2, where blood builds up between the distal end 100 and the portion of the vessel 2 that is secured and increases pressure while stretching and expanding the vessel. This may lead to undesired de-coupling of the vessel 2 from the cannula system 28, as well as stagnant blood, clotting, infections, poor blood flow, blood loss, and/or leaks. FIG. 16 depicts the collet jaws 170 in an unlocked position, where the head 174 is spaced away from the cannula 104, and FIG. 17 depicts the collet jaws 170 in a locked position, where the head 174 clamps the vessel 2 to the cannula 104 between the head 174 and the cannula 104. The collet jaws 170 may have 1, 2, 3, 4, or another suitable number of deformable arms 176 and respective heads 174. In some exemplary aspects, the collet jaws 170 have two deformable arms 176 and respective heads 174. It will be understood that the collet jaws 170 may be used to apply a clamping action on the vessel 2 by way of clamping down on the external tissue (e.g., umbilical cord or Wharton's jelly) surrounding the vessel 2 and are not required to clamp the vessel walls directly.

Figure 17A:
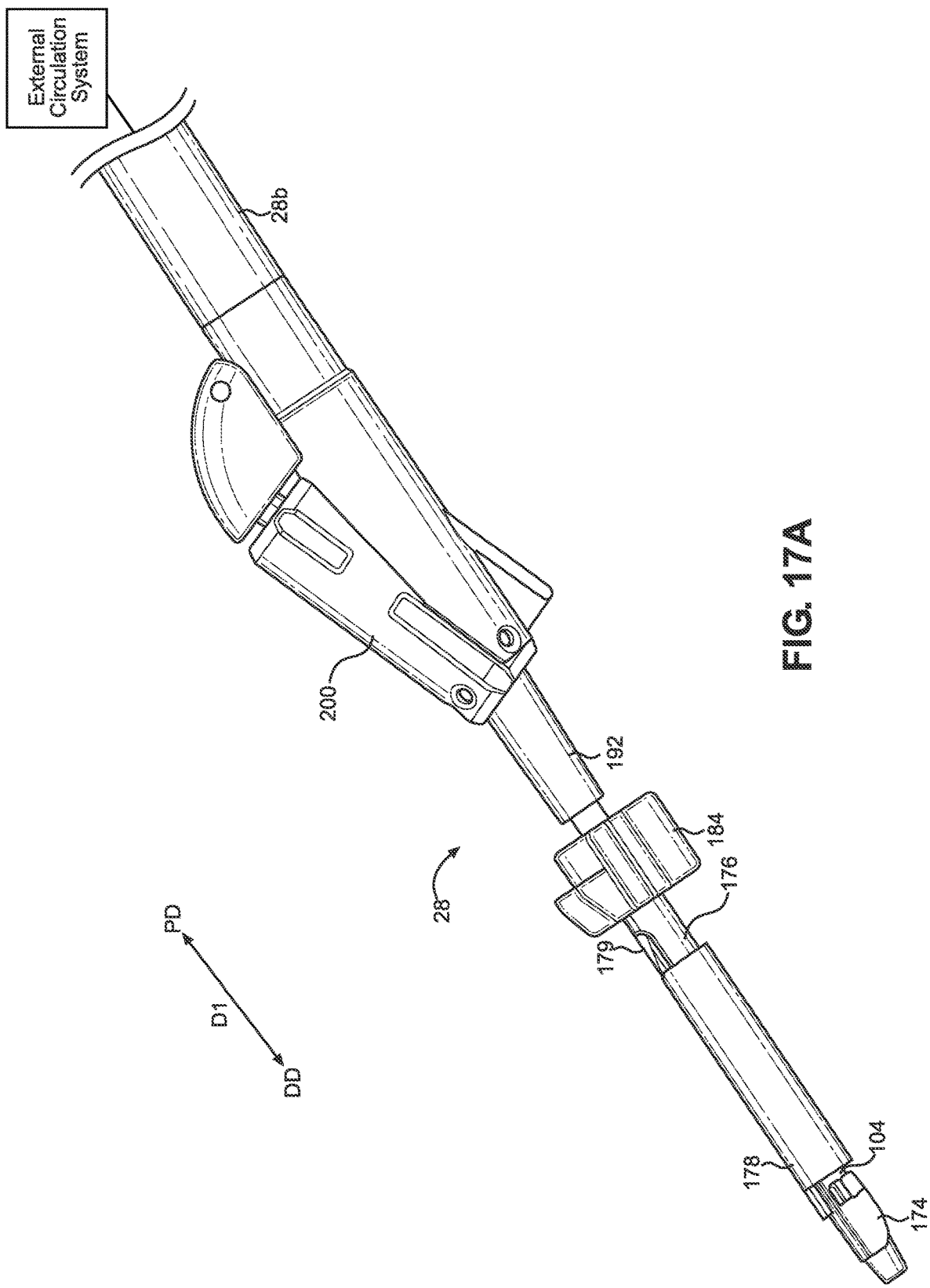
FIG. 17A is an isometric view of the cannula system of FIGS. 13-17 with the collet jaws shown in the closed configuration and showing the spring lock.

In some aspects, a spring lock 179 may be disposed on the deformable arms 176 (see FIG. 17A). The spring lock 179 is held in compression by the collet sleeve 178 when the collet jaws 170 are in the unlocked configuration. When the collet sleeve 178 is moved in the distal direction DD and causes the deformable arms 176 to deform and to secure the cannula 104 to the vessel 2, the collet sleeve 178 passes over and past the spring lock 179, allowing the spring lock 179 to un-compress. The spring lock 179 is then positioned proximal to the collet sleeve 178 (not shown) and acts as a physical barrier to prevent the collet sleeve 178 from moving in the proximal direction PD. The spring lock 179 may be moved back to the compressed configuration by pushing it towards the cannula 104 and sliding the collet sleeve 178 back in the proximal direction PD over the spring lock 179. Moving the spring lock 179 and sliding the collet sleeve 178 back allows the cannula insertion device 20 to be "reset" to disengage the collet jaws 170 from the tissue, for example, if the cannula 104 needs to be removed from the vessel.

The housing 220 may include a mechanism for moving the collet jaws 170. In some aspects, the mechanism may be part of or connected to the dilator actuator 242 described above. Referring again to FIGS. 1-7A, the dilator actuator 242 that is disposed on the housing 220 may be movable in the distal direction DD and the proximal direction PD relative to the housing 220 to cause movement of the collet jaws 170. When the dilator actuator 242 is moved in the distal direction DD, it may cause the collet jaws 170 to move from an unlocked position, in which the vessel 2 is not secured between the collet jaws 170 and the cannula system 28, to a locked position, in which the vessel 2 is secured between the collet jaws 170 and the cannula system 28. The dilator actuator 242 may be configured to contact the collet sleeve 178 such that movement of the dilator actuator 242 causes movement of the collet sleeve 178. The collet sleeve 178 may also be moved from the locked position to the unlocked position, and this movement may be accomplished by moving the dilator actuator 242 in the opposite direction than described above or, alternatively, moving the collet sleeve 178 manually (i.e., having the user move the collet sleeve 178).

In some aspects, the collet sleeve 178 may include a handle 184 that may be gripped, pushed, or pulled to translate the collet sleeve 178. In some aspects, the dilator actuator 242 may be configured to contact and move the handle 184, which is affixed to the collet sleeve 178 (see FIGS. 13-15). In some aspects, the dilator actuator 242 includes a collet engagement surface 252 that is configured to contact the handle 184 (see, for example, FIGS. 1, 2, 6, and 7). The collet engagement surface 252 may also serve as a blocking surface to prevent movement of the handle 184 too far in the proximal direction PD. The reinforced portion 110 may prevent stretching when the collet sleeve 178 is moved along the cannula 104, which helps maintain the desired size and shape of the cannula system 28 and lowers chances of damage or inadvertent disconnections of components.

The collet jaws 170 may be disposed on or adjacent the reinforced portion 110 of the cannula system 28, such that when the collet jaws 170 are in the closed position and the vessel 2 is secured to the cannula system 28, the clamping forces applied by the collet jaws 170 onto the cannula system 28 through the vessel 2 do not deform the cannula system 28 at the reinforced portion 110. According to one aspect of the disclosure, the reinforced portion 110 is configured to receive the collet jaws 170 while maintaining a cylindrical shape.

A method of assembling the cannula insertion system 10 can include the step of coupling the needle 40 to the needle actuator 50 such that the needle 40 and the needle actuator 50 are at least one (or both) of translationally locked and rotationally locked. The step of coupling the needle 40 to the needle actuator 50 can include the step of positioning at least a portion of the needle 40 in the recess 56 of the hub 52. The step of coupling the needle 40 to the needle actuator 50 can further include the step of securing the at least a portion of the needle 40 in the recess 56. The step of securing the at least a portion of the needle 40 in the recess 56 can include using adhesive, overmolding, welding, threading, etc.

The method of assembling the cannula insertion system 10 can include the step of coupling the dilator 26 to the dilator hub 246, such that the dilator 26 and the dilator hub 246 are at least one of translationally locked and rotationally locked. The step of securing the at least a portion of the dilator 26 to the dilator hub 246 can include using adhesive, overmolding, welding, threading, etc.

The method of assembling the cannula insertion system 10 can include the step of coupling the needle 40, the needle actuator 50, the dilator 26, the dilator actuator 242, and the housing 220 such that the needle 40 and the needle actuator 50 are translatable relative to both the dilator 26 and the housing 220. According to one aspect of the disclosure, the step of coupling the needle 40, the needle actuator 50, the dilator 26, the dilator actuator 242, and the housing 220 is performed after the step of coupling the needle 40 to the needle actuator 50, and after the step of coupling the dilator 26 to the dilator hub 246. The step of coupling the needle 40, the needle actuator 50, the dilator 26, the dilator actuator 242, and the housing 220 can include the step of inserting the needle 40 into the dilator lumen 96 and translating the needle 40 within the dilator lumen 96 in the distal direction DD relative to the dilator 26.

The method of assembling the cannula insertion system 10 can include the step of compressing the biasing member 62, for example, in such aspects where the biasing member 62 is a compressible spring or elastic element.

The method of assembling the cannula insertion system 10 can include the step of blocking movement of the needle assembly 22 relative to the housing 220 in the proximal direction PD. According to one aspect of the disclosure, this step can include abutting the stop surface 60 with the blocking surface 124 as described above. This step may be performed by applying a force to the needle assembly 22 in the distal direction DD. The flashback chamber 231 can be pushed on by the user to cause the needle assembly 22 to move in the distal direction DD.

The method of assembly can include the step of coupling the cannula system 28 to the housing 220. According to one aspect of the disclosure, the step of coupling the cannula system 28 to the housing 220 may include coupling the cannula system 28 to the housing 220 such that movement of the housing 220 relative to the cannula system 28 in the distal direction DD is blocked, and movement of the housing 220 relative to the cannula system 28 in the proximal direction PD is not blocked. According to one aspect of the disclosure, the step of coupling the cannula system 28 to the housing 220 includes coupling the cannula system 28 to the housing 220 such that movement of the housing 220 relative to the cannula system 28 in both the distal direction DD and the proximal direction PD is blocked. The step of coupling the cannula system 28 to the housing 220 can include the step of inserting the dilator 26 into the cannula lumen 106 and translating the dilator 26 within the cannula lumen 106 in the distal direction DD relative to the cannula system 28.

The step of coupling the cannula system 28 to the housing 220 may include orienting the cannula system 28 such that it is insertable into the recess 222 of the housing. In some aspects, where a particular orientation of the cannula system 28 relative to the housing 220 is desired, the step may further include aligning the guide 270 with opening in the recess 222 defined, for example, by the shape of the housing 220, such that the cannula system 28 is permitted to pass into the recess 222.

The method of assembly may also include engaging the first proximal portion 194 of the Y-connector 190 with the housing 220. The needle 40, the dilator 26, or both may be inserted into the first proximal channel 206, through the seal 198 (e.g., the slit seal 198), into the distal channel 210, and into the cannula lumen 106. In some aspects, the method of assembling may further include engaging the casing 200 with the housing 220 such that the cannula system 28 is precluded from translating or rotating relative to the housing. In some aspects where the casing 200 includes one or more locking components 202 and the housing includes complementary locking components 224, the step of engaging the casing 200 with the housing 220 may further include the step of securing the locking components 202 on the casing 200 with their respective counterpart locking components 224 on the housing 220 to lock the cannula system 28 to the housing 220. In some aspects, engaging the locking components 202 with locking components 224 may result in an audible click, thus providing auditory feedback to the user that the coupling action was completed successfully.

The cannula system 28 may be primed with the necessary liquid and be ready for connection to a blood vessel. The method of assembly may further include a step of priming the cannula system 28. Priming the cannula system 28 may include introducing into the cannula 104 blood, plasma, saline, PlasmaLyte, and/or a solution having a composition that mimics human physiological plasma electrolyte concentrations, osmolality, and pH. The introduces liquid or liquids may be brought to, and maintained at, the desired temperatures, pressures, and gas concentrations. It will be appreciated that the specific values of the above parameters will depend on the specific requirements of the intended use. The priming step may include a step of removing air bubbles from the cannula 104 such that the cannula 104 is entirely filled with liquid.

Figure 1:
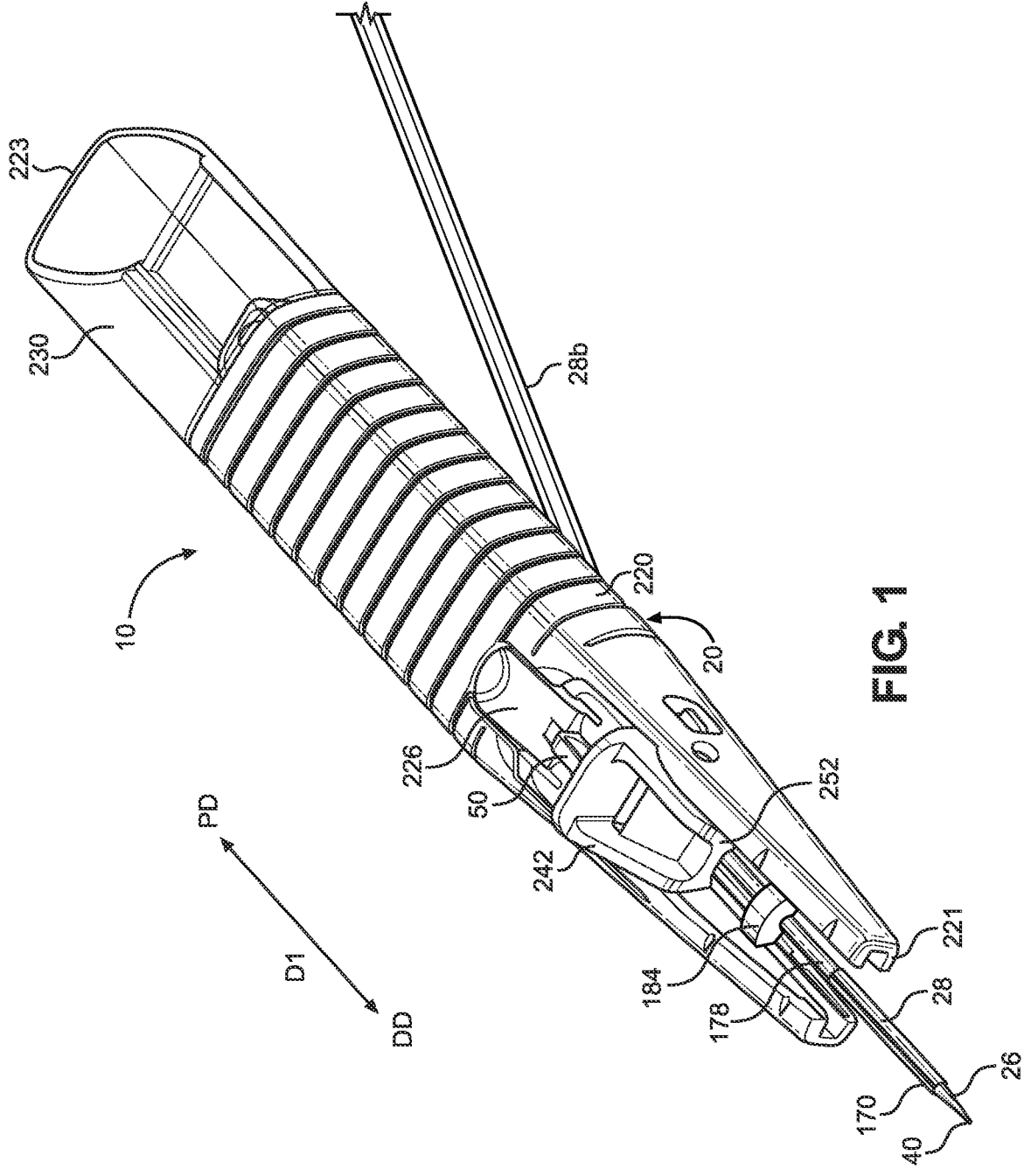
FIG. 1 is an isometric view of a cannula insertion system according to one aspect of the disclosure.
Figures 2, 2A:
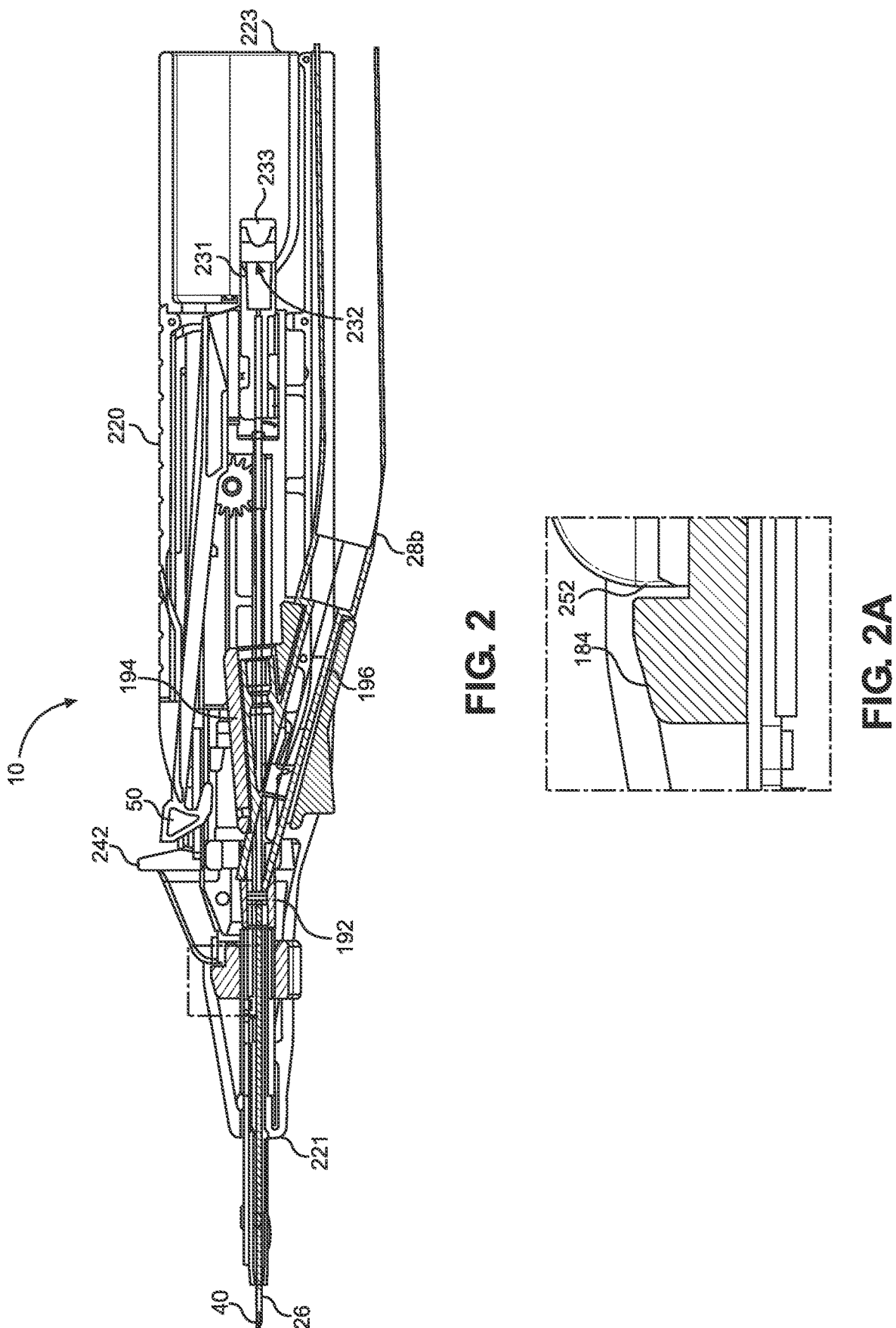
FIG. 2 is a cross-sectional view of the cannula insertion system of FIG. 1.
FIG. 2A is a close-up cross-sectional view of a portion of the cannula insertion system of FIG. 2.
Figure 3:
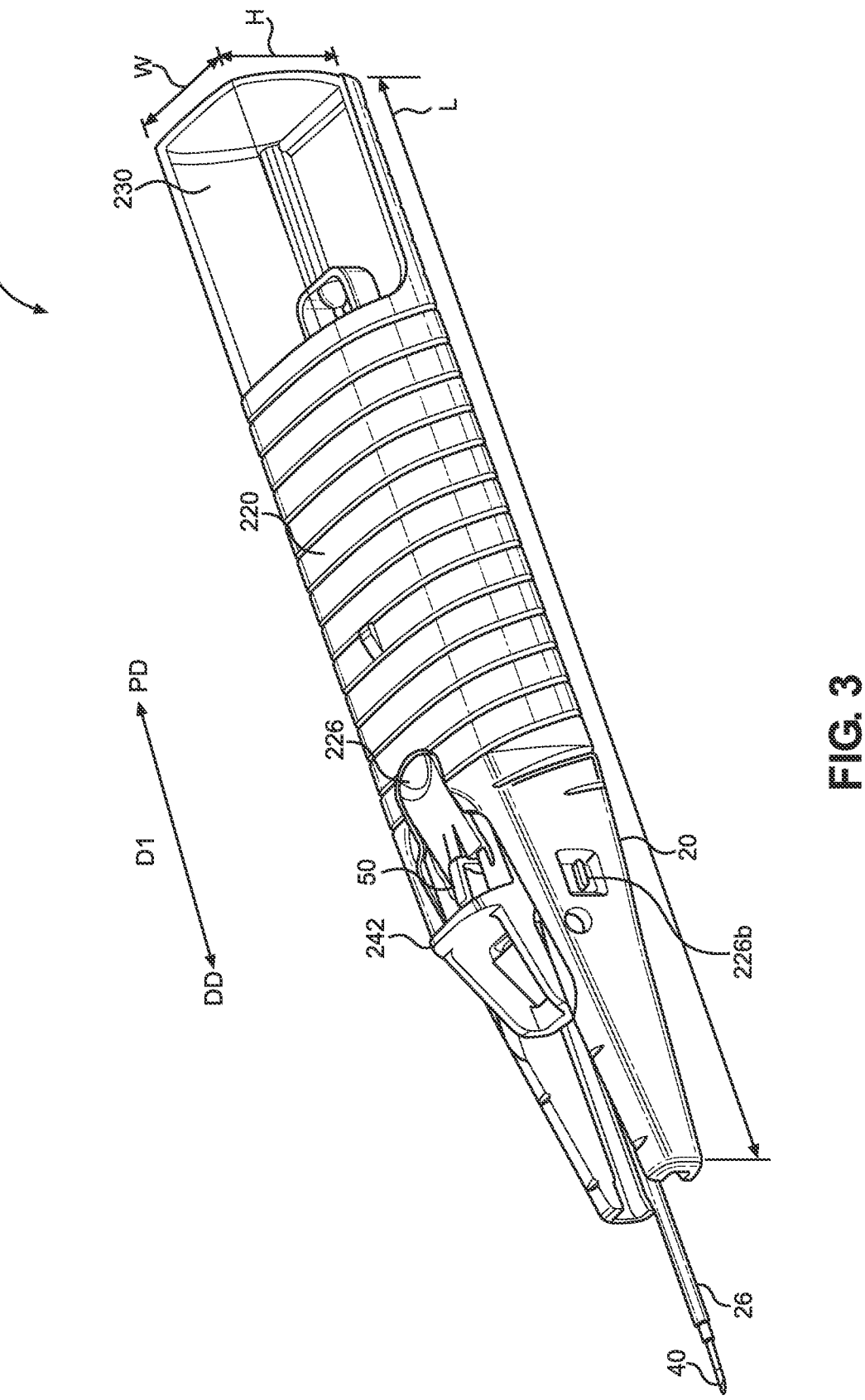
FIG. 3 is an isometric view of a cannula insertion device according to an aspect of the disclosure.
Figure 4:
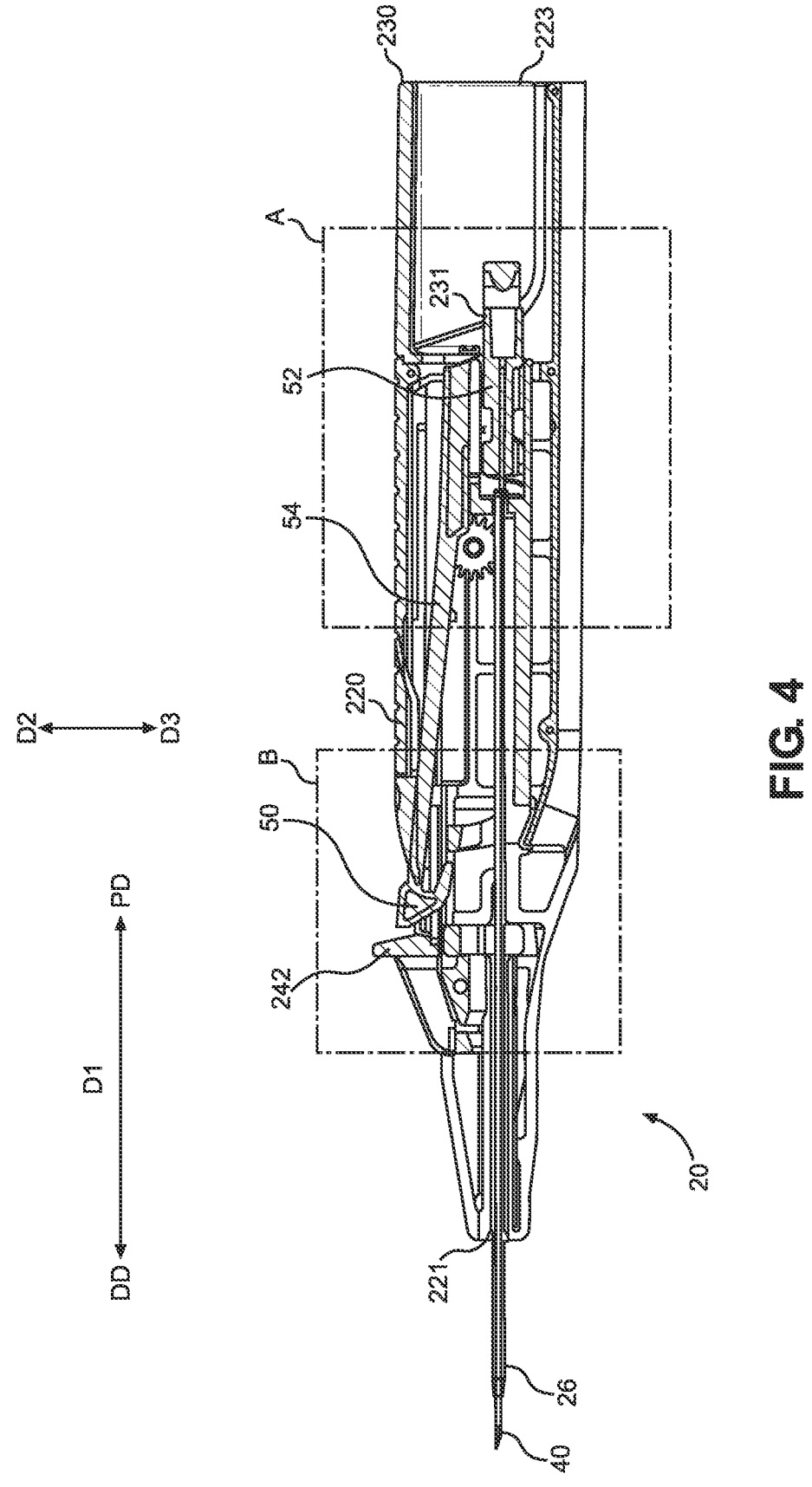
FIG. 4 is a cross-sectional view of the cannula insertion device of FIG. 3.

After completion of the method of assembling the cannula insertion system 10, the cannula insertion device 20 and the cannula system 28 can define an assembled configuration, as shown, for example, in FIGS. 1 and 2. According to one aspect of the disclosure, in the assembled configuration: 1) the needle 40 is coupled to the needle actuator 50 such that the needle 40 and the needle actuator 50 are translationally locked; 2) the dilator 26 and the housing 220 are coupled such that the dilator 26 and the housing 220 are translationally locked; 3) the needle assembly 22 is coupled to the dilator such that the needle assembly 22 is translatable relative to the dilator 26; and 4) the cannula system 28 is coupled to the housing 220 such that the cannula system 28 is translatable relative to the housing 220 in the distal direction DD, and the cannula system 28 is translationally locked relative to the housing 220 in the proximal direction PD.

After the desired use, the method may further include the step of de-coupling the cannula system 28 from the housing 220. The step of de-coupling may include actuating the release mechanism 226 to disengage the locking component 202 on the casing 200 from the corresponding locking component 224 on the housing 220. In some aspects, the method may include an alternative step of de-coupling the cannula system 28 from the housing 220 by actuating a second release mechanism 226b instead of the primary release mechanism 226. This may be done in cases when the release mechanism 226 does not, or cannot, de-couple the cannula system 28 from the housing 220, for example, in an emergency situation. In some aspects, actuating the release mechanism 226 or the second release mechanism 226b results in an audible click, thus providing auditory feedback to the user that the de-coupling action was completed successfully. After disengaging the locking components 202, 224 from each other, the cannula system 28 may be removed from the recess 222 and out of the housing 220. The needle 40 may be removed from the cannula lumen 106, pulled out through the seal 198, and removed out of the first proximal channel 206. The dilator 26 may be removed from the cannula lumen 106, pulled out through the seal 198, and removed out of the first proximal channel 206.

In some aspects, the method of assembly may further include inserting a fitting 212 into the first proximal channel 206 (see FIGS. 13 and 15, showing the fitting 212, and FIG. 14, showing the first proximal channel 206). The fitting 212 can be a cap or plug to block blood flow out of the first proximal channel 206. In some aspects, the first proximal portion 194 may include a sealing element 204 configured to engage with the fitting 212 to create a liquid-tight seal between the fitting 212 and the first proximal portion 194. The sealing element 204 may be a cross-slit seal. The sealing element 204 and the fitting 212 together may form a liquid-tight seal. The seal 198 and the seal formed between the sealing element 204 and the fitting 212 help prevent any liquid from moving into the first proximal channel 206 from the cannula lumen 106, or any debris from moving into the cannula lumen 106 from the first proximal channel 206, after the cannulation process is completed.

The cannula insertion device 20 can be configured such that, in the assembled configuration, the housing 220 abuts the cannula system 28 such that movement of the housing 220 in the third direction D3 relative to the cannula system 28 is prevented.

The assembled configuration of the cannula insertion system 10 can include an extended configuration (as shown in FIGS. 18A and 18D, for example), in which the needle 40 and the dilator 26 are extended in the distal direction DD. The assembled configuration may further include a first retracted configuration (FIGS. 18B and 18E), in which the needle 40 is in a retracted position as explained above and the dilator 26 is in the extended position. The assembled configuration may further include a second retracted configuration (FIGS. 18C and 18F), in which both the needle 40 and the dilator 26 are in the retracted positions as explained above.

In the first and second retracted configurations, the distal end 46 of the needle 40 is positioned within the dilator lumen 96, such that the distal end 46 of the needle 40 is positioned proximally of the distal end 90 of the dilator 26. According to one aspect of the disclosure, the cannula insertion system 10 is configured such that a user can transition the cannula insertion system 10 from the extended configuration to the first retracted configuration, and vice versa, with one hand. The user may further be able to transition the cannula insertion system 10 from the first retracted configuration to the second retracted configuration, and vice versa, with one hand. The cannula insertion system 10 being configured to transition with one hand allows the user's other hand to remain free to, for example, hold the umbilical cord during the insertion procedure.

In the first and second retracted configurations, the stop surface 60 can be spaced away from the blocking surface 124. In the retracted configurations, a biasing force applied by the biasing member 62 resists movement of the needle 40 in the distal direction DD relative to the housing 220. Applying a force to the cannula insertion device 20 greater than the biasing force applied by the biasing member 62, and in a direction opposite the direction of the biasing force can move the needle 40 in the distal direction DD relative to the housing 220, and thereby transition the cannula insertion device 20 from the retracted configuration to the extended configuration.

In the extended configuration, the distal end 46 of the needle 40 is positioned outside the dilator lumen 96, such that the distal end 46 of the needle 40 is positioned distally of the distal end 90 of the dilator 26. In the extended configuration, the stop surface 60 abuts the blocking surface 124 of the housing 220, and movement of the needle 40 in the proximal direction PD relative to the housing 220 is blocked by interference of the stop surface 60 and the blocking surface 124.

According to one aspect of the disclosure, the cannula insertion system 10 can be assembled and delivered to an operating room in the retracted configuration. In the first or second retracted configuration, the distal end 46 of the needle 40 is enclosed by the dilator 26, thus lowering the chance of damaging the distal end 46 of the needle 40, and also lowering the chance of injury to a user of the cannula insertion system 10 by the sharp distal end 46 of the needle 40. Alternatively, the cannula insertion system 10 can be presented to the users such that the cannula system 28 is separated from the cannula insertion device 20. In some aspects, the cannula system 28 may be prime before being engaged with the cannula insertion device 20 as explained above. In some aspects, the cannula insertion device 20 may be delivered to the user in the first retracted configuration, wherein the dilator 26 is in the extended position and the needle 40 is in the retracted position such that the needle tip end 66 is inside the dilator lumen 96.

A method of use can include the step of transitioning the cannula insertion device 20 from the first retracted configuration to the extended configuration. The user may apply a loading force to the needle assembly 22 to move the needle 40 in the distal direction DD until the distal end 46 of the needle 40 moves outside of the dilator lumen 96 and is positioned distally of the distal end 90 of the dilator 26 along the first direction D1 and until the stop surface 60 on the needle actuator 50 is positioned distally of the blocking surface 124 along the first direction D1. For example, in some exemplary embodiments, the user may apply a force to the to the flashback chamber 231 or the plug 233. As explained above, in some aspects, the housing 220 may be open at the proximal end 221, such that a user can insert a finger or thumb into the housing 220. To apply a force to the flashback chamber 231 or the plug 233, the user may insert one or more fingers into the housing 220 (e.g., into the portion of the housing 220 that includes the translucent portion 230) and push on the flashback chamber 231. The applied force should be greater than the force being applied in the opposite proximal direction PD by the biasing member 62. The biasing member 62 can be compressed or may be extended. When the needle actuator 50 passes the blocking surface 124 in the distal direction DD, the distal end 57 of the boom arm 54 and the needle actuator 50 move in the second direction D2, thereby aligning the stop surface 60 and the blocking surface 124 along the first direction D1. The user may stop pushing the needle assembly 22 after the stop surface 60 has been moved in line with the blocking surface 124. At this position, the cannula insertion device 20 is in the extended configuration (FIGS. 18A and 18D). In some aspects, the user may receive indication that the cannula insertion device 20 is in the proper extended configuration, such as an audible click or tactile feedback.

The needle actuator 50, and the boom arm 54 specifically, may be formed of deformable but elastic or resilient material, such that the boom arm 54 may be deformed when force is applied thereto, but also may return to its undeformed state when the force is removed. As force F is applied to the actuation surface 58 at the distal end 57 of the needle actuator 50, the boom arm 54 is deformed, for example, in a third direction D3 opposite the second direction D2. When the force is removed, the boom arm 54, which is biased to return to its undeformed state, moves the distal end 57 and the attached needle actuator 50 in the second direction D2.

A method of use can include the step of advancing the cannula insertion device 20 toward a vessel 2, for example a blood vessel in an umbilical cord, while the cannula insertion device 20 is in the extended configuration with the needle 40 extended such that the distal end 46 (i.e., the needle tip) extends distally past the distal end 90 of the dilator 26. Referring to FIG. 19, the method of use can further include the step of piercing a first wall 4 of the vessel 2, with the distal end 46 of the needle 40. As shown, the assembled configuration of the cannula insertion device 20 can include the needle 40 being oriented "bevel down" such that the tip end 66 is spaced from the base end 65 in the second direction D2, such that the tip end 66 is closer to the actuation surface 58 with respect to the second direction D2, than the base end 65 is from the actuation surface 58 with respect to the second direction D2. Alternatively, the cannula insertion system 10 can include the needle being oriented "bevel up" (opposite bevel down) when the cannula insertion device 20 is in the assembled configuration. Alternatively, the cannula insertion system 10 can include the needle being oriented at an orientation that neither bevel up nor bevel down when the cannula insertion device 20 is in the assembled configuration.

As shown, the step of piercing the first wall 4 of the vessel 2 includes orienting the cannula insertion device 20 relative to the vessel 2 such that at an angle β measured from the central axis 49 of the needle 40 to the first wall 4 of the vessel 2 is between about 5 degrees and about 60 degrees, between about 10 degrees and about 45 degrees, or between about 15 degrees and about 30 degrees. The cannula insertion device 20 can define a length L2 measured from the base end 65 to the distal end 90 of the dilator 26 along the first direction D1. According to one aspect of the disclosure, the length L2 can be between about 1.5 mm to about 2 mm. Alternatively, the length L2 can be less than 1.5 mm or greater than 2 mm allowing the cannula insertion device 20 to be configurable for vessels of various sizes. The cannula insertion device 20 can be configured such that the length L2 is large enough to allow insertion of an entirety of the bevel 64 into the vessel while minimizing the chance of backwalling the vessel 2. It will be appreciated that the angle of insertion of the needle 40 may vary greatly from one application to another. For example, blood vessels in umbilical cords can be oriented in a variety of different ways, thus requiring different angles of insertion. Some exemplary and non-limiting examples of such vessels are shown in FIGS. 24A and 24B. FIG. 24A, for example, depicts a step of cannulating an arterial vessel, and FIG. 24B depicts a step of cannulating a venous vessel. It will be understood that these figures are graphical depictions and do not show all components involved in the cannulation process. Regardless of the specific angle of insertion, the cannulation process of each vessel preferably is performed such that the vessel can be properly secured to the cannula 104 without damaging the vessel itself.

The method of use can further include the step of advancing the cannula insertion device 20 in the distal direction DD relative to the vessel 2, until both the tip end 66 of the needle 40 and the base end 65 of the needle 40 are positioned within the vessel 2. The method of use can further include the step of stopping movement of the cannula insertion device 20 in the distal direction DD, relative to the vessel 2, prior to the tip end 66 of the needle 40 piercing a second wall 6 of the vessel 2.

The method of use can include the step of advancing the cannula insertion device 20 in the distal direction DD relative to the vessel 2, until the tip end 66 of the needle 40, the base end 65 of the needle 40, and the distal end 90 of the dilator 26 are each positioned within the vessel 2. The step of advancing the cannula insertion device 20 in the distal direction DD relative to the vessel 2, until the tip end 66 of the needle 40, the base end 65 of the needle 40, and the distal end 90 of the dilator 26 are each positioned within the vessel 2 can include inserting at least a portion of the tapered portion 98 of the dilator 26 in the vessel 2. Next, as shown in FIG. 20, the needle 40 can then be retracted such that the tip end 66 of the needle 40 is more proximal to the distal end 90 of the dilator 26.

After at least a portion of the tapered portion 98 of the dilator 26 is positioned within the vessel 2, the method of use can include the step of retracting the needle 40. The step of retracting the needle 40 can include the step of moving the needle 40 relative to the vessel 2 in the proximal direction PD. According to one aspect of the disclosure, the step of retracting the needle 40 includes the step of moving the needle 40 in the proximal direction PD until the needle 40 is no longer positioned within the vessel 2. The step of retracting the needle 40 can be performed while maintaining the relative positions of the dilator 26 and the vessel 2.

According to one aspect of the disclosure, the step of retracting the needle 40 includes the step of moving the needle actuator 50, for example, by using a finger to push down on the actuation surface 58. The user may push on the actuation surface 58 in a direction, for example a direction toward the needle 40, such as the third direction D3. The force exerted on the actuation surface 58 must be greater than any inherent resistance to bending from the boom arm 54 itself and great enough to temporarily deform the boom arm 54 and move the distal end 57 towards the needle. According to one aspect of the disclosure, the boom arm 54 can be designed with a flexed shape such that the boom arm 54 provides its own biasing mechanism. In some aspects where additional biasing forces are applied to the boom arm 54, the force exerted on the actuation surface 58 must be greater than those biasing forces.

The step of retracting the needle 40 can include the step of sliding the stop surface 60 along the blocking surface 124, for example in the third direction D3, until the stop surface 60 and the blocking surface 124 are no longer aligned along the first direction D1. Once the stop surface 60 and the blocking surface 124 are no longer aligned along the first direction D1, the force applied by the biasing member 62 (see for example FIG. 18B) moves the needle actuator 50, the boom arm 54, the hub 52, and the attached needle 40 in the proximal direction PD relative to the housing 220. In some aspects, retracting the needle 40 may result in an audible click, thus providing auditory feedback to the user that the needle retraction was completed successfully.

Referring to FIG. 21, the method of use can include the step of advancing the cannula insertion device 20 in the distal direction DD relative to the vessel 2 until both, the distal end 90 of the dilator 26 and the distal end 100 of the cannula system 28, are positioned within the vessel 2. As shown in the illustrated embodiment, the step of advancing the cannula insertion device 20 as such can include inserting at least a portion of the tapered portion 108 of the cannula system 28 into the vessel 2.

According to one embodiment, the step of advancing the cannula insertion device 20 in the distal direction DD relative to the vessel 2, until both the distal end 90 of the dilator 26 and the distal end 100 of the cannula are positioned within the vessel 2, is performed after the step of retracting the needle 40. This step can include inserting an entirety of the tapered portion 108 of the cannula system 28 into the vessel 2.

The method of use can include the step of retracting the dilator 26. The step of retracting the dilator 26 can include the step of moving the dilator 26 relative to the vessel 2 in the proximal direction PD. According to one aspect of the disclosure, the step of retracting the dilator 26 includes the step of moving the dilator 26 in the proximal direction PD until the dilator 26 is no longer positioned within the vessel 2. The step of retracting the dilator 26 can be performed while maintaining the relative positions of the cannula system 28 and the vessel 2. According to one aspect of the disclosure, the step of retracting the dilator 26 is performed after the step of advancing the cannula insertion device 20 in the distal direction DD relative to the vessel 2, until both the distal end 90 of the dilator 26 and at least the distal end 100 of the cannula are positioned within the vessel 2.

The step of retracting the dilator 26 may include applying a force to the dilator actuator 242 to cause the dilator actuator 242 to move along the first direction D1. The dilator actuator 242 may be connected to the rack and pinion gear system 260.

In some aspects, the step of moving the dilator actuator 242 may include moving the dilator actuator 242 in the distal direction DD. This may cause the second rack 268, which is engaged with the second pinion 266, to also move in the distal direction DD. The second pinion 266 may be fixed to the housing 220 such that the second pinion 266 may rotate but is precluded from translating along the first direction D1. Movement of the second rack 268 causes rotation of the second pinion 266. In some aspects, the second pinion 266 is connected to the first pinion 262, such that when the second pinion 266 is rotated, the first pinion 262 is also rotated. When the second pinion 266 is rotated, the first pinion 262 is rotated and causes movement of the first rack 264 that is engaged with the first pinion 262. Such rotation may cause the first rack 264 to move in the proximal direction PD. The dilator assembly 25 and dilator 26 may be connected to the first rack 264, such that when the first rack 264 is moved in the proximal direction PD, the dilator 26 is also moved in the proximal direction PD. In some aspects, retracting the dilator 26 may result in an audible click, thus providing auditory feedback to the user that the dilator retraction was completed successfully. The cannula insertion device 20 with both the needle 40 and the dilator 26 in the retracted positions is depicted in FIG. 18C.

The method of use can include the step of securing the position of the cannula system 28 relative to the vessel 2. For example, the cannula 104 can be clamped to the vessel 2. In some aspects, one or more collet jaws 170, as described above, may be disposed on the cannula system 28 for securing the cannula 104 to the vessel 2.

The method of use can include the step of moving the collet jaws 170 from an unlocked position, in which the vessel 2 is not secured between the collet jaws 170 and the cannula 104 (see FIG. 16, showing a vessel 2 in phantom), to a locked position, in which the vessel 2 is secured between the collet jaws 170 and the cannula 104 (see FIG. 17, showing a vessel 2 in phantom). The step of moving the collet jaws 170 to the locked position may include moving the collet sleeve 178 in the distal direction DD towards the distal end 100 of the cannula 104, such that the collet sleeve 178 slides over the deformable arms 176 and causes the deformable arms 176 to deform, such that the head 174 is moved towards the cannula 104. The farther the collet sleeve 178 is moved in the distal direction DD, the closer the head 174 moves to the cannula 104. The portion of the vessel 2 that is to be secured may be positioned between the cannula 104 and the head 174, such that when the collet sleeve 178 is moved in the distal direction DD, the head 174 contacts the vessel 2 and compresses the vessel 2 between the head 174 and the cannula 104 (see FIG. 17).

The step of moving the collet sleeve 178 may include the step of moving a collet handle 184. The handle 184 may be affixed to the collet sleeve 178, such that when the handle 184 is moved in the distal direction DD, the collet sleeve 178 is also moved in the distal direction DD.

The step of moving the collet handle 184 may include moving the dilator actuator 242 in the distal direction DD until the collet engagement surface 252 contacts the handle 184 and pushing the handle 184 in the distal direction DD with the collet engagement surface 252.

In some alternate aspects, the step of clamping the vessel 2 can be performed with a vessel clamp that is configured as a single handed, pinch-operated clip, which secures the thin and slippery umbilical vessel to the cannula.

The step of securing the position of the cannula system 28 relative to the vessel 2 can include suturing the cannula 104 to the vessel 2. According to one embodiment, a suture can be wrapped around the reinforced portion 110 of the cannula 104.

The step of securing the position of the cannula system 28 relative to the vessel 2 can be performed after the step of retracting the dilator 26.

The method of use may also include the step of de-coupling the cannula system 28 from the cannula insertion device 20 as described above. The step of de-coupling may include actuating the release mechanism 226 to disengage the locking component 202 on the casing 200 from the corresponding locking component 224 on the housing 220. In some aspects, the method may include an alternative step of de-coupling the cannula system 28 from the housing 220 by actuating a second release mechanism 226b instead of the primary release mechanism 226. This may be done in cases when the release mechanism 226 is not sufficient in de-coupling the cannula system 28 from the housing 220 or in other emergency situations. In some aspects, actuating the release mechanism 226 or the second release mechanism 226b results in an audible click, thus providing auditory feedback to the user that the de-coupling action was completed successfully.

The method of use can further include the step of attaching a fitting 212 to the first proximal portion 194 after the cannula system 28 has been disconnected from the cannula insertion device 20. The fitting 212 may be moved through the sealing element 204, which may be a trocar valve or a cross-slit valve, and block passage of blood out of the first proximal channel 206. The fitting 212 may also displace any liquid between the seal 198 and the sealing element 204 and prevent additional liquid from entering the space between the two seals. Displacing (or evacuating) the liquid between the seal 198 and the sealing element 204 removes stagnant blood or priming fluid. The fitting 212 may also provide a physical barrier adjacent to the seal 198 to prevent the seal 198 from being forced open due to pressure in the cannula lumen 106. In some aspects, the fitting 212 may be tethered to the rigid casing 200 or to the cannula 104.

The cannula insertion system 10 can be part of a kit that includes one or more of the cannula insertion devices 20, one or more of the cannula systems 28, one or more of the needle assemblies 22, one or more of the dilator assemblies 25, or any combination thereof. The method of use can include repeating any of the steps above two additional times, such that three of the cannula insertion systems 10 are used to create a passage into three vessels 2, for example. According to one aspect of the disclosure, the three vessels can include a vein and two arteries, the vein and two arteries being positioned in an umbilical cord of a neonate. It will be appreciated that blood vessels in an umbilical cord can have different sizes, and so appropriately-sized components of the disclosed systems should be used with each vessel. The method of use can include the step of securing the cannula system 28 of each of the cannula insertion devices 20 relative to one another such that movement of any one of the cannula systems 28 relative to any of the other cannula insertion systems 28. Securing the cannulas 104 can include wrapping a suture around each of the cannulas 104. The step of securing the cannulas 104 can result in each of the cannula system 28 remaining aligned with their respective vessel 2 while reducing rubbing and friction between the cannula system 28 and the respective vessel 2.

According to one aspect of the disclosure, the cannula insertion system 10 can include wrapping, tape, sutures, or another structure configured to secure the cannulas 104 of multiple cannula insertion devices 20 together after the cannulas 104 are inserted into respective vessels. According to one aspect of the disclosure, the cannula insertion system 10 can include cannulas 104 of different sizes. It will be appreciated that the size of the cannula 104 may depend on the intended application of that cannula 104. For example, the size of the cannula 104 may be determined based on which specific blood vessel is to be cannulated. In some exemplary aspects, the cannula 104 may have a size in a range from about 4 Fr to about 18 Fr. The cannula 104 may be 4, 5, 6, . . . , 18 Fr, or another size that is suitable for the intended use. In some exemplary applications where multiple cannulas 104 may be introduced into differently sized blood vessels, the separate cannulas 104 may have different sizes. For example, in aspects where the cannula 104 is to be introduced into a first type of blood vessel (e.g., an artery of an umbilical cord) the cannula 104 may be between about 5 Fr and about 12 Fr, and where the cannula 104 is to be introduced into a second type of blood vessel (e.g., a vein of an umbilical cord) the cannula 104 may be between about 12 Fr and about 18 Fr.

FIG. 22 depicts an exemplary process 300 of cannulating a vessel 2. In step 302, the cannula insertion system 10 is positioned relative to the vessel 2 such that the needle 40 is at the desired angle and location and in a position to pierce the vessel 2. It will be appreciated that other surgical preparation steps may be performed before or after step 302, such as disinfecting, cleaning, or otherwise preparing the vessel 2, or priming the cannula system 28.

In step 304, the cannula insertion device 20 is moved towards the vessel 2 such that the needle 40 pierces the wall of the vessel 2. It will be appreciated that the needle 40 is an appropriate size and rigidity to pierce the desired vessel. After the needle 40 pierces the wall of the vessel 2, blood from the vessel 2 can flow through the cannula insertion system 10 and exit at the flashback chamber 231 through the opening 232. The blood can drip into the recess 222 of the housing 220, and the user can visually detect the presence of blood in the recess 222 by looking through the translucent portion 230 or through the open proximal end 223 of the housing 220. This can indicate to the user that the vessel 2 has been successfully pierced.

In step 306, after piercing the vessel 2, the dilator 26 is moved into the vessel 2 through the opening created by the needle 40 in step 304. The dilator 26 is translated into the vessel 2 to enlarge the opening in the wall of the vessel 2.

In step 308, the needle 40 may be retracted according to the mechanisms described throughout this specification. This removes the sharp needle tip from within the vessel 2 and reduces chances of "backwalling" the vessel or otherwise piercing, scratching, or irritating the vessel walls. This also allows for more space in the vessel 2, into which the dilator 26 may be moved to further enlarge the opening in the vessel wall.

In step 310, the dilator 26 may be retracted as described throughout this specification. Retracting the dilator 26 provides more room inside the vessel 2 for the cannula 104 and also increases open space inside the cannula lumen 106, which allows for more blood to flow from the vessel 2 into the cannula system 28.

In step 312, the tip of the cannula 104 is moved into the vessel 2 through the enlarged hole in the vessel wall. Entry of the cannula 104 may be facilitated by the tapered portion 108 at the distal end 100 of the cannula 104. The blood in the vessel 2 may now flow into the cannula lumen 106. The blood can flow through the cannula lumen 106, through the second proximal portion 196 of the Y-connector 190, and through the tube 28b that is connected to (or is a part of) the cannula system 28.

In step 314, the cannula 104 may be secured to the vessel 2 to prevent de-coupling of the vessel and the cannula. The step of securing the cannula 104 to the vessel 2 may be accomplished by moving one or more collet jaws 170 from an unlocked position to a locked position as described throughout this specification. Specifically, the step may include moving the collet sleeve 178 to cause the deformable arms 176 to deform and move the head 174 towards the cannula 104 and the vessel 2 between the cannula 104 and the head 174. This step may further include piercing the walls of the vessel 2 with one or more tines 182.

It will be appreciated that some of the steps in process 300 may be done in a different order. For example, in some aspects, the step 310 of retracting the dilator 26 may be done after the step 312 of moving the cannula 104 into the vessel 2.

The process 300 may further include an optional step of connecting the cannula system 28 to an external circulation circuit 400 (see FIG. 25, for example), such as an extracorporeal membrane oxygenation circuit. In some aspects, this connection may be made at the second proximal portion 196 of the Y-connector 190. In some aspects, an intermediate tubing 28b may be connected to the second proximal portion 196, which can then in turn be connected to an external circulatory system. The step of connecting the cannula system 28 to an external circulatory system may be performed before step 302, such that the cannula system 28 is already connected with the external circulatory system when the vessel 2 is cannulated.

The process 300 may further include a step of introducing a liquid into the flashback chamber 231. The user may inject the liquid into the flashback chamber 231 through the opening 232. This step may include moving the plug 233 out of the opening 232 before injecting the liquid therethrough.

The process 300 may include the step of checking whether the needle 40 properly entered the vessel 2 by visually observing whether blood or priming fluid drips out of the opening 232 into the flashback chamber 231 when the needle has been retracted. This step may be performed immediately after step 308.

In some aspects, the process 300 may further include an optional step of de-coupling the cannula system 28 from the cannula insertion device 20 after securing the cannula 104 to the vessel 2. This step may include dis-engaging the locking components 202 on the cannula system 28 from the corresponding locking components 224 on cannula insertion device 20 as described throughout this specification. The step of de-coupling the cannula system 28 from the cannula insertion device 20 may further include moving the needle 40 and the dilator 26 through the seal 198 such that the seal 198 no longer has components inserted therethrough and is thus closed to prevent liquid from passing through.

In some aspects, the process 300 may further include an optional step of inserting a fitting 212 into the first proximal channel 206 of the first proximal portion 194 to displace any liquid that is present in the first proximal channel 206 and to prevent any liquid or debris from moving into the first proximal channel 206.

As mentioned throughout this application, the cannula system 28 may fluidly connect the neonate with an external circulation circuit. The external circulation circuit may include an oxygenator configured to provide gas exchange for the blood passing therethrough. It will be appreciated that the external circulation circuit may include other components as well to help maintain the blood that passes through the circuit at preferred parameters.

In some aspects, the cannulation process 300 can be performed on multiple blood vessels to define a blood circuit between the separate blood vessels (e.g., cannulating an arterial vessel and cannulating a venous vessel). Cannulating a first blood vessel though which blood flows from the first vessel into the cannula system 28 allows the blood to flow through the cannula lumen 106, into the second proximal portion 196 of the Y-connector 190, then into the tube 28b. The blood can then travel through an external circulation circuit (including one or more components for treating blood, such as an oxygenator). After the blood is treated by any of the components in the external circulation circuit, the blood may flow into and through a tube 28b of a second cannula system 28 that can be connected to a second blood vessel. The blood can then flow from the tube 28b of the second cannula system 28 to the second proximal portion 196 and through the cannula lumen 106 of the second cannula system 28. From the second cannula system 28, the blood can move to the second vessel that was cannulated by process 300. By cannulating at least a first vessel and a second vessel such that the cannula system 28 connected to the first vessel and the cannula system 28 connected to the second vessel are in fluid communication with one another allows the user to create a blood circuit between the first and second vessels. In such exemplary arrangements, blood can flow out of the first vessel, travel through the external circulation circuit, and flow into the second vessel. It will be appreciated that multiple first vessels (i.e., vessels out of which blood flows) and/or multiple second vessels (i.e., vessels into which the blood flows) can be cannulated and connected to a single external circulation circuit.

The components of various cannula insertion systems described throughout this specification may be manufactured from various materials that are suitable for use in a medical, surgical, or otherwise sterile environment. The cannula insertion device 20 and the cannula system 28 may include medical grade plastic or metal, or may have a combination of plastic and metal components. Suitable materials include, but are not limited to, high-density polyethylene (HDPE), polyether ether ketone (PEEK), polycarbonate, polyamide, polypropylene, polytetrafluoroethylene (PTFE), silicone, or another suitable. The material should be biocompatible and non-toxic and should not adversely react with the liquids, bodily fluids, gases, temperatures, or medicines being utilized. It will be understood that the cannula system 28 and any tubing (e.g., cannula 104 or tube 28b) used with the cannula system 28 should be non-hemolytic to avoid damaging the blood that will flow therethrough. For example, in some aspects of the cannula insertion system 10, the needle 40 may be formed from a stainless steel, the dilator 26 may be formed from HDPE, and the housing 220 may be formed from polycarbonate. The cannula 104 may be formed from a urethane or silicone. The collet jaws 170 may be formed from titanium or stainless steel, such as 304 stainless steel or 316 stainless steel.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range including the stated ends of the range, unless otherwise indicated herein, and each separate value is incorporated into the specification as if it were individually recited herein. All methods described herein can be performed in any suitable order unless otherwise indicated herein or otherwise clearly contradicted by context.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A cannula insertion system for cannulating a blood vessel in a tissue, the cannula insertion system comprising:

a cannula system including a cannula that defines a cannula lumen therethrough, the cannula having a distal end and a proximal end opposite the distal end;

a collet jaw configured to releasably secure the cannula to the blood vessel, the collet jaw being affixed to the cannula, the collet jaw having a base, a deformable arm, and a head; and a cannula insertion device configured to couple with the cannula system, the cannula insertion device including:

a dilator having a dilator body that defines a dilator lumen therethrough;

a needle having a needle body that defines a needle lumen therethrough, the needle being translatable within the dilator lumen along a first direction;

a dilator actuator configured to be moved such that movement of the dilator actuator causes movement of the dilator along the first direction;

a needle actuator configured to be moved such that movement of the needle actuator causes movement of the needle along the first direction; and a housing defining a housing recess therein, the housing recess being configured to receive the cannula system, the dilator, and the needle, wherein the needle and the dilator of the cannula insertion device are configured to be moved within the cannula lumen along the first direction, wherein when the collet jaw is in an open position, the head is spaced away from the blood vessel and the cannula, and when the collet jaw is in a closed position, the head is in contact with the tissue such that the blood vessel is held in place between the collet jaw and the cannula.

2. The cannula insertion system of claim 1, wherein the needle actuator is configured to translate the needle from a first position, in which a distal end of the needle is positioned distally of a distal end of the dilator, to a second position, in which the distal end of the needle is positioned proximally of the distal end of the dilator.

3. The cannula insertion system of claim 1, wherein the cannula system includes a Y-connector adjacent to the proximal end of the cannula, the Y-connector having a first proximal portion, which defines a first proximal channel, and a second proximal portion, which defines a second proximal channel, wherein the first and second proximal channels are configured to be in fluid communication with the cannula lumen.

4. The cannula insertion system of claim 3, wherein the first proximal portion defines a slit seal that separates the first proximal channel from the second proximal channel, the slit seal having an open configuration, in which the dilator and the needle are inserted therethrough, and a closed configuration, in which the needle and the dilator are not extending therethrough, wherein when the slit seal is in the closed configuration, liquid from the cannula lumen is precluded from moving into the first proximal channel.

5. The cannula insertion system of claim 3, further comprising a plug configured to be removably inserted into the first proximal channel.

6. The cannula insertion system of claim 1, wherein the cannula system further includes a locking element thereon, and the housing includes a locking element thereon, wherein the locking element of the cannula system is configured to releasably engage with the locking element of the housing such that the cannula system is affixed to the housing.

7. The cannula insertion system of claim 1, wherein the collet jaw further comprises a tine on the head that extends towards the blood vessel, wherein the tine is configured to dig into the tissue when the collet jaw is in the closed position.

8. The cannula insertion system of claim 1, wherein the housing includes a translucent portion configured to allow visibility through the housing into the housing recess.

9. The cannula insertion system of claim 1, wherein the cannula system is configured to be operatively connected to an extracorporeal membrane oxygenation (ECMO) system.

10. The cannula insertion system of claim 1, wherein the tissue includes an umbilical cord of a neonate.

11. A method of cannulating a blood vessel in a tissue, the method comprising the steps of:

creating an opening in a wall of the blood vessel by piercing the wall with a distal end of a needle by moving the needle towards the vessel and through the wall of the vessel;

inserting a dilator into the opening and expanding the opening;

retracting the needle such that the needle is moved out of the blood vessel;

retracting the dilator such that the dilator is moved out of the blood vessel;

inserting a cannula into the opening in the wall of the blood vessel; and moving a collet jaw from an unlocked position to a locked position to secure the cannula in the blood vessel, the collet jaw in the unlocked position configured to not contact the tissue, and the collet jaw in the locked position configured to clamp the tissue such that the blood vessel is held between the collet jaw and the cannula to preclude at least a portion of the blood vessel from translating relative to the cannula, wherein the cannula defines a cannula lumen therethrough extending between a distal end and a proximal end, and wherein the dilator and the needle are movable within the cannula lumen.

12. The method of claim 11, wherein the needle defines a distal end and a proximal end opposite the distal end, wherein the dilator defines a dilator lumen extending through the dilator between a distal end and a proximal end, and wherein the step of retracting the needle includes moving the needle in the dilator lumen from a first position, in which the distal end of the needle is outside of the dilator lumen and is distal to the distal end of the dilator, to a second position, in which the distal end of the needle is in the dilator lumen and is proximal to the distal end of the dilator.

13. The method of claim 11, further comprising the step of digging into the tissue with a tine disposed on the collet jaw.

14. The method of claim 11, further comprising connecting the cannula to an extracorporeal membrane oxygenation (ECMO) system.

15. The method of claim 14, wherein the cannula is connected to a Y-connector that splits into a first proximal portion and a second proximal portion separate from the first proximal portion, and wherein the step of connecting the cannula to the ECMO system includes connecting the second proximal portion of the Y-connector to the ECMO system.

16. The method of claim 11, further comprising moving the dilator and the needle out of the cannula lumen after the step of securing the blood vessel to the cannula.

17. The method of claim 16, wherein the cannula is connected to a Y-connector that splits into a first proximal portion and a second proximal portion separate from the first proximal portion, and wherein the step of moving the dilator and the needle out of the cannula lumen includes moving the dilator and the needle through the first proximal portion.

18. The method of claim 17, further comprising moving the needle and the dilator through a slit seal defined in the first proximal portion of the Y-connector.

19. The method of claim 17, further comprising inserting a plug into a first proximal channel of the Y-connector to prevent blood flow out of the first proximal portion.

20. The method of claim 11, wherein the tissue includes an umbilical cord of a neonate.

21. A cannula system comprising:

a cannula having a distal end and a proximal end opposite the distal end;

a cannula lumen extending through the cannula between the distal end and the proximal end;

a slit seal disposed on the cannula, the slit seal being configured to receive a cannula insertion device; and a collet jaw disposed on the cannula, the collet jaw configured to releasably secure the cannula to a blood vessel in a tissue, wherein the collet jaw is configured to move between an unlocked position, in which the collet jaw does not contact the tissue, to a locked position, in which the collet jaw is configured to forcefully clamp the tissue such that the blood vessel is precluded from translating relative to the cannula, to secure the cannula to the blood vessel, and wherein the cannula system is configured to be in fluid communication with the blood vessel and with an oxygenator.

22. The cannula system of claim 21, wherein the cannula further includes:

a Y-shaped connector having a first proximal portion and a second proximal portion, wherein the cannula lumen extends through the second proximal portion of the Y-shaped connector, and wherein the slit seal is configured to allow fluid communication between the first proximal portion and the cannula lumen.

23. The cannula system of claim 21, wherein the tissue includes an umbilical cord of a neonate.

24. A cannula for fluidly communicating with a vessel of a tissue, the cannula comprising:

a distal end coupled to a collet jaw configured to releasably secure the distal end to the vessel;

a proximal end opposite the distal end;

a cannula lumen extending through the cannula between the distal end and the proximal end;

a Y-shaped connector having a first proximal portion and a second proximal portion; and a slit seal disposed on the cannula, the slit seal being configured to receive a cannula insertion device therethrough, wherein the cannula lumen extends through the second proximal portion of the Y-shaped connector, and wherein the slit seal is configured to allow fluid communication between the first proximal portion and the cannula lumen, wherein the collet jaw is configured to move between an unlocked position, in which the collet jaw does not contact the tissue, to a locked position, in which the collet jaw is configured to forcefully clamp the tissue such that the vessel is precluded from translating relative to the cannula, to secure the cannula to the vessel.

25. The cannula of claim 24, wherein the tissue includes an umbilical cord of a neonate.

\* \* \* \* \*